(12) United States Patent
Angiuoli et al.

(10) Patent No.: US 11,972,841 B2
(45) Date of Patent: Apr. 30, 2024

(54) MACHINE LEARNING SYSTEM AND METHOD FOR SOMATIC MUTATION DISCOVERY

(71) Applicant: Personal Genome Diagnostics Inc., Baltimore, MD (US)

(72) Inventors: Samuel V. Angiuoli, Baltimore, MD (US); Derrick Wood, Baltimore, MD (US)

(73) Assignee: Personal Genome Diagnostics Inc., Baltimore, MD (US)

( * ) Notice: Subject to any disclaimer, the term of this patent is extended or adjusted under 35 U.S.C. 154(b) by 979 days.

(21) Appl. No.: 16/217,921

(22) Filed: Dec. 12, 2018

(65) Prior Publication Data

US 2019/0189242 A1    Jun. 20, 2019

Related U.S. Application Data

(60) Provisional application No. 62/726,877, filed on Sep. 4, 2018, provisional application No. 62/607,007, filed on Dec. 18, 2017.

(51) Int. Cl.
*G16B 20/20* (2019.01)
*G16B 40/20* (2019.01)

(52) U.S. Cl.
CPC ............ *G16B 20/20* (2019.02); *G16B 40/20* (2019.02)

(58) Field of Classification Search
CPC .............................. G16B 20/20; G16B 40/20

USPC ......................................................... 702/20
See application file for complete search history.

(56) References Cited

U.S. PATENT DOCUMENTS

| 9,695,479 B2 | 7/2017 | Vogelstein et al. |
| 2012/0197533 A1 | 8/2012 | Nazarenko et al. |
| 2014/0178438 A1 | 6/2014 | Sahin et al. |
| 2017/0061072 A1* | 3/2017 | Kermani ............... G16B 30/00 |
| 2017/0342500 A1 | 11/2017 | Marquard et al. |

FOREIGN PATENT DOCUMENTS

| WO | WO 2016/018481 | 2/2016 |
| WO | WO 2016/018481 A2 | 2/2016 |
| WO | WO 2017/062867 | 4/2017 |
| WO | WO 2017/136603 | 8/2017 |
| WO | WO 2017/136603 A1 | 8/2017 |

OTHER PUBLICATIONS

Induction of Decision Trees via Evolutionary Programming, J. Chem. Inf. Comput. Sci. 2004, 44, 862-870, Publication Date: Mar. 20, 2004 (Year: 2004).*
"scikit-learn user guide" (https://scikit-learn.org/stable/) , Release 0.18.2, Jun. 28, 2017 (Year: 2017).*

(Continued)

*Primary Examiner* — Russell S Negin
*Assistant Examiner* — Guozhen Liu
(74) *Attorney, Agent, or Firm* — Kilpatrick Townsend & Stockton LLP

(57) ABSTRACT

A machine learning system and method for somatic mutation discovery are provided that provides improved identification of tumor-specific mutations. The improved identification of tumor-specific mutations may affect discovery of alterations and therapeutic management of cancer patients.

27 Claims, 40 Drawing Sheets

(56) References Cited

OTHER PUBLICATIONS

Dong Yan*, Kirsten M. de Beurs: Mapping the distributions of C3and C4grasses in the mixed-grassprairies of southwest Oklahoma using the Random Forestclassification algorithm, International Journal of Applied Earth Observation and Geoinformation 47 (2016) 125-138 (Year: 2016).*

Marquard, A.M., Birkbak, N.J., Thomas, C.E et al. TumorTracer: a method to identify the tissue of origin from the somatic mutations of a tumor specimen. BMC Med Genomics 8, 58 (2015) (Year: 2015).*

International Search Report dated Mar. 4, 2019, regarding PCT/US2018/065202. (11 pages).

Spinella et al.: "*SNooPer: a machine learning-based method for somatic variant identification from low-pass next-generation sequencing*," BMC Genomics, Nov. 14, 2016, vol. 17, No. 912, pp. 1-11.

EP Extended European Search Report in European Application No. 18 891 119, dated Aug. 17, 2021, 11 pages.

PCT International Preliminary Report on Patentability in International Application No. PCT/US2018/065202, dated Jun. 23, 2020,9 pages.

Spinella et al., "SNooPer: a machine learning-based method for somatic variant identification from low-pass next-generation sequencing", BMC Genomics, Nov. 2016, 17(912):1-11.

Wood et al., "A machine learning approach for somatic mutation discovery", Science Translational Medicine, Sep. 2018, 10(457):1-33.

* cited by examiner

| |
|---|
| Test Information and Sequencing Characteristics |
| Test: CPT<br>Number of Genes: 88<br>Target Bases: 478,861<br>Sequenced Tumor Bases: 1,667,418,600<br>Sequenced Normal Bases: 822,428;100 |
| Sequence Mutations |
| CDH1 chr16 68835670Q>C |
| Amplifications |
| EGFR chr7 55086724-55275031 18-Fold Amplification |
| Rearrangements |
| Inversion Intrachromosomal EML4 chr2: 42493000 |

FIG. 8

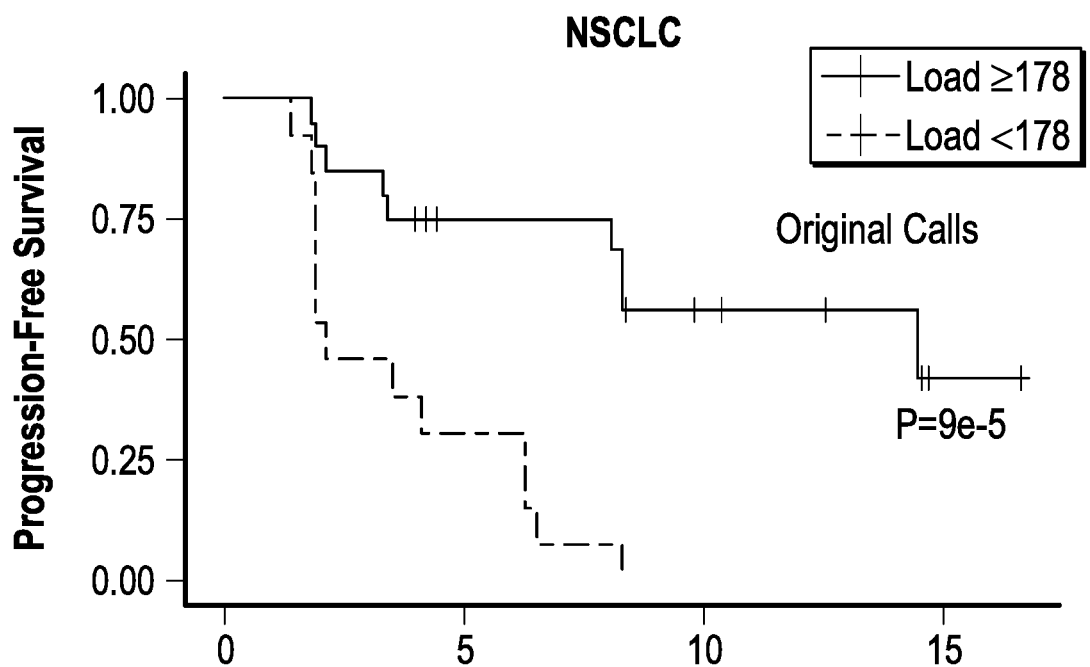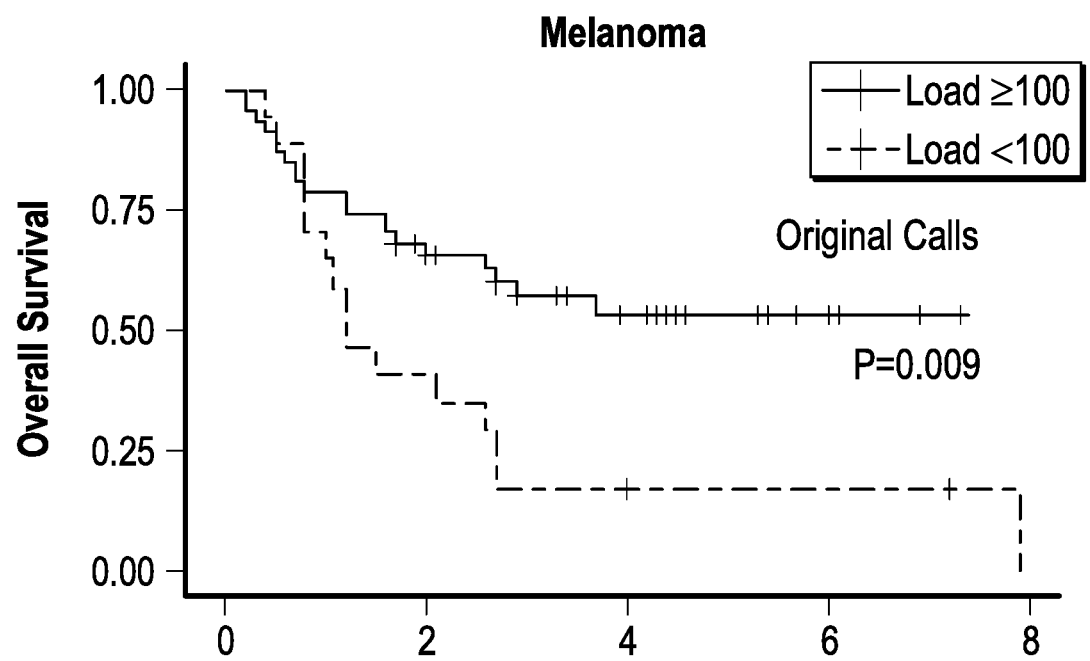
FIG. 21

Table 1. Whole Exome Sequencing Analyses and Somatic Mutation Loads

| Tumor Type* | Number of Samples | Median Mutation Load | Cerebro % Load > 100 | % Load > 250 | % Load > 500 | % Load > 1000 | Median Mutation Load | TCGA MC3 % Load > 100 | % Load > 250 | % Load > 500 | % Load > 1000 |
|---|---|---|---|---|---|---|---|---|---|---|---|
| Lung Adenocarcinoma (LUAD) | 473 | 141 | 60.3% | 29.4% | 8.9% | 2.1% | 152 | 62.8% | 31.3% | 10.1% | 2.1% |
| Bladder (BLCA) | 360 | 136 | 64.4% | 23.1% | 5.6% | 1.1% | 141.5 | 65.0% | 23.9% | 5.8% | 1.1% |
| Liver (LIHC-H) | 141 | 75 | 25.5% | 3.5% | 1.4% | 0.0% | 72 | 24.1% | 3.5% | 1.4% | 0.7% |
| Lung Squamous Cell (LUSC) | 134 | 178 | 82.8% | 27.6% | 6.7% | 1.5% | 188 | 84.3% | 34.3% | 7.5% | 1.5% |
| Melanomer (SKCM-H) | 105 | 308 | 70.5% | 57.1% | 33.3% | 9.5% | 317 | 71.4% | 58.1% | 35.2% | 11.4% |
| Colon (COAD-H) | 44 | 786.5 | 88.6% | 65.9% | 63.6% | 34.1% | 892.5 | 88.6% | 61.4% | 59.1% | 45.5% |
| Uterine (UCEC-H) | 41 | 78 | 46.3% | 46.3% | 26.8% | 0.0% | 78 | 46.3% | 46.3% | 22.0% | 0.0% |
| Kidney Renal Clear Cell (KIRC-H) | 25 | 64 | 8.0% | 0.0% | 0.0% | 0.0% | 62 | 0.0% | 0.0% | 0.0% | 0.0% |
| Head and Neck (HNSC-H) | 15 | 493 | 100.0% | 86.7% | 46.7% | 13.3% | 486 | 100.0% | 93.3% | 46.7% | 13.3% |
| Stomach (STAD-H) | 6 | 998 | 100.0% | 100.0% | 100.0% | 50.0% | 872.5 | 100.0% | 100.0% | 100.0% | 50.0% |
| Sarcoma (SARC-H) | 5 | 540 | 100.0% | 100.0% | 60.0% | 0.0% | 522 | 60.0% | 60.0% | 60.0% | 0.0% |
| Other-H | 19 | 734 | 84.2% | 73.7% | 68.4% | 36.8% | 668 | 94.7% | 84.2% | 68.4% | 36.8% |

*-H = Tumor samples enriched for high mutation load

FIG. 23

Table 2. Comparison of NGS Cancer Sequencing Panels*

| Performance Metric | CancerSelect 125 | | | | Oncomine Comprehensive Assay | | | | TruSeq Amplicon - Cancer Panel | | | |
|---|---|---|---|---|---|---|---|---|---|---|---|---|
| | TP | FN | Point Estimate | 95% CI | TP | FN | Point Estimate | 95% CI | TP | FN | Point Estimate | 95% CI |
| SBS Sensitivity | 30 | 0 | 100% | 85.9-100% | 29 | 1 | 96.70% | 80.9-99.8% | 15 | 15 | 50.00% | 33.2-66.8% |
| InDel Sensitivity | 6 | 0 | 100% | 51.7-100% | 5 | 1 | 83.30% | 36.4-99.1% | 3 | 3 | 50.00% | 18.8-81.2% |
| | TP | FP | Point Estimate | 95% CI | TP | FN | Point Estimate | 95% CI | TP | FP | Point Estimate | 95% CI |
| SBS PPV | 30 | 0 | 100% | 85.9-100% | 29 | 17 | 63.0% | 47.5-76.4% | 15 | 169 | 8.20% | 4.8-13.3% |
| InDel PPV | 6 | 0 | 100% | 51.7-100% | 5 | 0 | 100% | 46.3-100% | 3 | 6 | 33.30% | 9.0-69.1% |

*SBS:Single base substitution, TP: True Positive ,FN: False Negative, FP: False Positive, 95% CI: 95% Confidence interval, InDel: Insertion or Deletion, PPV: Positive Predictive Value

FIG. 24

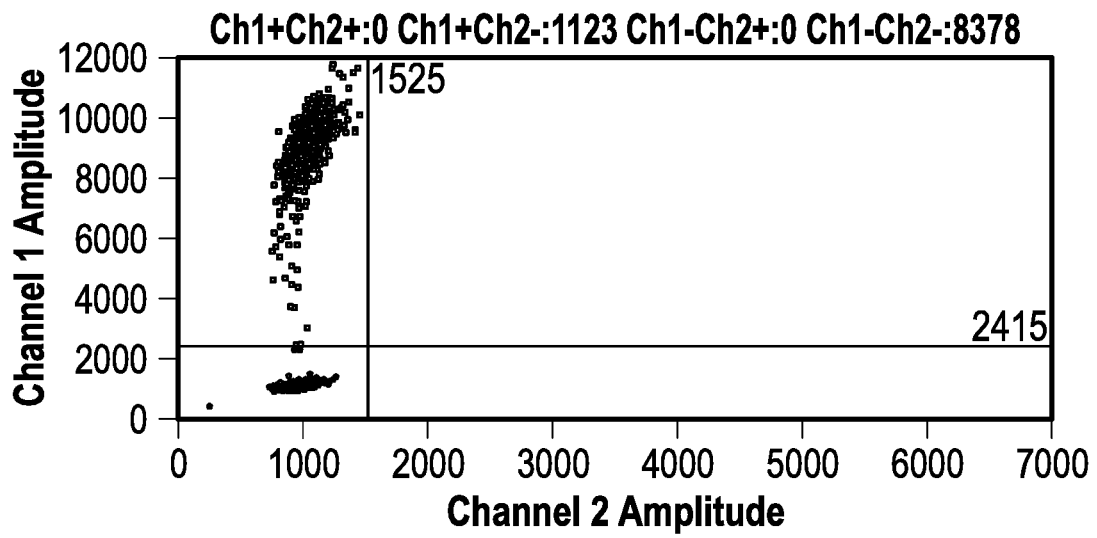
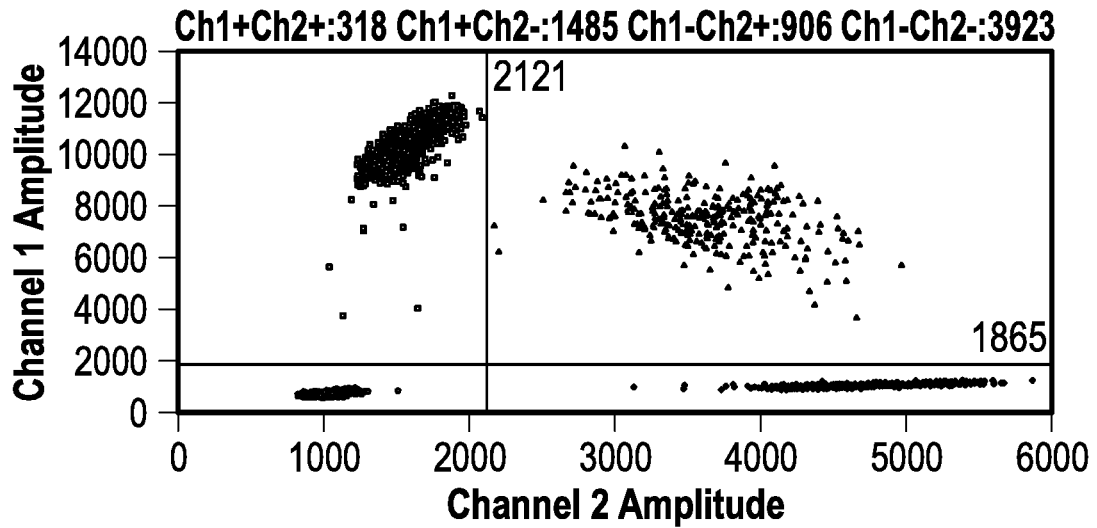
FIG. 26A
(Continued)

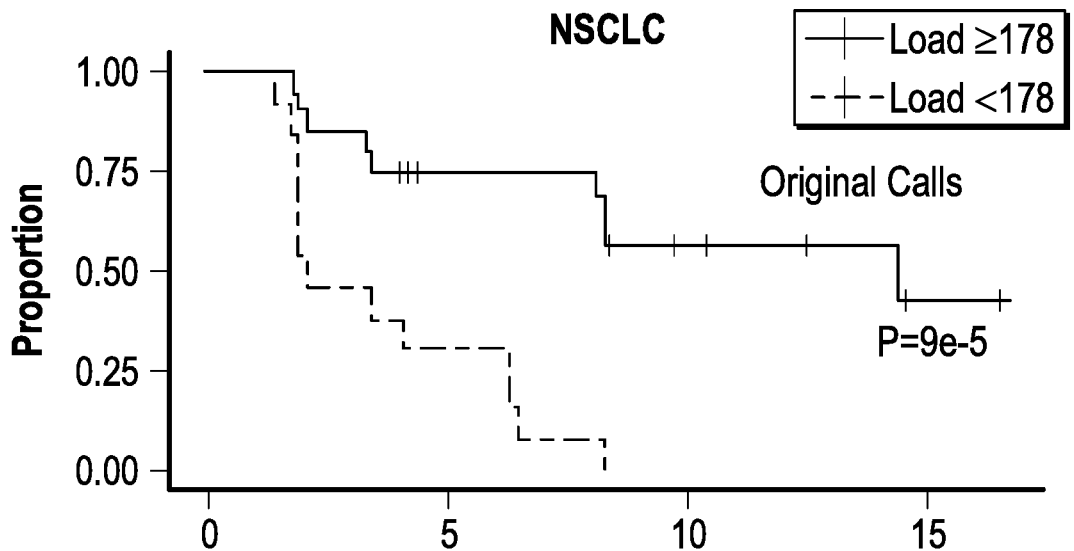
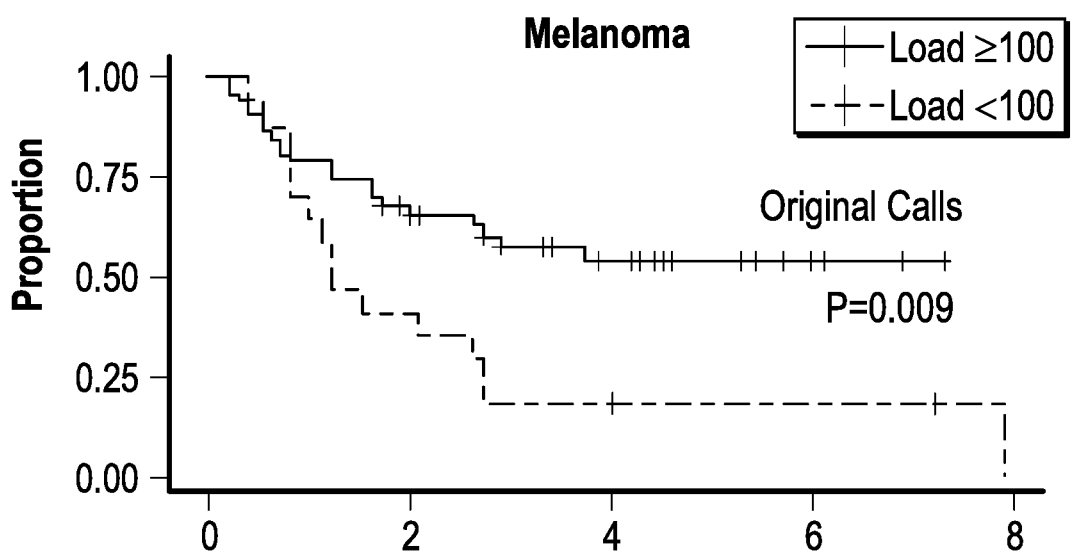
FIG. 30A

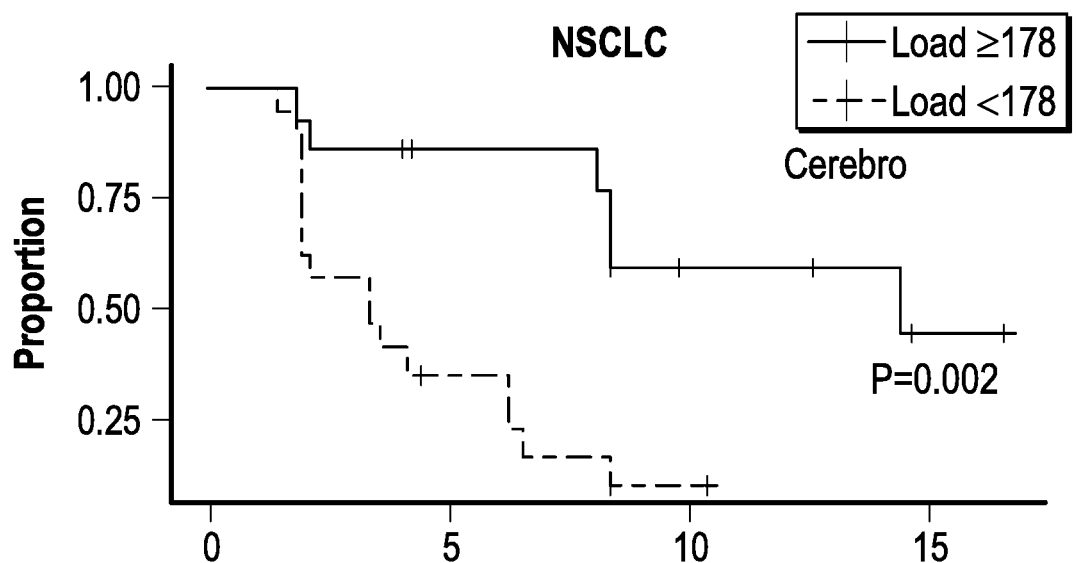
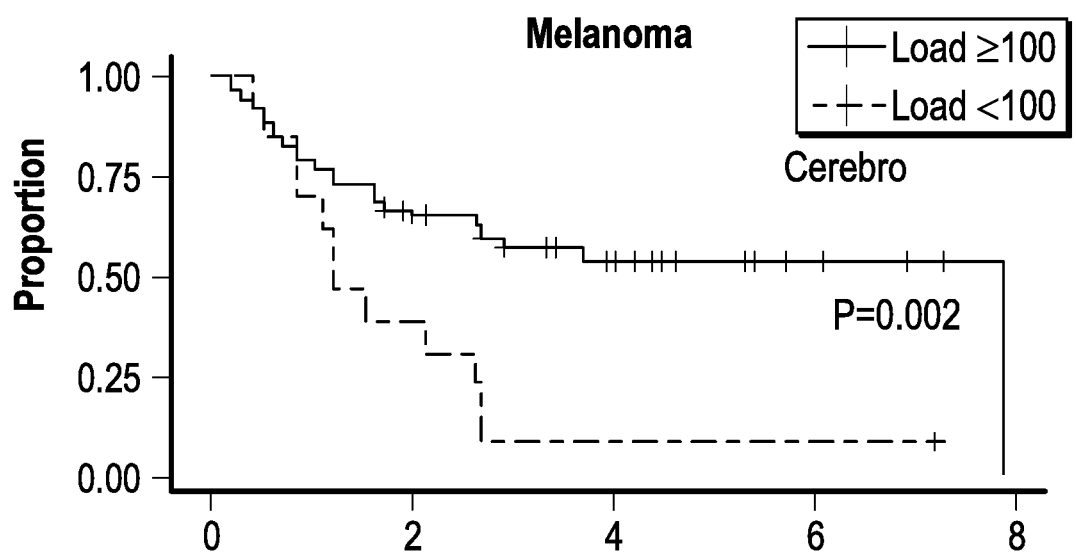
FIG. 30C

MACHINE LEARNING SYSTEM AND METHOD FOR SOMATIC MUTATION DISCOVERY

CROSS-REFERENCE TO RELATED APPLICATIONS

This application claims the benefit under 35 USC § 119(e) to U.S. Application Ser. No. 62/726,877 filed Sep. 4, 2018 and to U.S. Application Ser. No. 62/607,007 filed Dec. 18, 2017. The disclosure of each of the prior applications is considered part of and is incorporated by reference in the disclosure of this application.

FIELD OF THE INVENTION

The disclosure relates to medical genetics.

BACKGROUND OF THE INVENTION

Next-generation sequencing (NGS) technologies can potentially sequence very large amounts of genetic information very rapidly. NGS instruments may be used to sequence human genes with medical significance to assist in understanding or diagnosing medical conditions with a genetic signature. However, NGS technologies are subject to some problematic limitations. For example, NGS instruments typically produce a very large number of very short reads. Because those sequence reads are so short, it is challenging to assemble those reads to reconstruct the subject's genome and that is especially the case where the clinical sample presents degraded nucleic acid, or a low quantity of target nucleic acid within a mixed sample of excess non-target nucleic acid.

One exemplary case in which a target nucleic acid of medical significance may be present among excess non-target DNA is circulating tumor DNA (ctDNA). When a tumor grows in a person's body, it is understood that small fragments of DNA from the tumor may be found circulating in the person's blood. That ctDNA carries information such as mutations and structural alterations specific to the tumor. However, ctDNA is but one component of the cell-free DNA found in person's blood. Cell-free DNA typically also includes a large amount of normal, non-tumor DNA from the person.

The presence of abundant normal DNA may interfere with finding sequence mutations or structural alterations. Such a change may function as a driver mutation, implicated in oncogenesis because it confers a growth advantage on the cancer cell. As such, it would be medically useful to reliably detect and describe such mutations. Unfortunately, due to the relatively small fraction of ctDNA among cfDNA, and due to the very short sequence reads of NGS technologies, NGS may not reliably detect and describe medically significant alterations in ctDNA.

SUMMARY OF THE INVENTION

According to the disclosure, a computer is trained to recognize sequence mutations or structural alterations from sequence reads. The computer may compare the sequence reads to a reference and, if indicia of a sequence mutation or structural alteration are present, a machine learning algorithm validates that the sequence mutation or structural alteration has been detected. The machine learning algorithm is trained on a training data set that includes sequence reads and known sequence mutations and/or structural alterations. By using the trained machine learning algorithm, the computer can analyze sequence reads from a target nucleic acid and will reliably report when the nucleic acid has a sequence mutation or structural alteration. The machine learning algorithm allows for the detection of sequence mutations or structural alterations when using samples or sequencing technologies that otherwise make such detection difficult.

Systems and methods of the disclosure are particularly useful for detecting sequence mutations or structural alterations in tumor DNA, even when using NGS technologies. NGS sequence reads from tumor DNA are compared to a reference. Where the comparison shows a potential substitution, indel, or rearrangement in the tumor DNA, a machine learning classifier classifies that potential rearrangement as true or a product of experimental noise. The machine learning classifier, such as a random forest or neural network, is trained on training data that includes known sequence mutations or chromosomal rearrangements. The trained classifier can accurately determine when NGS sequence reads reveal a sequence mutation or structural alteration in a sample. Methods of the disclosure are useful to describe a variety of a complex mutations of distinct types, and may be applied to report genetic information about a tumor when sequencing ctDNA. Sequence reads from a sample are analyzed against a reference and the classification model provides for the detection and accurate reporting of sequence mutations or structural alterations and may be used to report the type, location, or boundaries of such changes.

Using methods of the disclosure, tumor genetics may be analyzed and reported from circulating tumor DNA (ctDNA) obtained from a blood or plasma sample. Methods are useful to describe tumor-specific rearrangements and alterations even using NGS sequencing on ctDNA in a plasma sample. Thus methods described herein provide a minimally-invasive tool for detecting tumors and monitoring progression or remission.

The classifier can operate within a variant calling pipeline and allow that pipeline to identify tumor-specific mutations, even where a sample may contain a mixture of tumor and normal DNA. The variant calling pipeline can further identify other mutation types such as small indels and substitution mutations. Systems and methods of the disclosure are useful for analyzing ctDNA in plasma samples, and can be used to monitor tumor progression, remission, or treatment.

In certain aspects, the disclosure provides a method for analyzing nucleic acid. The method includes sequencing nucleic acid from a sample from a subject to produce sequence reads and describing a mutation or structural alteration in the nucleic acid using a classification model trained to recognize the structural alteration. Preferably, the nucleic acid is DNA from a tumor, and the method further comprises providing a report that describes the DNA from the tumor as including the mutation or structural alteration. Describing the mutation or structural alteration may include comparing the sequence reads to a reference to detect an indicia of the mutation or structural alteration and validating the mutation or structural alteration as present in the nucleic acid using the classification model. The classification model may be trained on a training data set of sequences that include known mutations and/or structural alterations.

Methods may include training the classification model by providing the training data set to the classification model and optimizing parameters of the classification model until the classification model produces output describing the known mutations or structural alterations.

The classification model may include a neural network, a random forest, Bayesian classifier, logistic regression, decision tree, gradient-boosted tree, multilayer perceptron, one-vs-rest, or Naive Bayes. In certain embodiments, the classification model includes a random forest, e.g., that includes at least about one thousand decision trees. The decision trees optionally receive parameters such as sample type; FASTQ quality score; alignment score; read coverage; or estimated probability of error. In some embodiments, the classification model includes a neural network.

The method may include testing the trained classification model on a test data set of test sequences (e.g., obtained by Sanger sequencing) that include known test mutations (e.g., SNVs) and/or chromosomal rearrangements. Optionally, the training data set includes a plurality of known single-nucleotide variants (SNVs) and the method includes detecting at least one SNV in the nucleic acid; validating the detected SNV as present in the nucleic acid using the classification model; and providing a report that describes the nucleic as including the structural alteration and/or the SNV.

In some embodiments, the nucleic acid from the subject is tumor DNA and the sequence reads are tumor sequence reads and the method also includes sequencing normal DNA from the subject to produce normal sequence reads. The reference may include the normal sequence reads. Optionally, the sample includes plasma from the subject and the nucleic acid that is sequenced is cell-free DNA (cfDNA). The cfDNA may include circulating tumor DNA (ctDNA).

Where a structural alteration is found, detecting the structural alteration may include detecting at least one boundary of the structural alteration by either (a) or (b): (a) sequencing a fragment of the nucleic acid by paired-end sequencing to obtain a pair of paired-end reads, and mapping the pair of paired end reads to the reference, wherein when the pair of paired-end reads exhibit a discordant mapping to the reference, the fragment includes the boundary; and (b) sequencing the nucleic acid to determine a plurality of sequence tags, mapping the tags to the reference, and determining tag densities of mapped tags along portions of the reference, wherein when a portion of the reference exhibits an anomalous tag density a large indel is detected in a corresponding portion of the nucleic acid from the subject, wherein an end of the indel corresponds to the boundary of the structural alteration.

In other aspects, the disclosure provides a system for analyzing a tumor. The system includes a sequencing instrument for sequencing DNA from a sample from a subject to produce sequence reads, as well as a computer comprising a processor coupled to non-transitory memory.

The computer compares the sequence reads to a reference to detect a mutation or structural alteration, and validates the detected mutation or alteration as present in the DNA using a classification model. The classification model has been trained on a training data set. The training data set is a set of sequences that include known mutations or structural alterations. The system provides a report that describes the DNA from the subject as including the detected mutation or structural alteration. The system may include any suitable classification model, and it may be trained e.g., by providing the training data set to the classification model and optimizing parameters of the classification model until the classification model produces output describing the known mutation or structural alterations. Any suitable classification model may be used such as, for example, a neural network, a random forest, Bayesian classifier, logistic regression, decision tree, gradient-boosted tree, multilayer perceptron, one-vs-rest, or a Naïve Bayes operation. In certain embodiments, the classification model includes a random forest, e.g., with at least about 1,000 decision trees. The decision trees may receive parameters such as one or any combination of sample type, FASTQ quality score, alignment score, read coverage, and an estimated probability of error.

In some embodiments, the classification model includes a neural network. The neural network may be, for example, a deep-learning neural network with multiple (e.g., 5 or more) layers, which may include an input layer, a plurality of hidden layers, and an output layer. The trained classification model may optionally be tested on a test data set of test sequences (e.g., obtained by Sanger sequencing) that include known test chromosomal rearrangements. Sanger sequences for the test data may be preferred as Sanger sequencing may be understood to provide what is sometimes called a gold standard result.

In certain embodiments, the system detects and reports both structural alterations and small mutations such as single nucleotide variants (SNVs) and small indels. The training data set may include a plurality of known single-nucleotide variants (SNVs) (and/or small indels), and the method may include detecting at least one SNV in the DNA and validating the detected SNV as present in the DNA using the classification model. Preferably, the report then describes the DNA as including the SNV.

Methods and systems of the disclosure may be used for tumor/matched normal analyses. The DNA from the subject may be tumor DNA such that the sequence reads are tumor sequence reads and the method may also include sequencing normal DNA from the subject to produce normal sequence reads. Thus, the reference may include the normal sequence reads. Thus the structural alteration may be detected, validated, and reported in the subject's tumor DNA relative to that subjects normal, healthy DNA.

BRIEF DESCRIPTION OF THE DRAWINGS

FIG. 8 shows a report produced by methods and systems of the disclosure.

FIG. 21 is a Kaplan-Meier analysis of progression free survival (left) or overall survival (right) using tumor mutation loads from original publications.

FIG. 23 is Table 1 showing whole exome sequencing analysis and somatic mutations loads.

FIG. 24 is Table 2 showing a comparison of NGS clinical sequencing.

FIGS. 30A-30D illustrate comparison of Cerebro mutation calls with published calls.

DETAILED DESCRIPTION OF ONE OR MORE EMBODIMENTS

Figure 1:
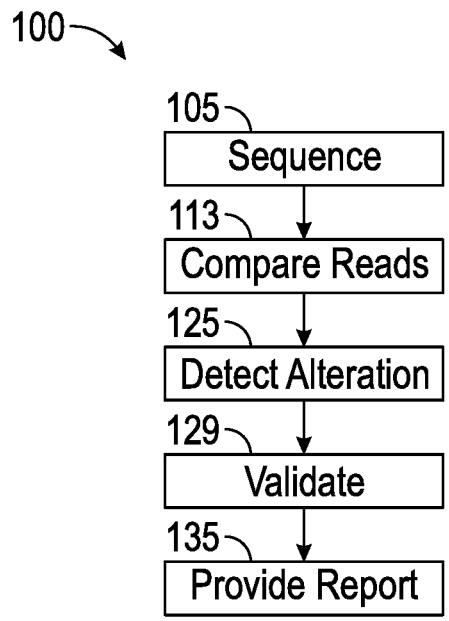
FIG. 1 diagrams a method 101 for analyzing nucleic acid.

FIG. 1 diagrams a method 101 for analyzing nucleic acid. The method 101 includes sequencing 105 nucleic acid from a sample from a subject to produce sequence reads and comparing 113 the sequence reads to a reference to detect 125 at least one mutation or boundary of a structural alteration. The method 101 further includes validating 129 the mutation or detected boundary as present in the nucleic acid using a classification model trained on a training data set of sequences that include known mutations and/or structural alterations. A report is provided 135 that describes the nucleic acid from the subject as including the mutation or structural alteration.

Systems and methods of the invention may be used for biomarker discovery, NGS research and development, to identify biomarker targets for a drug discovery pipeline, or to provide larger, multi-analyte panels in tissue and plasma including whole exome sequencing and neoantigen prediction. Systems and methods may be used clinically, for tumor analysis, or may have applications for clinical trial services, e.g., to prospectively stratify patients for clinical trials. Systems and methods of the disclosure may be deployed in a decentralized oncology testing system and may be deployed to beneficially use a pre-existing installed base of sequencing technology. Systems and methods may have particular applicability for in vitro diagnostic (IVD) pipelines and particularly for reporting mutations and rearrangements in panels of genes known to be associated with cancer.

In some embodiments, methods of the invention are implemented via a system of components that may optionally include one or more of a sample kit, sequencing tools, and analysis tools. For examples, an assay may start with extracted DNA from tissue or plasma, which may be extracted using a reagent kit (e.g., tubes and DNA extraction reagents, etc.). The kit may include tools for library preparation such as probes for hybrid capture as well as any useful reagents & protocols for fragmentation, adapter ligation, purification/isolation, etc. Such kits may have particular applicability in IVD applications. Using kits or other techniques known in the art a sample containing DNA is obtained.

For method 101, the sample that includes nucleic acid may be obtained 105 by any suitable method. The sample may be obtained from a tissue or body fluid that is obtained in any clinically acceptable manner Body fluids may include mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. Samples of particular interest include sputum and stool, where target nucleic acid may be severely degraded, or present in only very small amounts. A sample also may be media containing cells or biological material. Samples may also be obtained from the environment (e.g., air, agricultural, water and soil) or may include research samples (e.g., products of a nucleic acid amplification reaction, or purified genomic DNA, RNA, proteins, etc.). In preferred embodiments, a sample is a blood or plasma sample from a patient.

In some embodiments, methods of the invention are used in the analysis of circulating tumor DNA (ctDNA). Target ctDNA may be obtained by any suitable methods. In some embodiments, cell-free DNA is captured by hybrid capture. Exemplary hybrid capture based ctDNA workflow may include sample preparation, sequencing, and analysis. For sample prep, cell-free DNA may optionally be fragmented and barcoded to create a cell-free DNA library.

In certain embodiments, the method 101 includes obtaining 105 sequencing data from nucleic acid obtained from a tumor sample and a normal sample from the same patient. The tumor sample may be a biopsy specimen, or may be obtained as circulating tumor DNA (ctDNA). The normal sample can be any bodily tissue or fluid containing nucleic acid that is considered to be cancer-free, such as lymphocytes, saliva, buccal cells, or other tissues and fluids.

Tumor samples may include, for example, cell-free nucleic acid (including DNA or RNA) or nucleic acid isolated from a tumor tissue sample such as biopsied tissue or formalin fixed paraffin embedded tissue (FFPE). Normal samples, in certain aspects, may include nucleic acid isolated from any non-tumor tissue of the patient, including, for example, patient lymphocytes or cells obtained via buccal swab. Cell-free nucleic acids may be fragments of DNA or ribonucleic acid (RNA) which are present in the blood stream of a patient. In a preferred embodiment, the circulating cell-free nucleic acid is one or more fragments of DNA obtained from the plasma or serum of the patient.

The cell-free nucleic acid may be isolated according to techniques known in the art and may include, for example: the QIAmp system from Qiagen (Venlo, Netherlands); the Triton/Heat/Phenol protocol (THP); a blunt-end ligation-mediated whole genome amplification (BL-WGA); or the NucleoSpin system from Macherey-Nagel, GmbH & Co. KG (Duren, Germany) See Xue, 2009, Optimizing the yield and utility of circulating cell-free DNA from plasma and serum, Clin Chim Acta 404(2):100-104, and Li, 2006, Whole genome amplification of plasma-circulating DNA enables expanded screening for allelic imbalances in plasma, J Mol Diag 8(1):22-30, both incorporated by reference. In an exemplary embodiment, a blood sample is obtained from the patient and the plasma is isolated by centrifugation. The circulating cell-free nucleic acid may then be isolated by any of the techniques above.

According to certain embodiments, nucleic acid may be extracted from tumor or non-tumor patient tissues. After tissue or cells have been obtained from the patient, it is preferable to lyse cells in order to isolate nucleic acids. Lysing methods are known in the art and may include sonication, freezing, boiling, exposure to detergents, or exposure to alkali or acidic conditions.

When there is an insufficient amount of nucleic acid for analysis, a common technique used to increase the amount by amplifying the nucleic acid. Amplification refers to production of additional copies of a nucleic acid sequence and is generally carried out using polymerase chain reaction or other technologies well known in the art (e.g., Dieffenbach and Dveksler, PCR Primer, a Laboratory Manual, 1995, Cold Spring Harbor Press, Plainview, N.Y.).

Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and length of the primer pairs yield the desired melting temperature. The simplest equation for determining the melting temperature of primers smaller than 25 base pairs is the Wallace Rule ($Td=2(A+T)+4(G+C)$). Computer programs can also be used to design primers, including but not limited to Array Designer Software from Arrayit Corporation (Sunnyvale, CA), Oligonucleotide Probe Sequence Design Software for Genetic Analysis from Olympus Optical Co., Ltd. (Tokyo, Japan), NetPrimer, and DNAsis Max v3.0 from Hitachi Solutions America, Ltd. (South San Francisco, CA). The melting temperature of each primer is calculated using software programs such as OligoAnalyzer 3.1, available on the web site of Integrated DNA Technologies, Inc. (Coralville, IA).

Amplification and/or sequencing adapters may be attached to the fragmented nucleic acid. Adapters may be commercially obtained, such as from Integrated DNA Technologies (Coralville, IA). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, MA). Methods for using ligases are well known in the art. The polymerase may be any enzyme capable of adding nucleotides to the 3' and the 5' terminus of template nucleic acid molecules.

The input sample that is sequenced 105 may include entire genomes, chromosomes, or genes, or at least substantial portions thereof. A whole-genome assay might be desirable where the patient has an unknown cancer and a broad approach is necessary to pinpoint the mutations present. When tumor nucleic acid is isolated from ctDNA, and the type or location of the tumor is otherwise unknown, it may be desirable to analyze the whole genome. The mutations in the ctDNA can potentially include mutations from many tumors in the body, so performing a broad analysis on ctDNA will give a more complete picture of the progression of cancer in the body.

In some embodiments, a panel (e.g., tens or hundreds) of known cancer-related genes may be assayed. A panel may cover a range of genes of biological and clinical importance in human cancer. Some of the types of cancer covered by this panel are breast cancer, colorectal cancer, leukemia, prostate cancer and lymphoma. Assaying a whole genome or a panel of genes may include screening for alterations such as copy number variation, translocations, large indels, or inversions.

The nucleic acids can be sequenced 105 using any sequencing platform known in the art. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, CT), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized).

Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, CA). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, CA). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Other suitable sequencing technologies may include single molecule, real-time (SMRT) technology of Pacific Biosciences (in SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW) where the fluorescent label is excited and produces a fluorescent signal, and the fluorescent tag is cleaved off. Detection of the corresponding fluorescence of the dye indicates which base was incorporated); nanopore sequencing (DNA is passed through a nanopore and each base is determined by changes in current across the pore, as described in Soni & Meller, 2007, Progress toward ultrafast DNA sequence using solid-state nanopores, ClinChem 53(11):1996-2001); chemical-sensitive field effect transistor (chemFET) array sequencing (e.g., as described in U.S. Pub. 2009/0026082); and electron microscope sequencing (as described, for example, by Moudrianakis, E. N. and Beer M., in Base sequence determination in nucleic acids with the electron microscope, III. Chemistry and microscopy of guanine-labeled DNA, PNAS 53:564-71 (1965).

Sequencing according to embodiments of the invention generates a plurality of reads. Reads according to the invention generally include sequences of nucleotide data less than about 150 bases in length, or less than about 90 bases in length. In certain embodiments, reads are between about 80 and about 90 bases, e.g., about 85 bases in length. In some embodiments, methods of the invention are applied to very short reads, i.e., less than about 50 or about 30 bases in length. Sequence read data can include the sequence data as well as meta information.

Sequence read data can be stored in any suitable file format including, for example, VCF files, FASTA files or FASTQ files, as are known to those of skill in the art. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

Certain embodiments of the invention provide for the assembly of sequence reads. In assembly by alignment, for example, the reads are aligned to each other or to a reference. By aligning each read, in turn to a reference genome, all of the reads are positioned in relationship to each other to create the assembly. In addition, comparing 113 the sequence read to a reference sequence by, e.g., aligning or mapping, can also be used to identify variant sequences within the sequence read. In some embodiments, reads are aligned (e.g., to a reference) using Burrows-Wheeler Transform (BWT), which includes indexing the reference. A read is aligned to the reference using, for example, Burrow-Wheeler Aligner (BWA), e.g., using bwa-short to align each read to a reference, and the output can be a Binary Alignment Map (BAM) including, for example, a CIGAR string.

Computer programs for assembling reads are known in the art. Assembly can be implemented, for example, by the program 'The Short Sequence Assembly by k-mer search and 3' read Extension' (SSAKE), from Canada's Michael Smith Genome Sciences Centre (Vancouver, B.C., CA) (see, e.g., Warren et al., 2007, Assembling millions of short DNA sequences using SSAKE, Bioinformatics, 23:500-501). SSAKE cycles through a table of reads and searches a prefix tree for the longest possible overlap between any two sequences. SSAKE clusters reads into contigs. Other read assembly programs include: Forge Genome Assembler (see, e.g., DiGuistini et al., 2009, De novo sequence assembly of a filamentous fungus using Sanger, 454 and Illumina sequence data, Genome Biology, 10:R94); ABySS (Simpson et al., 2009, ABySS: A parallel assembler for short read sequence data, Genome Res., 19(6):1117-23).

In some embodiments, read assembly uses Roche's GS De Novo Assembler, known as gsAssembler or Newbler (NEW assemBLER), which is designed to assemble reads from the Roche 454 sequencer (described, e.g., in Kumar & Blaxter, 2010, Comparing de novo assemblers for 454 transcriptome data, Genomics 11:571 and Margulies 2005). Newbler accepts 454 Flx Standard reads and 454 Titanium reads as well as single and paired-end reads and optionally Sanger reads. Newbler can be accessed via a command-line or a Java-based GUI interface.

The sequence data, in the form of the sequence reads themselves, or the product of read assembly such as a contig or consensus sequence, may be analyzed by comparison 113 to a reference. Comparing sequence data to a reference may include any suitable method such as alignment. For example, individual sequence reads may be aligned, or "mapped", to a reference, or sequence reads may be assembled and then aligned. Any suitable reference may be used including, for example, a published human genome (e.g., hg18 or hg36), sequence data from sequencing a related sample, such as a patient's non-tumor DNA, or some other reference material, such as "gold standard" sequences obtained by, e.g., Sanger sequencing of subject nucleic acid.

Comparing 113 sequence data to a reference allows for the identification of mutations or variants. Using techniques of the disclosure, substitutions, small indels, and larger alterations such as rearrangements, copy number variation, and microsatellite instability can be determined. In certain preferred embodiments, the sequence data is from tumor DNA and is compared 113 to a non-tumor reference (such as sequence data from the same patient's non-tumor DNA) to identify mutations and variants. The analysis can include the identification of a variety of chromosomal alterations (rearrangements, amplifications, or microsatellite instability) with detection 125 of a boundary of such an alteration as well optionally sequence mutations (single base substitutions and small indels).

The output of comparing sequence data to a reference may be any suitable output or any suitable format. The output can be provided in the format of a computer file. In certain embodiments, the output is a FASTA file, FASTQ file, or VCF file. Output may be processed to produce a text file, or an XML file containing sequence data. Other formats include Simple UnGapped Alignment Report (SUGAR), Verbose Useful Labeled Gapped Alignment Report (VUL-GAR), and Compact Idiosyncratic Gapped Alignment Report (CIGAR) (Ning, Z., et al., Genome Research 11(10): 1725-9 (2001)). In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9).

Figure 2:
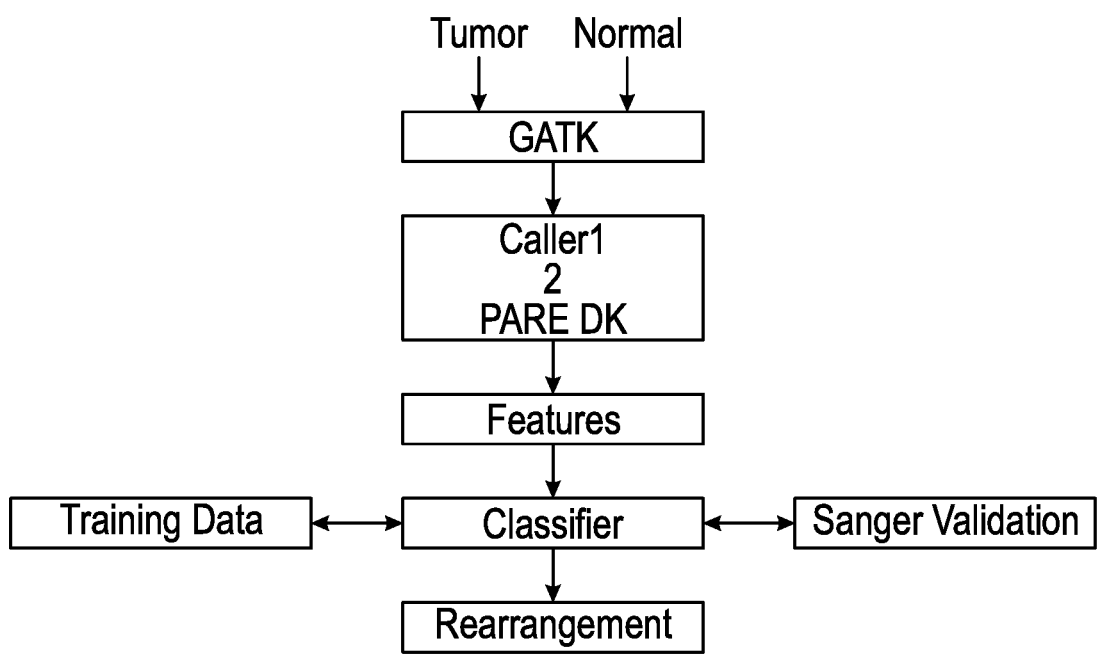
FIG. 2 diagrams the workflow for sequence analysis.

FIG. 2 diagrams the workflow for sequence analysis. Sequence data including either or both of tumor and matched normal sequence data from a patient are obtained as described above. That sequence data is compared 113 to a reference. Such a comparison may include alignment to the reference and may be implemented using a known tool such as the Genome Analysis Toolkit (GATK), BWA, or others. A tool, or caller, is then used to identify 125 at least one rearrangement or alteration within the sequence data. In fact, multiple alterations and mutations may be identified, and each type of mutation or alteration may be identified using a dedicated tool or caller to, e.g., implement any of the techniques described below.

Analysis includes using a caller tool to identify at least one alteration—specifically, to detect 125 at least one boundary of an alteration or rearrangement. The processes of identifying rearrangements, alterations, and mutations also gives a number of outputs, referred to here as features, that are used as inputs to the classification model. Features include all manner of output from the sequencing, analysis, and variant calling pipelines. For example, features may include the FASTQ quality score for any given base in the sequence data. In preferred embodiments, features include at least one instance of a confidence score, or probability score, that is output by the variant caller when a variant is identified.

At least one caller within the workflow is used in the detection 125 of a mutation or boundary of a structural alteration. In some embodiments, the output of that caller tool describes a rearrangement in the DNA from the sample, relative to the reference. For example, the caller may pass a genomic coordinate, stating that the coordinate represents the boundary of an inversion or translocation. Different tools may be used (any one or more of them) to identify one or a plurality of different rearrangement boundaries. Any suitable technique may be used to detect 125 the structural alteration.

For example, a boundary of a structural alteration may be detected 125 by a personalized analysis of rearranged ends (PARE). In some embodiments, detecting 125 the boundary includes sequencing a fragment of the DNA by paired-end sequencing to obtain a pair of paired-end reads, and mapping the pair of paired end reads to the reference. Here, when the pair of paired-end reads exhibit a discordant mapping to the reference, the fragment includes the boundary. For additional detail, see U.S. Pub. 2015/0344970, incorporated by reference.

Embodiments of PARE provide for the identification of patient-specific rearrangements in tumor samples. In preferred embodiments, PARE includes the analysis of mate-paired tags. Genomic DNA from a sample is purified, sheared and used to generate libraries with mate-paired tags (e.g., about 1.4 kb apart). Libraries may be digitally amplified by emulsion polymerase chain reaction (PCR) on magnetic beads and 25 bp mate-paired tags are sequenced (e.g., using sequencing-by-ligation of McKernan, 2009, Genome Res 19:1527-1541, incorporated by reference). About 200 million 25 base reads may be obtained for each sample where each read aligns perfectly and is uniquely localized in the reference human genome (e.g., hg18). Typically, tens of millions of mate-paired reads in which both tags map perfectly to the reference will be obtained. Mate-paired tags mapping the reference genome uniquely and without mismatches are analyzed for aberrant mate-pair spacing, orientation and ordering. Mate pairs mapping to the same chromosome at appropriate distances (about 1.4 kb) and in the appropriate orientation and ordering are considered concordant. Discordant mate pairs are candidates for finding alterations, such as rearrangements and/or copy number alterations. Various approaches may use PARE data to show alteration or rearrangement boundaries. One approach involves searching for tags whose mate-pairs map to different chromosomes, indicating inter-chromosomal rearrangements or translocations.

Figure 3:
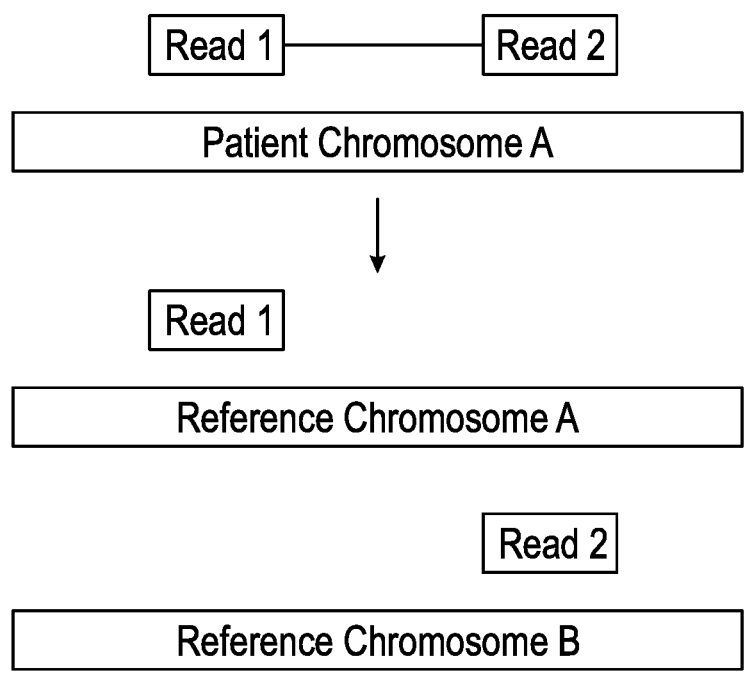
FIG. 3 illustrates detecting a translocation from mate-pair tags.

FIG. 3 illustrates detecting a translocation from mate-pair tags. Mate pair tags from one fragment of patient DNA, in which the tags map to different chromosomes of the reference. The high physical coverage of breakpoints provided by the about 40 million mate-paired sequences per sample suggest that a large fraction of such translocations can be identified. End sequences from such mate-paired tags maybe grouped into 1 kb bins and those bin pairs that are observed at least 5 times are analyzed further. The requirement for at least 5 occurrences minimized the chance that the presumptive fusion sequences represent incorrect mapping to the reference genome or artifacts of library construction. Finding multiple mate-pairs proximal to each other that both map to the different chromosomes can not only ensure that a translocation has been detected but can also allow one to precisely locate the boundary of the break and give a numerical genomic coordinate for the boundary (between the 3' and 5' most-proximal mates). Another approach looks for mate pair tags to identify such pairs in which one member of the pair has a different copy number than the other.

For identification of candidate rearrangements associated with copy number alterations, a 10 kb boundary region of amplifications, homozygous deletions, or lower copy gains and losses is analyzed for neighboring discordant mate pair tags observed at least about 2 times in the tumor but not matched normal sample.

In certain embodiments, detecting 125 the boundary includes sequencing the DNA to determine a plurality of sequence tags, mapping the tags to the reference, and determining tag densities of mapped tags along portions of the reference in a process that may be referred to as digital karyotyping (DK). The DK techniques may be used within the PARE analyses discussed above, or may be used as described below on their own. In this technique, where a portion of the reference exhibits an anomalous tag density, an indel is detected in a corresponding portion of the DNA from the subject. An end (i.e., a terminus or boundary) of the indel corresponds to the boundary of the structural alteration. For additional detail, see U.S. Pat. No. 7,704,687, incorporated by reference.

Figure 4:
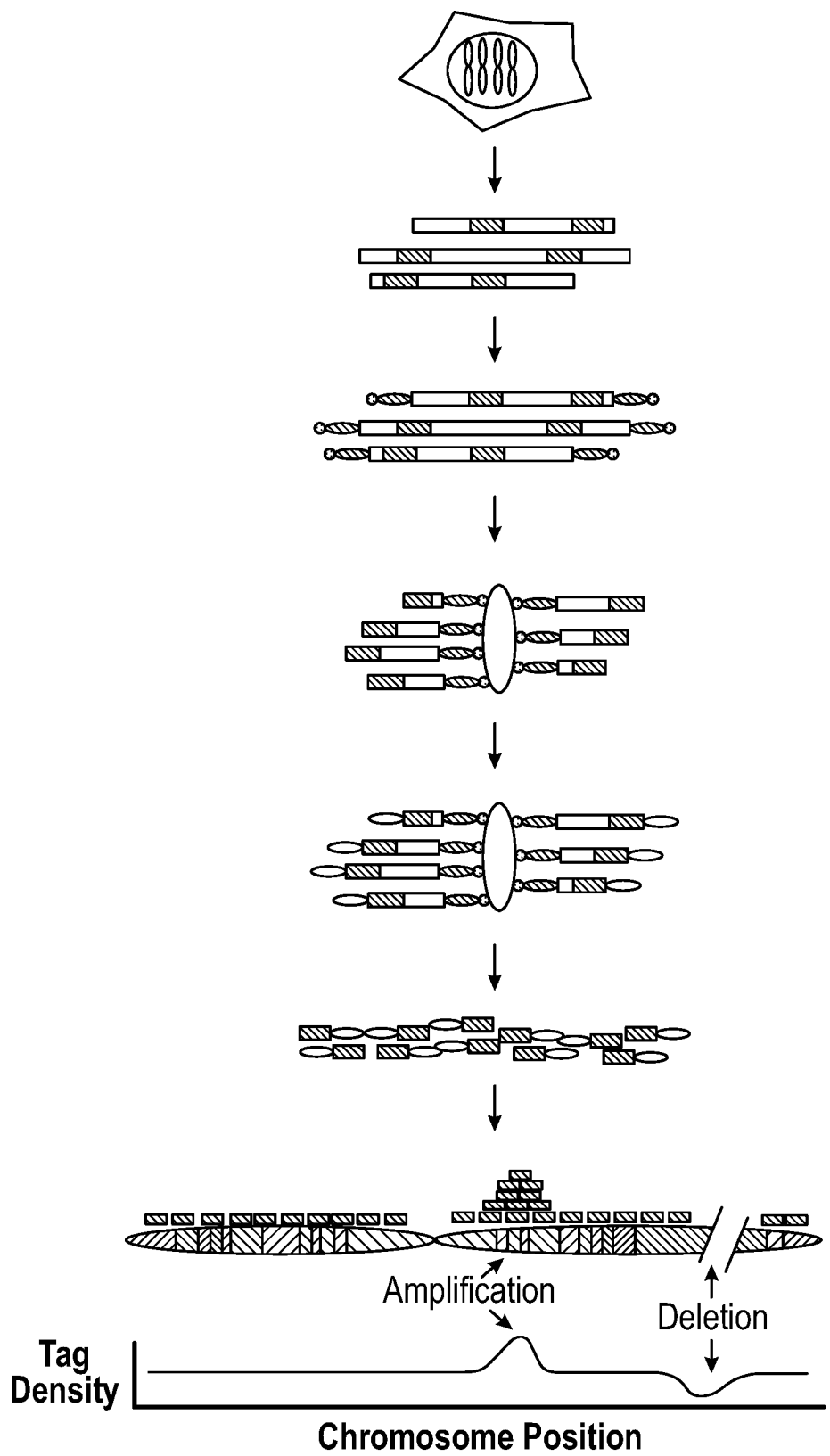
FIG. 4 illustrates output from use of digital karyotyping to detect an alteration boundary.

FIG. 4 illustrates output from a DK approach. For digital karyotyping, DNA is cleaved with a restriction endonuclease (mapping enzyme) that is predicted to cleave genomic DNA into several hundred thousand pieces, each on average <10 kb in size (Step 1). A variety of different endonucleases can be used for this purpose, and certain embodiments use SacI, with a 6-bp recognition sequence predicted to preferentially cleave near or within transcribed genes.

Biotinylated linkers are ligated to the DNA molecules (Step 2) and then digested with a second endonuclease (fragmenting enzyme) that recognizes 4-bp sequences (Step 3). As there are on average 16 fragmenting enzyme sites between every two mapping enzyme sites, the majority of DNA molecules in the template are expected to be cleaved by both enzymes and thereby be available for subsequent steps. DNA fragments containing biotinylated linkers are separated from the remaining fragments using streptavidin-coated magnetic beads (Step 3). New linkers, containing a 5-bp site recognized by MmeI, a type IIS restriction endonuclease, are ligated to the captured DNA (Step 4). The captured fragments are cleaved by MmeI, releasing 21 bp tags (Step 5). Each tag is thus derived from the sequence adjacent to the fragmenting enzyme site that is closest to the nearest mapping enzyme site. Isolated tags are self-ligated to form ditags, PCR amplified en masse, concatenated, cloned, and sequenced (Step 6). As described for SAGE (Velculescu, 1995, Science 270:484-487, incorporated by reference), formation of ditags provides a robust method to eliminate potential PCR induced bias during the procedure. Current automated sequencing technologies identify up to 30 tags per concatamer clone, allowing for analysis of 100,000 tags per day using a single 384 capillary sequencing apparatus. Finally, tags are computationally extracted from sequence data, matched to precise chromosomal locations, and tag densities are evaluated over moving windows to detect abnormalities in DNA sequence content (Step 7).

Whether using PARE, DK, PARE with DK, or some other technique, one or more of the caller tools in the analysis pipeline may detect 125 a boundary of an alteration or rearrangement. The method 101 includes comparing 113 the sequence reads to a reference to detect 125 at least one boundary of a structural alteration. That "called boundary" is passed to a classification model that classifies the called boundary as true or not, i.e., validates 129 the detected boundary as present in the DNA from the sample. Thus, the method 101 includes validating 129 the detected boundary as present in the DNA using a classification model trained on a training data set of sequences that include known structural alterations.

Additionally or alternatively, one or more of the caller tools in the analysis pipeline may detect 125 a mutation (such as a small indel or a substitution (e.g., SNV)). The method 101 includes comparing 113 the sequence reads to a reference to detect 125 the mutation. That "called mutation" is passed to a classification model that classifies the called mutation as true or not, i.e., validates 129 the detected mutation as present in the DNA from the sample. Thus, the method 101 includes validating 129 the detected mutation as present in the DNA using a classification model trained on a training data set of sequences that include known mutations.

Methods may include training the classification model by providing the training data set to the classification model and optimizing parameters of the classification model until the classification model produces output describing the known mutations or structural alterations.

Any suitable classification model may be used such as, for example, a neural network, a random forest, Bayesian classifier, logistic regression, support vector machine, principal component analysis, decision tree, gradient-boosted tree, multilayer perceptron, one-vs-rest, and Naive Bayes.

Figure 5:
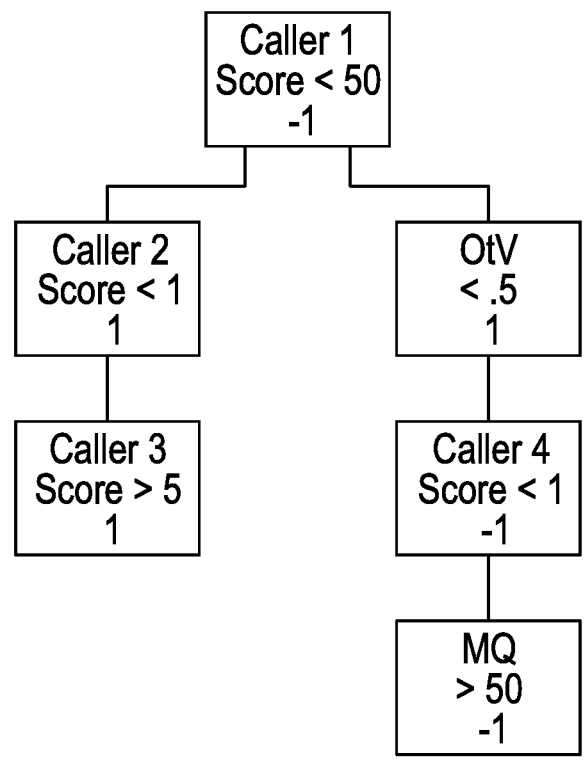
FIG. 5 illustrates a random forest classification model.

FIG. 5 illustrates a random forest classification model as may be implemented within a system of the invention. Random forests implement a plurality of decision trees, in which an input is entered at the top and as it traverses down the tree the data gets bucketed into smaller and smaller sets. The random forest combines, or forming an ensemble of, decision trees. Each tree contributes weekly to the classification, but as an ensemble, the forest is a strong classifier. A decision tree is a decision support tool that uses a tree-like graph or model of decisions and their possible consequences, including chance-event outcomes, resource costs, and utility. A decision tree embodies a number of yes/no questions that assess the probability that the detected mutation or boundary is true.

To train a random forest, for some number of trees T, a number N of cases are sampled at random with replacement to create a subset of the data. The subset may be, e.g., about 66% of the total set. At each node: (i) for some number m, m predictor variables are selected at random from all the predictor variables; (ii) the predictor variable that provides the best split, according to some objective function, is used to do a binary split on that node; and (iii) at the next node, choose another m variables at random from all predictor variables and do the same.

For a random forest, generally m<<number of predictor variables. When running a random forest, when a new input is entered into the system, it is run down all of the trees. The result may either be an average or weighted average of all of the terminal nodes that are reached. With a large number of predictors, the eligible predictor set will be quite different from node to node. As m goes down, both inter-tree correlation and the strength of individual trees go down.

So some optimal value of m is preferably discovered. Random forest runtimes are quite fast, and they are able to deal with unbalanced and missing data. The parameters that may be input into a random forest may include sample type; FASTQ quality score; alignment score; read coverage; and an estimated probability of error. The trained random performs forest classification and filtering of tumor specific alterations with confidence scoring. The trained model includes an ensemble of decision trees with different relative weights.

Random forests may be implemented in software such as de novo programs or a software package that performs operations described herein. One approach is implemented in the R package randomForest. Random forest classifiers are implemented by software packages such as ALGLIB, SQP, MatLab, and others. In certain preferred embodiments, the classification model is a random forest. In some embodiments, the classification model uses a neural network.

Figure 6:
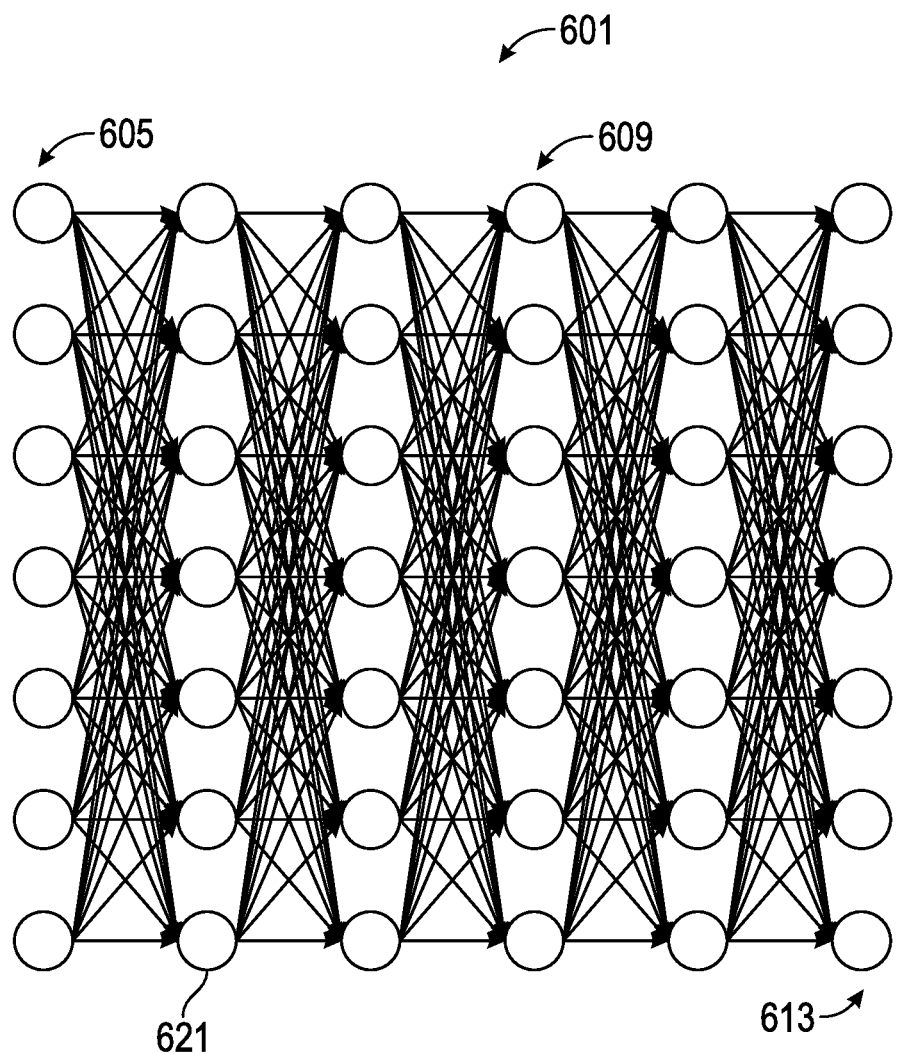
FIG. 6 illustrates a neural network.

FIG. 6 illustrates a neural network 601 as may be implemented within a system of the invention. Neural networks are machine-learning tools that learn (progressively improve performance) to do tasks by considering examples, generally without task-specific programming A neural network 601 typically includes a collection of connected units called artificial neurons or nodes 621. Each connection between nodes can transmit a signal to another node. The receiving node can process the signal(s) and then signal downstream nodes connected to it. Nodes may have state, generally represented by real numbers, typically between 0 and 1. Nodes and connections may also have a weight that varies as learning proceeds, which can increase or decrease the strength of the signal that it sends downstream. Further, they may have a threshold such that only if the aggregate signal is below (or above) that level is the downstream signal sent. Typically, nodes 621 are organized in layers 609. Different layers may perform different kinds of transformations on their inputs. Signals travel from the input layer 605, to the output layer 613, possibly after traversing the layers multiple times.

Embodiments of the invention implement a Naïve Bayes classification model. Naïve Bayes classifiers are a family of simple probabilistic classifiers based on applying Bayes' theorem with strong (naïve) independence assumptions between the features. The featured image is the equation—with P(A|B) is posterior probability, P(B |A) is likelihood, P(A) is class prior probability, and P(B) is predictor prior probability. In certain embodiments, logistic regression provides a classification model.

Logistic regression is a powerful statistical way of modeling a binomial outcome with one or more explanatory variables. It measures the relationship between the categorical dependent variable and one or more independent variables by estimating probabilities using a logistic function, which is the cumulative logistic distribution. Another suitable classification model uses support vector machines (SVM). SVM is binary classification algorithm. Given a set of points of 2 types in N dimensional space, SVM generates a (N-1) dimensional hyperplane to separate those points into 2 groups. Here, detected boundaries represent points in the space of input variables and an SVM may separate those points into true boundaries and experimental noise.

Principal Component Analysis (PCA) may be used as the classification model. PCA is a statistical procedure that uses an orthogonal transformation to convert a set of observations of possibly correlated variables into a set of values of linearly uncorrelated variables called principal components.

The role of the classification model includes validating 129 the genomic features that are identified by variant calling. In particular, the classification model validates 129 whether an identified boundary of a genomic alteration should be reported as "true", or present in the subject DNA.

To this end, the classification model may be trained on a training data set. The training data set may include various subcomponents. In some embodiments, the training data set includes at least three sub-component data sets: real world clinical data (e.g., obtained by NGS), gold standard data (e.g., as may be obtained by Sanger sequencing of test samples), and simulated data sets that may be used to present known hard-to-detect mutations and alterations to the variant calling pipeline.

In certain embodiments, the gold standard data set includes hundreds of millions of bases of whole exome Sanger sequencing. The gold standard dataset preferably includes tens of thousands of genomic rearrangements. This data set may include reference standards of millions of bases. In preferred embodiments, the gold standard data set includes at least a substantial portion of a human genome or chromosome (e.g., at least 50%) obtained by Sanger sequencing. Sanger reference data is known to have greater accuracy than next-generation sequencing data, and thus can be used to confirm the legitimacy of variations. The NGS sequencing reads of a patient's tumor sample, a patient's normal sample, or both may be filtered against a Sanger reference prior to being compared to each other to identify tumor-specific mutations. In some embodiments, sections of the NGS sequence from nucleic acid determined to contain a tumor-specific alteration through comparison to NGS sequencing reads of a patient's normal sample may subsequently be filtered against a Sanger sequencing reference in order to validate the mutation. Methods and systems of comparing next generation sequence reads with a Sanger sequencing reference are described in U.S. Pub. 2016/0273049, incorporated by reference.

Real world clinical data may be included in the training data. Any suitable real-world clinical data may be included. In preferred embodiments, the real-world clinical data includes results from sequencing assays performed as described herein. For example, the real-world clinical data of the training data set may include sequences derived from NGS analysis of ctDNA such as the results of generating millions of short reads by sequencing prior test nucleic acid, mapping the reads to a reference, and calling mutations and alteration from the mapping results, in which the real-world clinical data further includes at least one known alteration in the prior test nucleic acid relative to a reference such as hg18 or hg37. Preferably, the real-world clinical data includes the known alterations and mutations as provided by the expert curation of tumor genomes. In a most preferred embodiment, the real-world clinical data includes data from thousands of clinical tumors and also includes alterations and mutation calls made by the expert curation of those tumors.

Simulations may form an important component of the training data set. Simulation data may include any kind of in silico data formatted like clinical and/or gold standard data. Simulated data may be generated de novo or may be generated by modifying another clinical data set to include simulated features. Simulated data may include one or any combination of simulated features such as simulated mutations or alterations, simulated copy number variants, simulated micro-satellite instability, simulations of tumor clonality, or simulated degrees of tumor mutation burden, to name but a few. In preferred embodiments, the simulated data includes more than one billion bases of clinical genomes with simulated mutant spike-ins (i.e., added into the data in an in silico fashion), and preferably includes at least one alteration, relative to a reference, such as an indel, an inversion, a translocation, a duplication, aneuploidy, or a copy number variant.

The training data is used to train the classification model and also to validate that the trained classification model will perform reliably when presented with data not yet presented to the classification model. Thus, for example, a neural network may be provided with the real-world clinical data (the sequences and the known variants). The neural network assigns weights across neurons, observes differences between the network outputs and the known results (e.g., the variants called by expert curation over thousands of tumor samples). The neural network adjusts those weights until the network output converge on the known results. The simulated data may then be used to present the neural network with known, or suspected to be, difficult-to-detect mutations types such as clusters of small indels, or single nucleotide variants only a few bases away from indels. Once the neural network is trained, the ability of the neural network to call variants may be validated using the gold standard data. In fact, it should be appreciated that the gold standard data may be used to validate the entire variant calling pipeline or any step therein. In some embodiments, before the neural network is deployed clinically, the gold standard data is provided. Any deviation from the correct result is addressed. For examples, miss-calls by the neural network are back-propagated through the network to improve its calling. Whatever classification model is used, the classification model is used for validating a detected mutation or boundary as present in the nucleic acid.

Thus, embodiments of the invention employ machine learning whereby a training set with ground truth is provided to the machine-learning algorithm to create an adaptively boosted classifier. The classifier is applied to a target set to create a high-confidence rearrangement call set.

Analytical pipelines of the invention generate high quality data to maximize the accuracy of sequencing results. Sequencing results include quality scores. Minimum values or ideal ranges for high quality data may be implemented as a pass-through criterion within the pipeline. Each metric may be marked as pass or fail. For NGS, base calls are given a probability score on how likely the base called is truly the base of the DNA. Quality scores indicate the probability of an incorrect base call and incorporated into the .bcl and .fastq formats. Quality scores are generated by a quality table that uses a set of quality predictor values. The quality table may be updated when characteristics of the sequencing platform change.

The classification model may be developed in any suitable environment, such as Python and Bash scripting languages. The model may use hardware parallelism to achieve the best performance. The classification model has relatively low resource requirements when compared to running the callers. Even for large data sets, training is on the order of minutes or hours using about 10 GB of memory.

Methods of the invention are used to detect and report 135 alterations such as large indels, inversions, copy number variants, or translocations. Methods may also include detecting and reporting mutations such as small indels and substitutions. In preferred embodiments, methods include detecting and reporting a number of single-nucleotide variants (SNVs).

Figure 7:
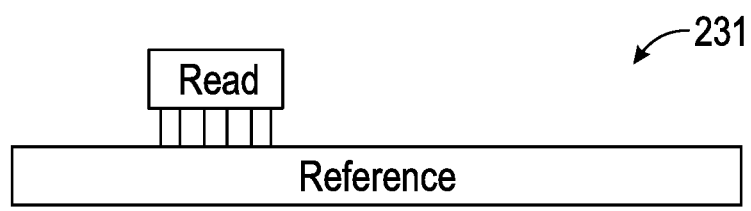
FIG. 7 illustrates calling a single nucleotide variant (SNV) by read-mapping.

FIG. 7 illustrates calling an SNV. Calling an SNV generally involves comparing a sequence read to a reference and reporting any variation between them. Somatic variant callers score and filter data from alignment to call true sequence mutations. Alignment identifies candidate sequence mutations. Specifically, in some embodiments, the pipelines described herein score candidate sequence mutations and filter to resolve conflicts. After alignment to a reference genome, the next step is variant calling. A program (e.g., a de novo software application) examines the mapped data and reference genome side-by-side to determine the existence of sequence mutations (single base changes and small indels). In some embodiments, the program extracts candidate variants from alignment, then scores a number of (e.g., approximately 50) individual metrics for each variant and applies these scores both individually and in combination to identify bona fide sequence mutations and to exclude sequence artifacts. Any suitable program may be used to call somatic mutations.

MuTect is a somatic SNV caller that applies a Bayesian classifier to detect somatic mutations. It is sensitive in detecting low variant allele frequency (VAF) somatic variants. It also incorporates a series of filters to penalize candidate variants that have characteristics corresponding to sequencing artifacts to increase precision. SomaticSniper applies a Bayesian model to detect genotype change between the normal and tumor tissues, taking into account the prior probability of somatic mutation. Another Bayesian approach is JointSNVMix2, which jointly analyses paired tumor—normal digital allelic count data and has very high sensitivity in many different settings, but tends to be lower in precision. Variants may be reported in any suitable format such as the variant call format (*.VCF; a standard tab-delimited format for storing variant calls).

It may be found that small changes (single base changes and indels) surrounded by wild-type sequence are relatively easy to align and call. Structural alterations as discussed above (large indels, Amplifications, Rearrangements) are highly variable between tumors and are not subject to predictable rules. As such, those structural alterations may be found to be difficult to align, detect, report, and describe.

Most somatic variant callers are not designed nor intended for analyzing tumor/normal pairs, and in such circumstances the trained classification model may allow for calling somatic variants between tumor/normal pairs that otherwise can't reliably be called with existing tools. Additionally, variant calling for tissue differs for plasma because of the depth of sequencing coverage needed for plasma.

Due to the significant difficulties that may be presented in calling variants from cell-free DNA from plasma, the use of the classification model may be the step that provides for reliable and clinically useful variant calling and in particular for calling boundaries of alterations. The classification model is trained using training data as described above.

Preferably, the training data set includes a plurality of known single-nucleotide variants (SNVs). Methods of the invention may include detecting at least one SNV in the DNA; and validating the detected SNV as present in the DNA using the classification model, wherein the report describes the DNA as including the SNV. Thus, methods described herein accurately filter critical scoring conflicts commonly found in the NGS data and provide for clinically useful variant calling.

Methods of the invention may target patient sequences known to relate to a disease or condition. For example, if the target nucleic acid includes ctDNA, then screening may cover genes associated with cancer. Genes known to be associated with a variety of cancers include ABL1, AKT1, AKT2, ALK, APC, AR, ARID1A, ARID1B, ASXL1, ATM, ATRX, BAP1, BRAF, BRCA1, BRCA2, CBL, CCND1, CCNE1, CDH1, CDK4, CDK6, CDKN2A, CEBPA, CREBBP, CTNNB1, DAXX, DNMT3A, EGFR, ERBB2, ERBB3, ERBB4, EZH2, FBX27, FGFR2, FGFR3, FGFR4, FLT3, FOXL2, GATA1, GATA2, GNA11, GNAQ, GNAS, HNF1A, HRAS, IDH1, IDH2, IGF1R, IGF2R, IKZF1, JAK1, JAK2, JAK3, KDR, KITKRAS, MAML1, MDM2, MDM4, MED12, MEN1, MET, MLH1, MLL, MPL, MSH2, MSH6, MYC, MYCN, MYD88, NF1, NF2, NOTCH1, NOTCH2, NOTCH3, NOTCH4, NPM1, NRAS, PALB2, PAXS, PBRM1, PDGFRA, PDGFRB, PIK3CA, PIK3R1, PMS2, PTCH1, PTEN, PTPN11, RB1, RET, RNF43, ROS1, RUNX1, SF3B1, SMAD2, SMAD3, SMAD4, SMARCB1, SMO, STAG2, STK11, TET2, TGFBR2, TNFAIP3, TP53, TSC1, TSC2, TSHR, VHL, and WT1a. Mutations in those genes may be used to diagnose, classify tumor subtypes, determine prognoses, monitor tumor progression, and establish appropriate therapies. Types of mutations identified using the systems and methods of the invention may include any type of mutation known in the art, including, for example, an insertion, a deletion, a copy number alteration, and/or a translocation.

The analytical pipeline described herein is preferably used to identify and validate the reporting of an alteration in sample nucleic acid relative to a reference. The pipeline workflow may start with, e.g., FASTQ files for both tumor and the matched normal sequencing reads, which may be processed using Genome Analysis Toolkit (GATK) to provide BAM files. Optionally, the calls along with the feature set is provided to the machine-learning model. After training, the model calculates the probability for each call, yielding a high-confidence somatic mutation call set.

There may be separate optimization of pipelines for mutation calling and alteration calling. In some embodiments, the mutation calling pipeline is trained using 300+ million bases of whole-exome Sanger sequences of matched tumor/normal pairs. The size and breadth of the Sanger dataset allows the pipeline to make accurate variant calls down to 2% MAF. It works well in difficult-to-analyze regions of the genome, such as GC-rich regions and highly repetitive regions. The alteration calling pipeline is preferably trained and tested on more than 10,000 suspected alterations such as indels, translocation, copy number variants, inversions, and fusions.

Whole genome translocation analysis of 200 matched T/N pairs is performed using a caller and a classification model trained on a large training data set. It is believed that the large training set allows the alteration-calling pipeline to have clinical utility to detect alterations in ctDNA by NGS. That is, it is understood that methods described herein are what allow for the detection of tumor-specific structural alterations by NGS from ctDNA. Those large structural variations (large indels, amplifications, rearrangements) are highly variable between tumors but nevertheless are important clinical targets in the management of cancer patients. Furthermore, those alterations are some of the most therapeutically targeted among FDA-approved indications (imatinib, crizotinib, trastuzumab, etc.). Thus methods of the invention may have particular utility in determining an effective course of treatment for a patient via a minimally invasive procedure (e.g., an assay from blood or plasma).

In particular, use of the classification model adds accuracy and reliability for clinical utility to alteration calling as described here. Embodiments of the disclosure detect alterations within ctDNA through techniques such as Paired Analysis Rearranged Ends (PARE) and Digital Karyotyping (DK). PARE Identifies rearrangements. Fusions reads may look like "noise" to the aligners and may otherwise be filtered out. Instead, here, methods may include obtaining one or more mate-pairs of sequencing data from nucleic acid; aligning the mate-pairs to a reference (e.g., a human genome); identifying discordant mate-pair reads as possible rearrangements; and having a classification model validate the presence of the rearrangement.

To identify amplifications and deletions, DK may be used. For DK, specific barcodes are incorporated during library prep to index the tags that result from sequencing; the sample is sequenced and the tags are aligned to the reference. Tag densities are observed across the genome to identify outliers. Such techniques may be used identify amplifications and deletions. Whatever methods are used for detecting alterations, those methods are preferably validated against whole-exome PCR and Sanger sequencing from cancer DNA. When the methods are applied to a sample, the alteration(s) provisionally detected by the caller are validated for reporting by the trained classification model.

Methods of the invention have a number of useful and beneficial applications. Methods may be used for the therapeutic interpretation of cancer panels. Methods may be used to uniquely detect and prioritize variants and patients for treatments. Methods of the disclosure may be fully automated and scalable with a rapid turnaround time (e.g., less than a day). Clinical and research reports may be provided 135 describing, e.g., tumor genetics including, for example, clonality. Reports may identify tumor specific mutations including driver and passenger mutations. In preferred embodiments, a report is provided 135 that describes the DNA from the subject as including the structural alteration.

FIG. 8 shows a report according to some embodiments. Reports may allow methods of the invention to be useful in the continuing care of a cancer patient. After beginning a treatment regimen, the patient's tumor sequence can be analyzed again using the same methods. This second analysis can determine whether there are more or fewer mutations, which is indicative of whether the cancer is progressing. Embodiments of the invention may be implemented as a system to perform methods described herein.

Figure 9:
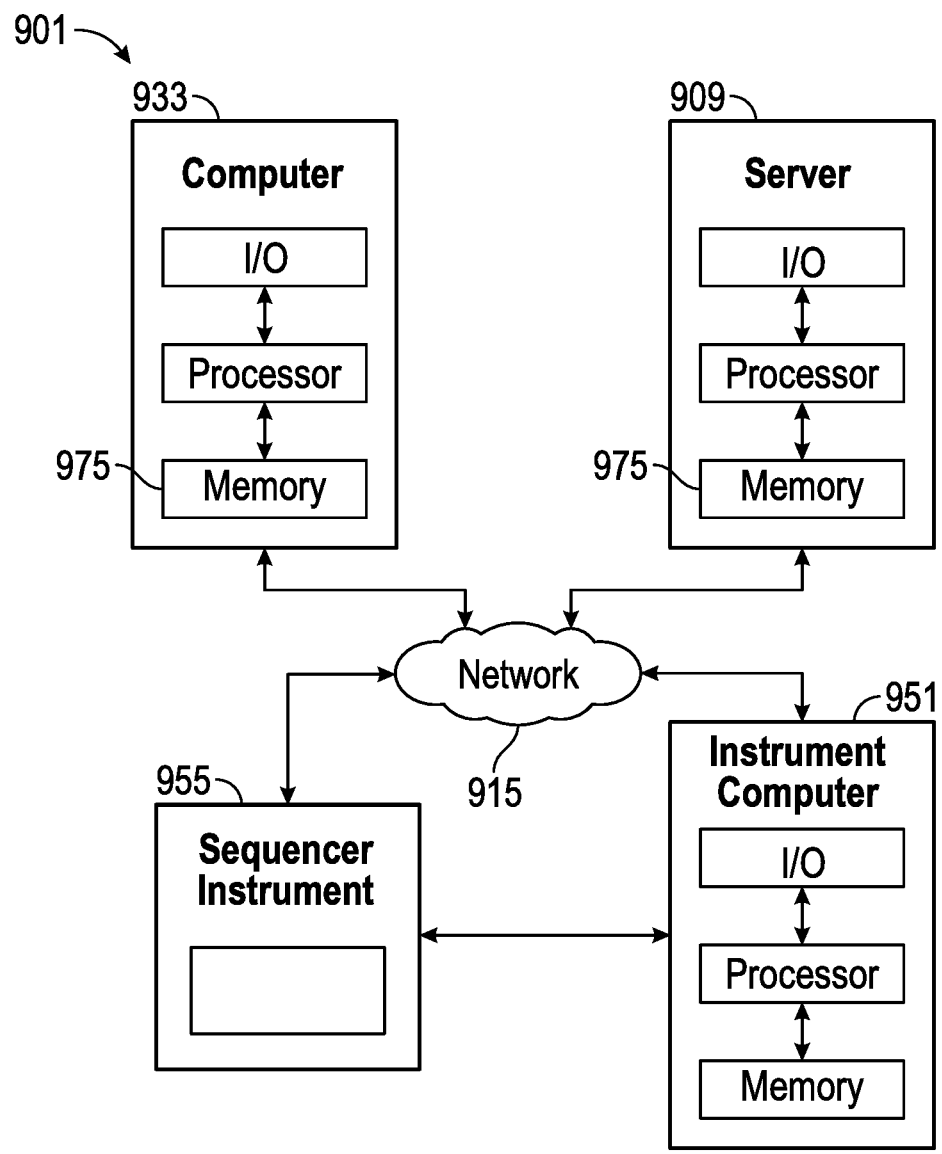
FIG. 9 shows a system for performing methods of the disclosure.

FIG. 9 shows a system 901 according to certain embodiments. The system 901 includes a computer 933 that has a processor coupled to memory and one or more input/output devices. The system 901 may also include either or both of a server computer 909 and a sequencing instrument 955, optionally with a sequencer computer 951. Each computer includes at least one processor coupled to memory and one or more input/output devices. Memory as used herein may be taken to refer to tangible, non-transitory computer readable storage media and may include one or any combination of RAM, ROM, hard drives, solid-state drives, optical disks, and removable drives. Those memory devices, taken together, may be collectively referred to as a memory subsystem 975 of the computer system 901. The memory subsystem 975 preferably has instructions stored therein that, when executed by the at least one processor, cause the system 901 to obtain sequence reads from DNA from a sample from a subject; comparing the sequence reads to a reference to detect at least one boundary of a structural alteration; validating the detected boundary as present in the DNA using a classification model trained on a training data set of sequences that include known structural alterations; and providing a report that describes the DNA from the subject as including the structural alteration.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLE

Example: A Machine Learning Approach for Somatic Mutation Discovery

Variability in the accuracy for somatic mutation detection may affect discovery of alterations and therapeutic management of cancer patients. To address this issue, we developed a somatic mutation discovery approach based on machine learning that outperformed other methods in identifying tumor alterations that were experimentally validated (sensitivity of 97% vs 90-99%; positive predictive value of 98% vs 34-92%). Analysis of tumor-normal exome data from 1,368 TCGA (the cancer genome atlas) samples using this method revealed concordance for 74% of mutation calls but also identified likely false positive and negative changes in TCGA data, including in clinically actionable genes. For melanoma and lung cancer patients treated with immune checkpoint inhibitors, determination of high-quality somatic mutation calls improved tumor mutation load-based predictions of clinical outcome. Integration of high-quality mutation detection in clinical NGS analyses improved the accuracy of test results compared to other clinical sequencing analyses (sensitivity of 100% vs 50-97%; positive predictive value of 100% vs 9-66%). These analyses provide an approach for improved identification of tumor-specific mutations and have important implications for research and clinical management of patients with cancer.

Introduction

Comprehensive molecular profiling of cancer through next-generation sequencing (NGS) approaches may be used in oncology for diagnostic and therapeutic management decisions. Tumor-specific (somatic) mutations, including single nucleotide alterations and small insertions or deletions, may affect key driver genes early during tumorigenesis. Over time, cancers accumulate additional mutations that may influence the underlying biology of the tumor cells, representing new opportunities for therapeutic intervention. Cancer therapies targeting specific driver genes altered in tumors maybe chosen based on methods of the disclosure. Examples include vemurafenib and trametinib in BRAF-mutated melanoma, and erlotinib and osimertinib in EGFR-mutated non-small cell lung cancer. The immune checkpoint inhibitor pembrolizumab recently received accelerated approval by the FDA for treatment of patients with solid tumors from any tissue type where the tumor was determined to have mismatch repair deficiency (dMMR) resulting in microsatellite instability (MSI-H) and higher mutation loads. High tumor mutation burden, resulting from repair defects or exposure to mutagens, has been associated with durable clinical response to a variety of immune checkpoint inhibitors, including nivolumab, ipilimumab and atezolizumab, and may serve as predictive biomarker for treatment response.

Systematic discovery of somatic alterations in new driver genes and pathways began with large-scale sequencing analyses in various human cancers using Sanger sequencing and NGS. These efforts were extended by The Cancer Genome Atlas (TCGA) and International Cancer Genome Consortium, profiling the molecular landscape of 33 common cancer types and over 10,000 patients. Due to the scale and complexity of TCGA, initial analysis efforts to characterize somatic mutations within tumors were typically unique to each cancer type. More recently, the PanCanAtlas project has generated a unified set of consensus mutation calls (Multi-Center Mutation Calling in Multiple Cancers or "MC3") across the entire TCGA cohort, although little if any validation of mutations has been performed for these datasets.

Based on these large-scale genomic efforts, targeted NGS approaches in clinical oncology may potentially be used to identify genetic alterations and inform decisions regarding patient therapy and management. Many challenges remain for somatic mutation detection, including sensitive detection of alterations that are subclonal or in low purity tumor samples as well as distinguishing these from germline changes or from artifacts related to polymerase chain reaction (PCR) amplification or sequencing. Head-to-head comparisons of laboratory developed tests with NGS analyses have reported a wide range of mutation concordance levels, leading to concern regarding the accuracy of such tests.

The disclosure provides a method for somatic mutation identification that utilizes machine learning strategies to optimize sensitivity and specificity for detection of true alterations. We compare the overall accuracy of this approach to existing methods for somatic mutation identification using simulated and experimentally validated whole-exome and targeted analyses. We evaluate the overall concordance of the method with mutation calls from TCGA exomes, examine the underlying causes of erroneous calls, including those in actionable driver genes, and assess the effects of discordant mutation calls on tumor mutational burden and clinical response to cancer immunotherapy. To assess the importance of high quality mutation analyses in clinical testing, we perform head-to-head comparisons of clinical sequencing with or without our machine learning approach. Overall, these analyses highlight the importance of improved somatic mutation detection for interpretation of large-scale genome studies and for application of these approaches to clinical practice.

Results

Overview of Approach

We created a method for analyzing next-generation cancer sequence data called Cerebro that uses machine learning to identify high confidence somatic mutations while minimizing false positives.

Figure 10:
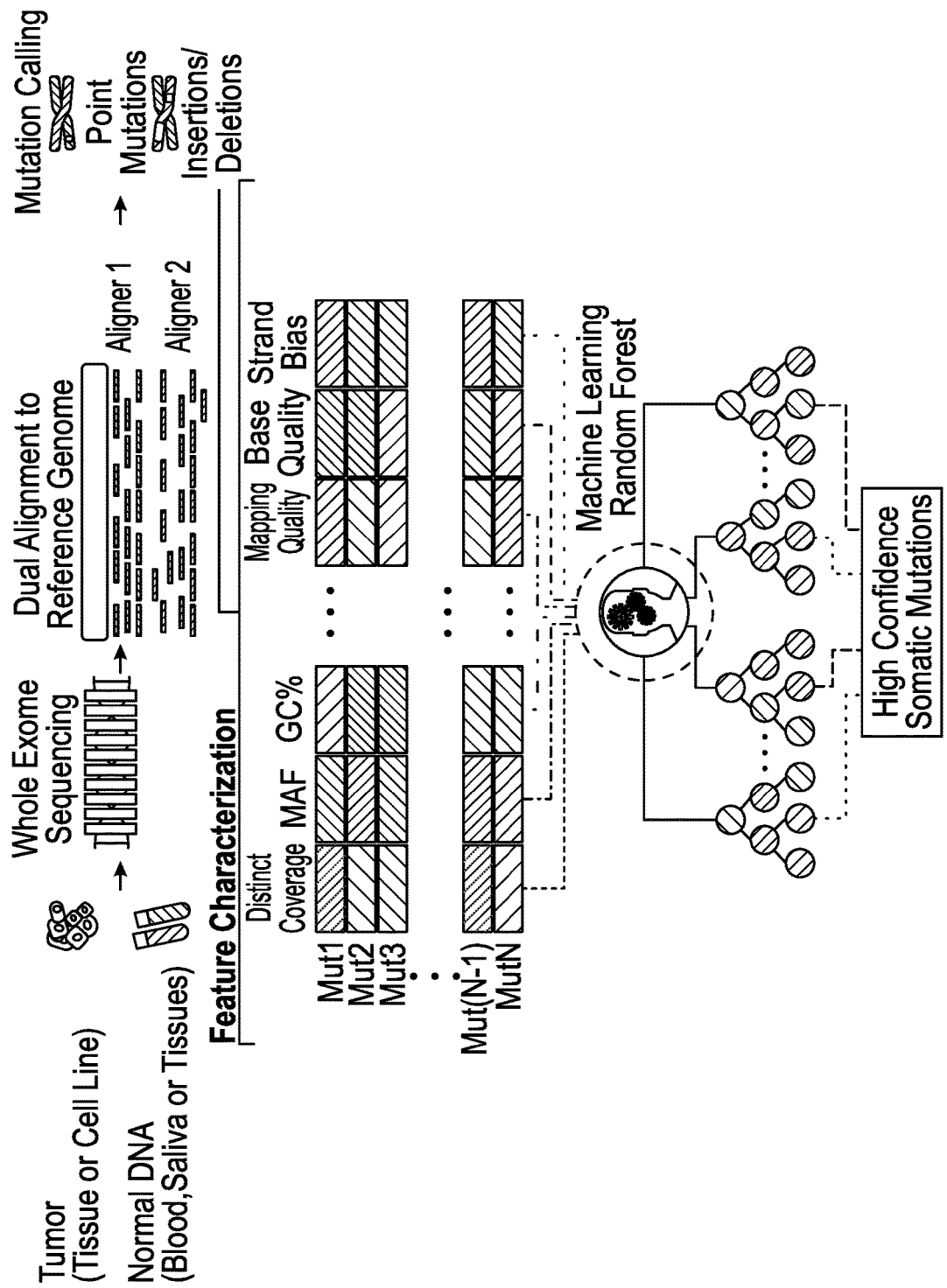
FIG. 10 is a diagram of a method of mutation detection.

FIG. 10 is a diagram of a method of mutation detection using Cerebro. Cerebro utilizes a specialized random forest classification model that evaluates a large set of decision trees (e.g., at least 1,000) to generate a confidence score for each candidate variant. The model was trained using a normal peripheral blood DNA sample where exome regions were captured and sequenced twice using NGS methods. A total of 30,000 somatic variants comprising substitutions, insertions and deletions at mutant allele fractions from 1.5% to 100% were introduced in silico into one set of NGS data in order to provide the classifier with a training set of "tumor-specific" mutations as well as a representative source of NGS errors and artifacts that might otherwise be mislabeled as variants. The second NGS sequence data set from the same sample was used as the matched normal, and the combined data sets were analyzed for detection of somatic variants.

We considered over 300 features that would optimize performance for identifying true somatic variants, ultimately selecting 15 feature categories from two separate alignment programs that included alignment characteristics (mapping quality, mismatches), sequence quality information (coverage, base quality) and information related to specific alterations (allele frequency, nearby sequence complexity, presence of alteration in matching normal specimen). Once implemented in certain embodiments, Cerebro utilized 1,000 decision trees for analysis of each mutation, with each tree evaluating a unique combination of the selected information supporting a candidate variant. The resultant confidence score from the Cerebro model represented the proportion of decision trees that would classify a candidate variant as somatic.

Evaluation of Mutation Calling Accuracy

To systematically assess the accuracy of Cerebro for mutation detection, we designed a series of validation studies using simulated and experimental cancer exomes, and evaluated the performance of this approach as compared to existing software tools commonly used for somatic variant identification in research and clinical genomic analyses.

Figure 11:
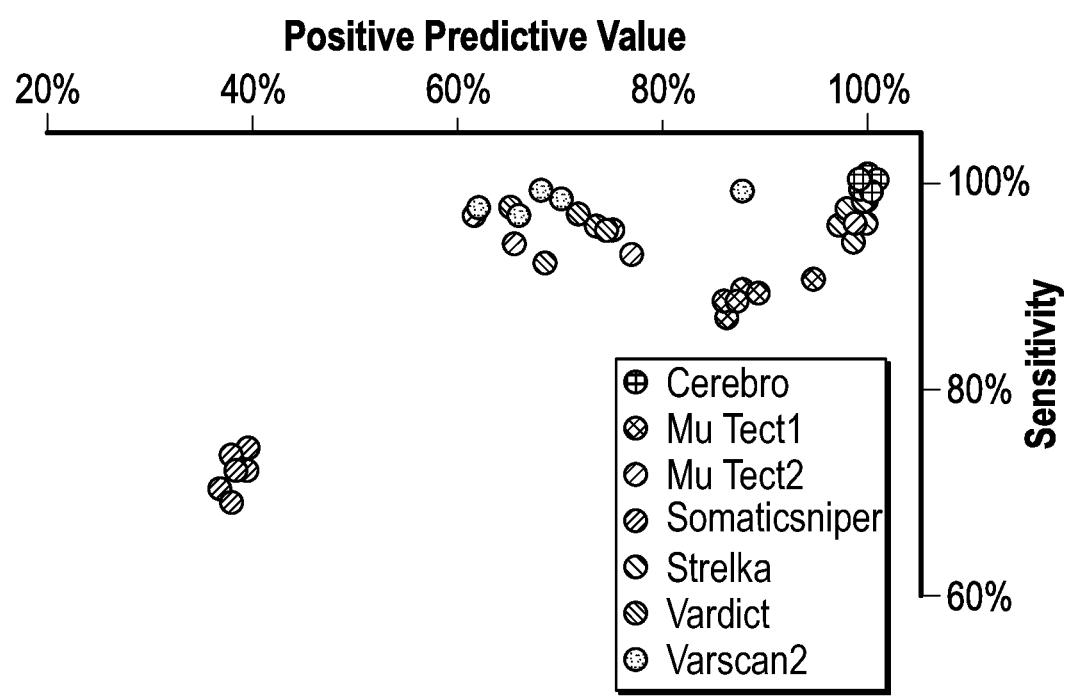
FIG. 11 shows positive predictive value vs. sensitivity for simulated low-purity tumor datasets created from normal cell line sequence data.
Figure 12:
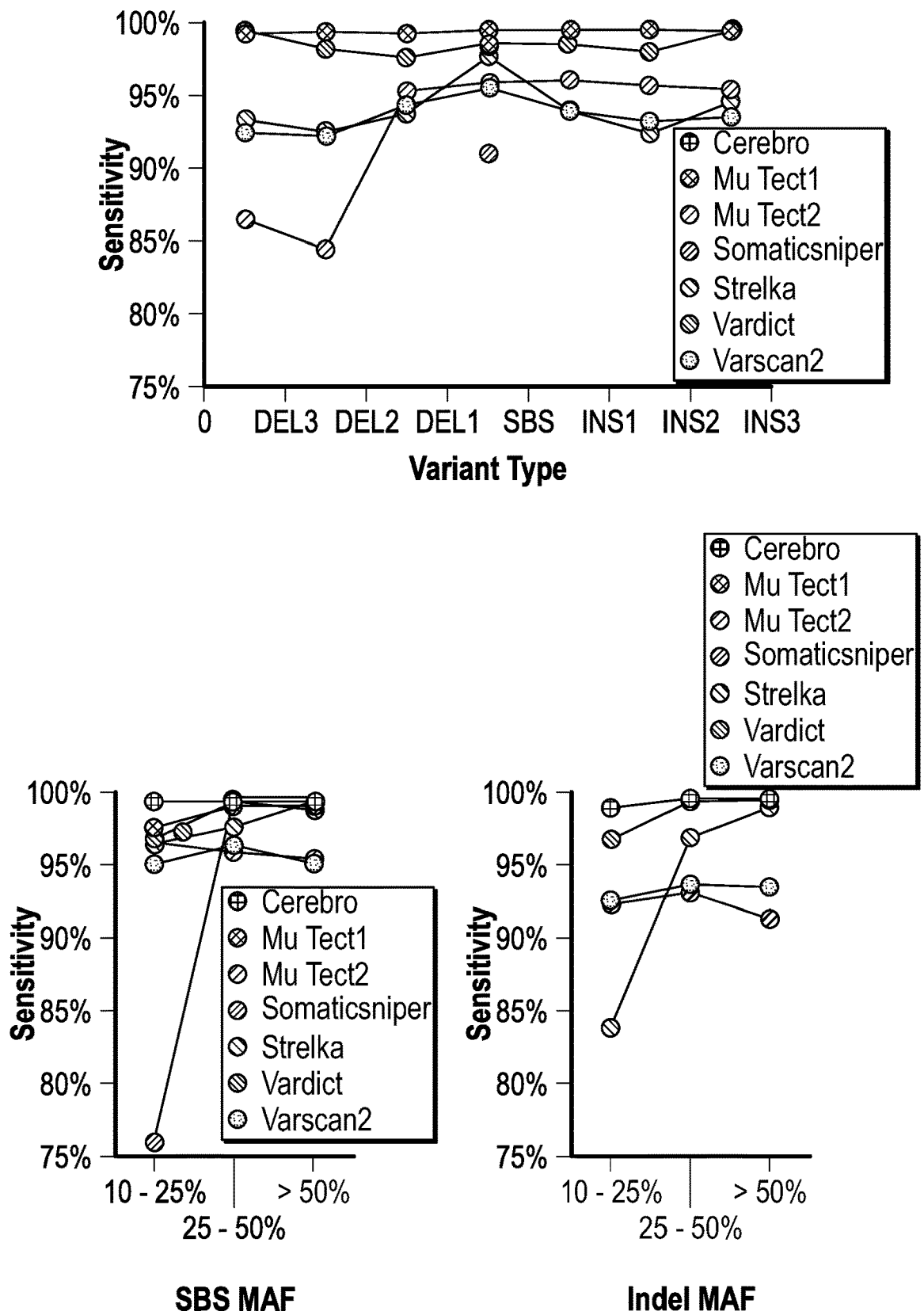
FIG. 12 shows sensitivity stratified by mutation type, calculated from simulated mutations across mutation types and allele frequencies.
Figure 13:
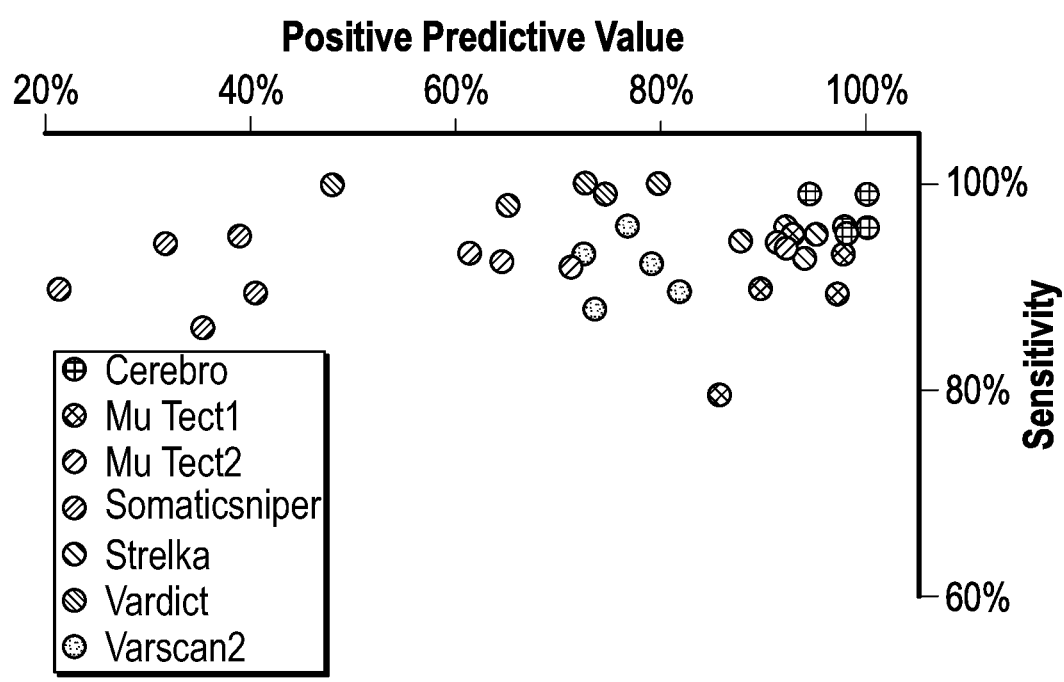
FIG. 13 gives positive predictive value vs. sensitivity for cell line datasets.

FIGS. 11-13 show validation study performance results. FIG. 11 shows positive predictive value vs. sensitivity for simulated low-purity tumor datasets created from normal cell line sequence data. FIG. 12 shows sensitivity stratified by mutation type, calculated from simulated mutations across mutation types and allele frequencies. FIG. 13 gives positive predictive value vs. sensitivity for cell line datasets with experimentally validated somatic mutations. DEL=deletion, INS=insertion; 1, 2, or 3=length of indel; SBS=single base substitution; MAF=mutant allele frequency. We performed three studies using a set of six normal cell lines with NGS exome data. Two of those studies contained simulated mutations, with in silico somatic mutations spiked in to a normal DNA sample. In our first study, we simulated low-purity tumors by incorporating 132 coding somatic mutations (120 SBS, 12 indels) with mutant allele frequencies ranging from 10% to 25% in the exome data (FIG. 11). To characterize false positive rates for the various tools, we analyzed technical replicate exome pairs of the six normal cell lines. We additionally created simulated exomes with in silico spike-ins of 7,000 somatic SBS and indel changes with variable mutant allele frequencies (ranging from 10% to 100%), comprising a total of 42,000 somatic changes across the six samples that could be detected through these approaches (FIG. 13). This last study allowed us to examine the sensitivity of the various tools on specific mutation types and allele frequencies. In all cases, the location, type and level of in silico alterations were different from those utilized in the training of the Cerebro algorithm. Overall, we observed substantial variation in sensitivity and positive predictive value among the tested variant classification programs (FIGS. 11 & 12). Cerebro maintained the highest level of sensitivity and positive predictive value, while other methods resulted in moderate to high false positive rates (FIG. 11). False positive calls by other methods were frequently associated with indicators such as poor tumor/normal coverage, low mutant base quality, and low mutant mapping quality.

To assess mutation detection performance using independently obtained experimental data, we next analyzed five matched tumor and normal specimens for which somatic mutations had been previously identified and validated through independent whole-exome sequencing. These previous analyses carefully evaluated the entire coding sequences of the samples through PCR amplification of 173,000 coding regions and Sanger sequencing of the amplification products. Any observed alteration had been re-sequenced in the tumor and normal sample in order to confirm its tumor origin. Because Sanger sequencing analyses were designed to identify only clonal or near clonal alterations, we supplemented Sanger validated alterations previously observed in this set of samples (n=314), with additional bona fide changes that were identified by a consensus of multiple NGS mutation callers (n=163), or were detected by up to two mutation callers and validated using droplet digital PCR (n=18), a highly sensitive method for detection of alterations in a subset of DNA molecules. Comparison of all mutation callers to this reference set of alterations revealed that Cerebro had the highest overall accuracy compared to other methods (FIG. 13).

Evaluation of Tumor Exomes from TCGA

We assessed whether the improved capabilities of Cerebro could be used to increase accuracy of mutation calling in large-scale cancer genome sequencing efforts including TCGA, as these serve as the basis for various research efforts in human cancer. We used Cerebro to analyze paired tumor-normal exomes from 1,368 patients in TCGA, focusing on tumors that would be relevant for both targeted therapies and immunotherapy. This set consisted of all available patients with non-small cell lung adenocarcinoma, non-small cell lung squamous cell carcinoma, and bladder urothelial carcinoma, as well as selected patients with higher mutational loads that had colorectal, gastric, head and neck, hepatocellular, renal, uterine cancer, or melanoma (Table 1 in FIG. 23). A total of 365,539 somatic alterations were identified, with an average of 267 somatic alterations per tumor (range, 1-5,871).

Figure 14:
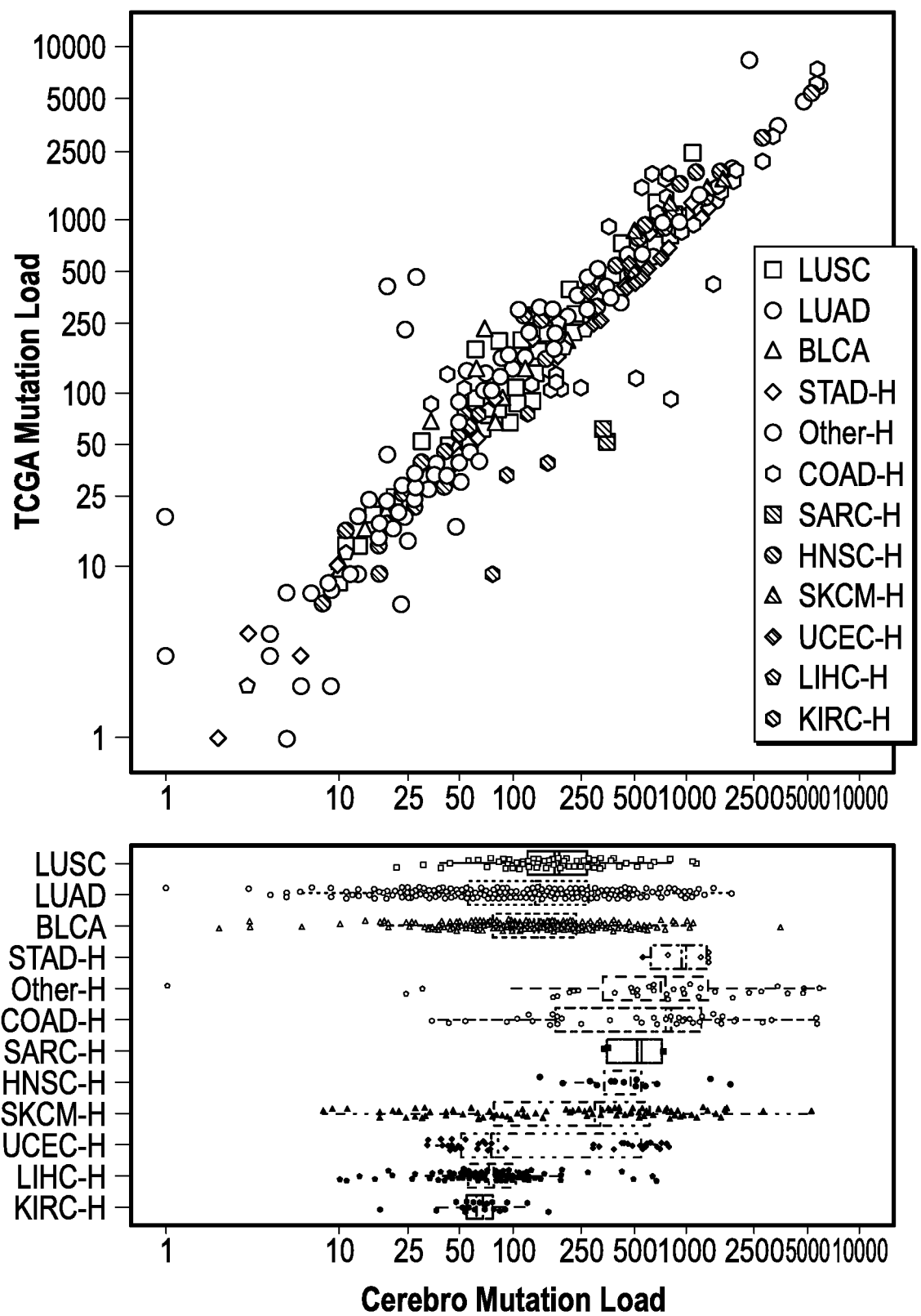
FIG. 14 shows mutational loads between two mutation calls.
Figure 15:
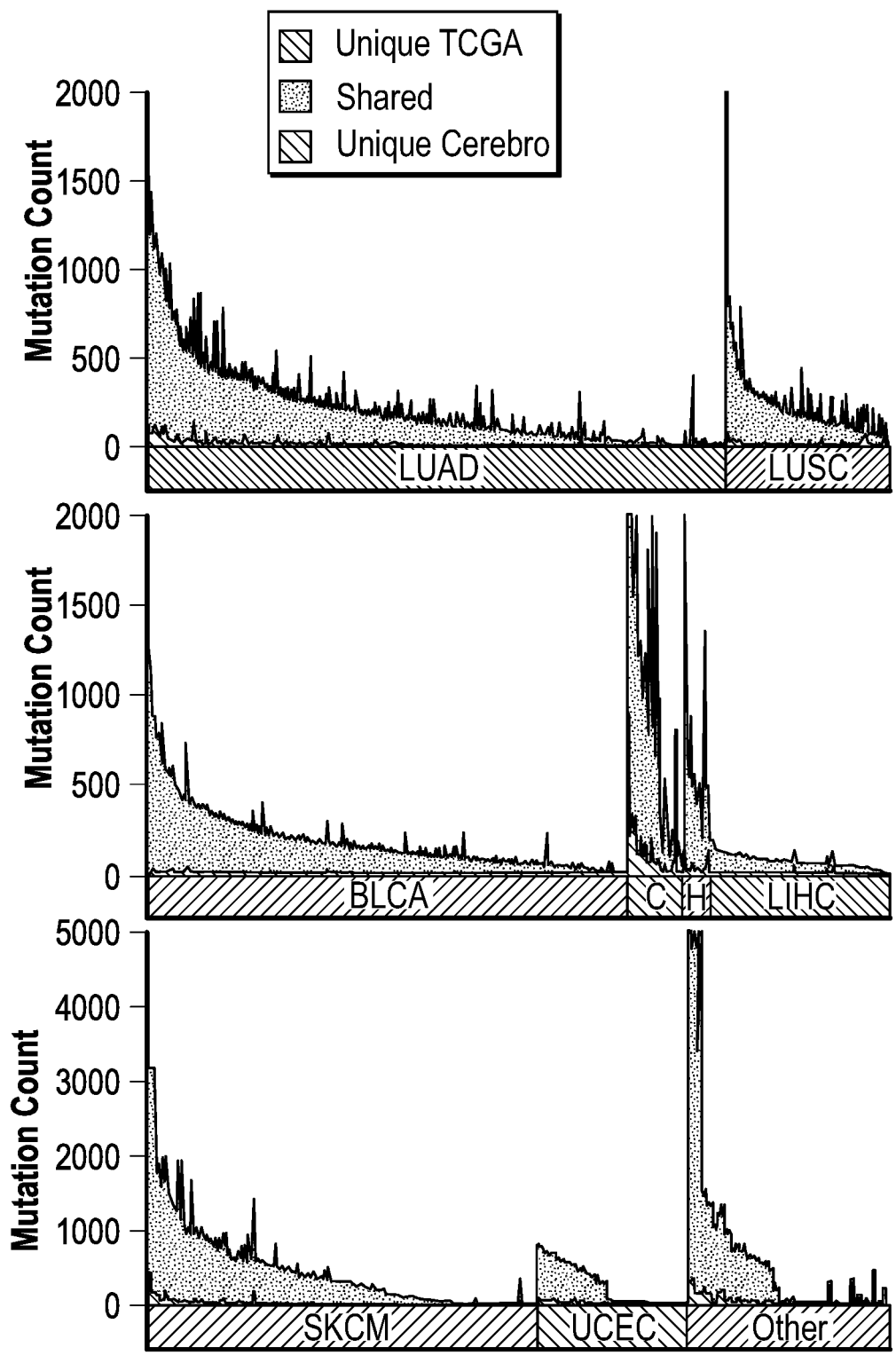
FIG. 15 reports unique/shared status for somatic mutations across samples.

FIGS. 14 and 15 give a comparison of TCGA and Cerebro mutations for 1,368 exomes. Somatic mutations from the TCGA MC3 project and Cerebro were compared for concordance. FIG. 14 shows the total mutational loads between the two mutation calls shared by cancer type. LUSC=lung squamous cell carcinoma; LUAD=lung adenocarcinoma; BLCA=bladder; STAD=stomach; COAD=colorectal; SARC=sarcoma; HNSC=head and neck squamous cell; SKCM=melanoma; UCEC=uterine; LIHC=liver; KIRC=kidney; *–H=set enriched for high mutation load samples.

FIG. 15 reports unique/shared status for somatic mutations across all samples. C=colorectal; H=head and heck squamous cell. The total number of somatic mutations measured across the various tumor types was largely consistent with previous analyses of cancer exomes (FIG. 14). We found a significant positive correlation for mutation loads between Cerebro and the TCGA PanCanAtlas MC3 method that utilizes consensus calls among seven different mutation callers (Pearson correlation coefficient=0.93, $P<0.0001$; FIG. 14), with 74.0% of somatic mutations shared between the two approaches. However, we found that 10.3% of calls detected by Cerebro (n=44,439) were apparently missed by TCGA while 15.7% of alterations identified by TCGA (n=68,138) were not considered somatic alterations by Cerebro (FIG. 15). Individual tumors that were re-analyzed by Cerebro had mutation loads that differed by as many as 390 (95%) fewer or 729 (800%) more alterations compared to original calls. Comparison of detected alterations between Cerebro and other TCGA call sets (MC3, FIREHOSE, MuTect2) showed increasing concordance of Cerebro calls from MuTect2 (least concordant; average 60.2%) to MC3 (most concordant; average 75.8%). These observations are consistent with our previous analyses of individual mutation callers and support the notion that the use of multiple approaches in MC3 is likely to reduce the false positive observations resulting from individual methods, but may still have additional errors compared to Cerebro.

Figure 16:
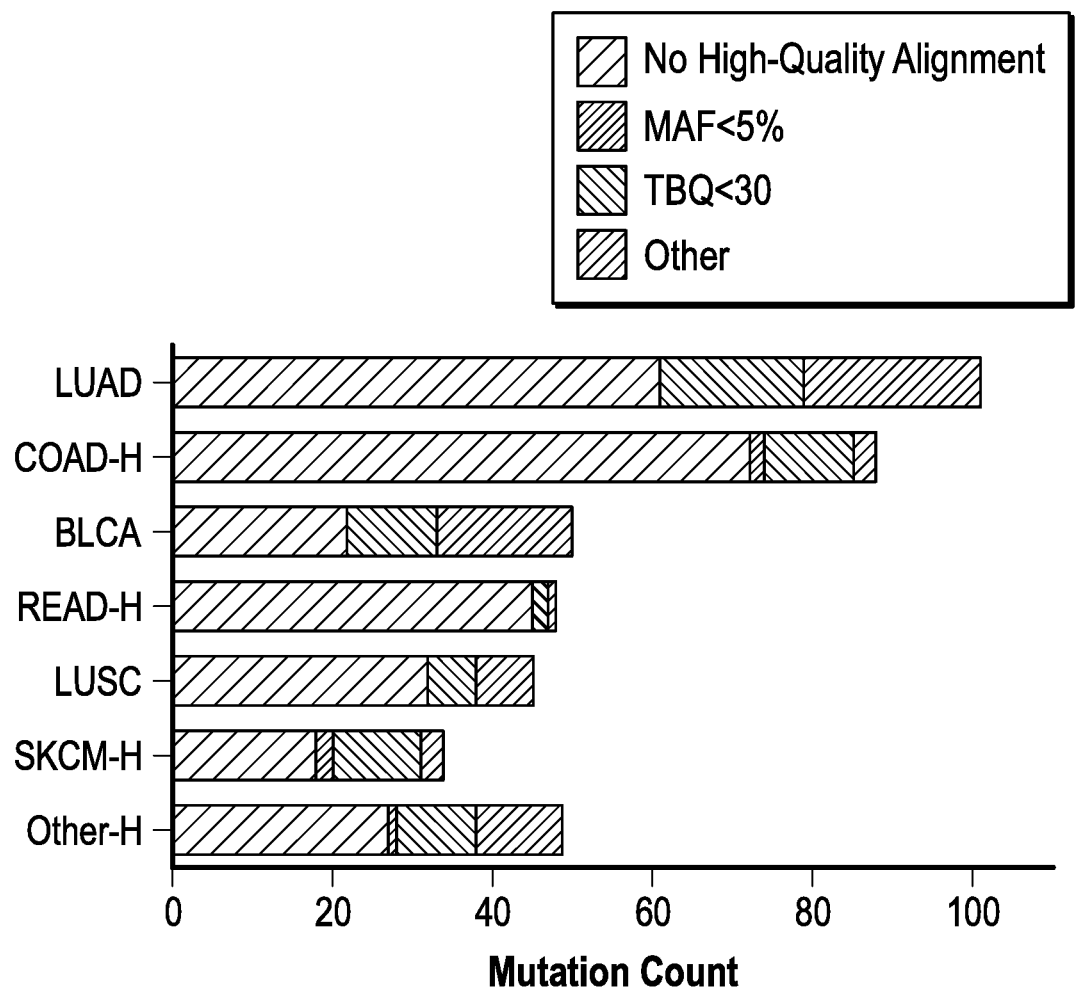
FIG. 16 shows evaluation of various genes.
Figure 17:
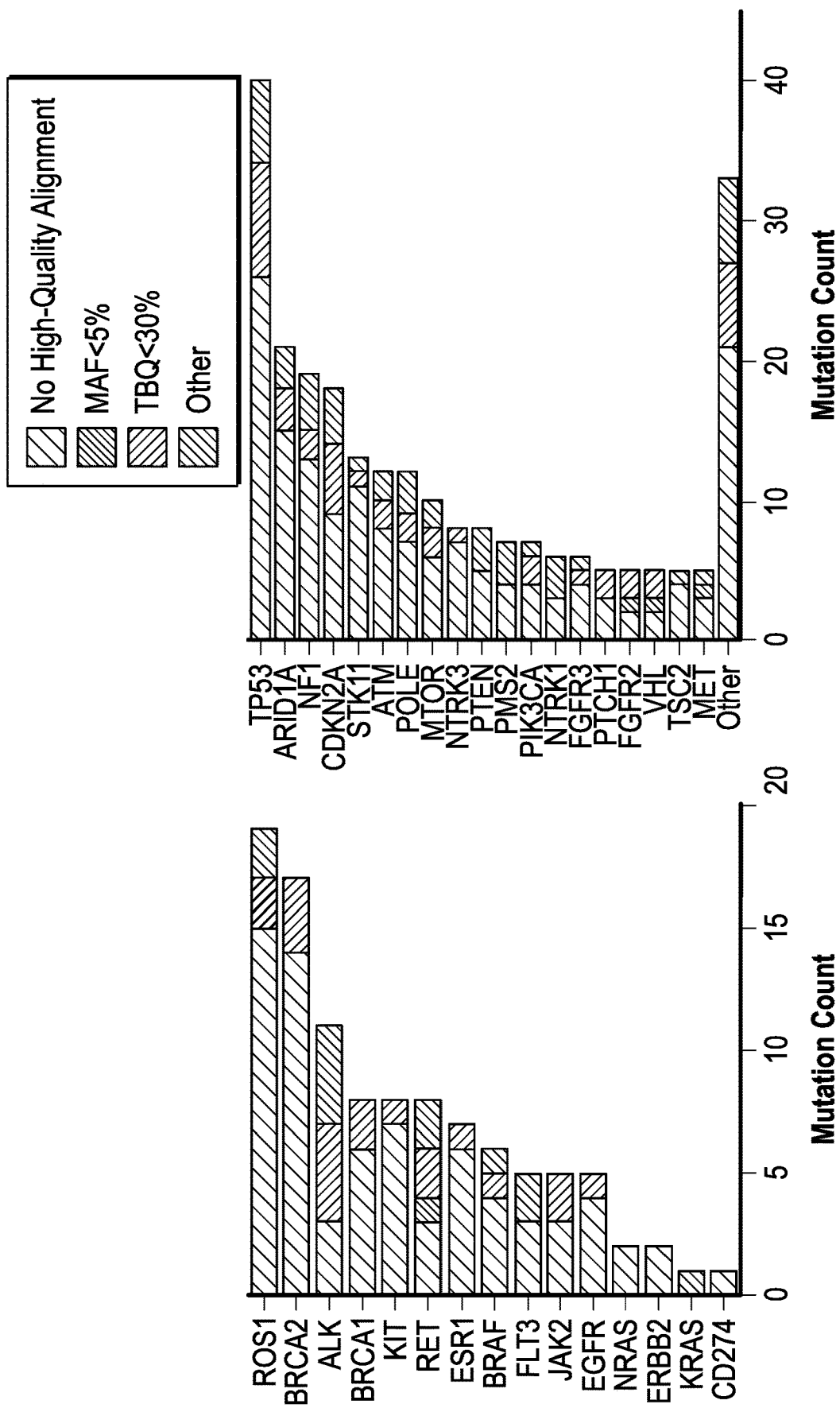
FIG. 17 is a distribution of problematic TCGA driver gene calls by genes with approved FDA therapies (left panel) or ongoing clinical trials (right panel).
Figure 18:
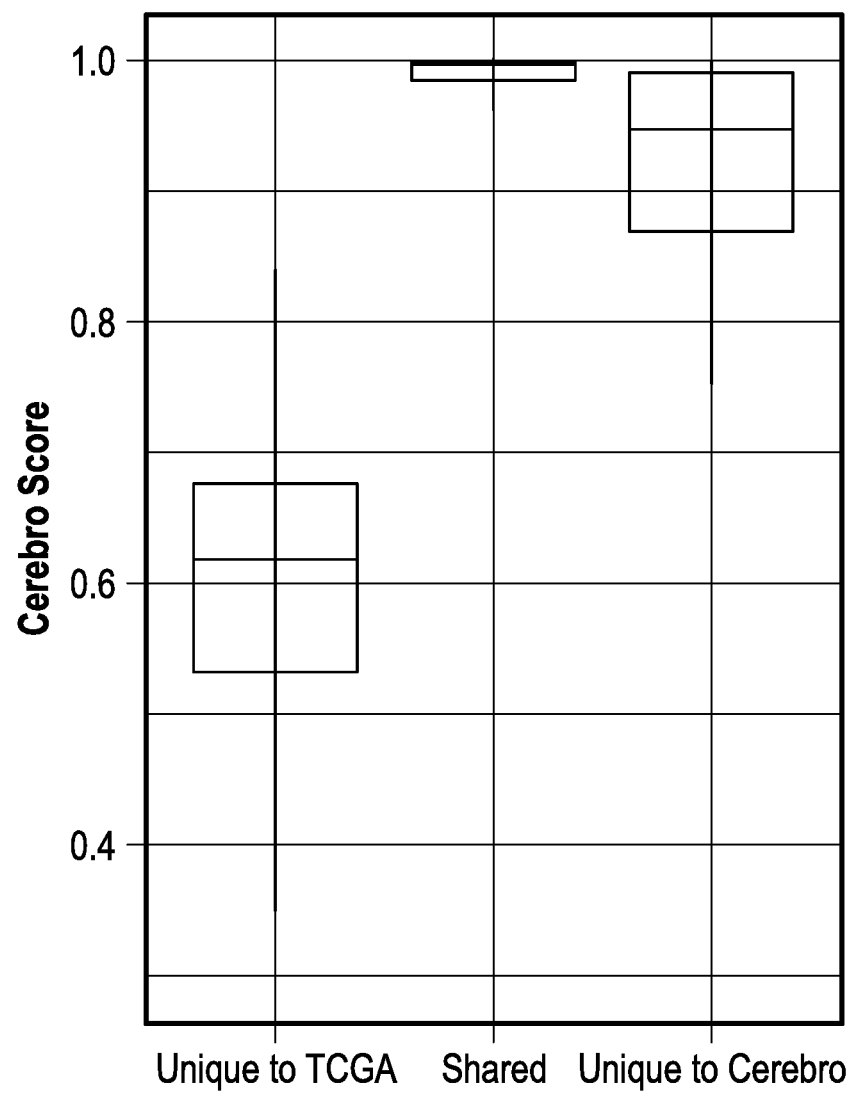
FIG. 18 gives Cerebro confidence scores.

To more carefully evaluate discordant alterations in TCGA, we investigated somatic mutation calls for a set of 66 well-characterized cancer driver genes. FIGS. 16-18 give an analysis of cancer driver gene mutations. FIG. 16 shows that evaluation of mutations among 66 oncogenes and tumor suppressor genes indicated a large number of low confidence mutations unique to TCGA associated with various problematic features (No High-Quality Alignment=no consistent alignment found with at least 1 mutant base with quality higher than 30; MAF<5%=mutant allele frequency below 5%; TBQ<30=tumor base quality below 30). FIG. 17 is a distribution of problematic TCGA driver gene calls by genes with approved FDA therapies (left panel) or ongoing clinical trials (right panel).

FIG. 18 gives the Cerebro confidence scores of mutations uniquely called by TCGA were significantly lower than other identified mutations. Of the 1,368 evaluated tumors, 1,257 (92%) had a mutation in this gene set, with 4,037 shared somatic mutations between TCGA and Cerebro, and a total of 777 alterations that were discordant between the analyses. Further examination revealed that most of the 429 mutations called only by TCGA were associated with poor sequence quality and alignment issues that were likely to not represent bona fide alterations (FIG. 16). Among driver genes associated with FDA-approved therapies or ongoing clinical trials (FIG. 17), we found low confidence TCGA mutations in 211 (16.8%) of patients. Quality confidence scores as determined by Cerebro of mutations uniquely called by TCGA were significantly lower than mutations observed by both platforms ($P<0.0001$; FIG. 18) or those that were uniquely detected by Cerebro ($P<0.0001$; FIG. 18). Overall, these results suggest that current TCGA data sets contain a significant number of false negative and positive somatic alterations in both passenger and driver genes among many tumor types, and the new mutation calls determined here provide an improved resource for analysis of TCGA sequence data.

Somatic Mutation Burden and Response to Cancer Immunotherapy

To evaluate recently reported associations between total somatic mutation count (i.e., mutational burden) and response to immune checkpoint blockade, we next obtained paired tumor-normal exome data from two recent studies including a study of response to anti-PD-1 therapy for 34 non-small cell lung cancer (NSCLC) patients, and a study of response to anti-CTLA-4 in 64 melanoma patients. Using Cerebro to analyze these NGS data, we compared our results to the mutations reported in the original publications, limiting our analyses only to nonsynonymous SBS changes as other types of alterations were not included in the published analyses. Across the NSCLC cohort, 9,049 and 6,385 mutations were identified in the original study and our re-analysis, respectively. In the melanoma cohort, 25,753 and 32,092 mutations were identified by the original publication and our re-analysis, respectively.

Figure 19:
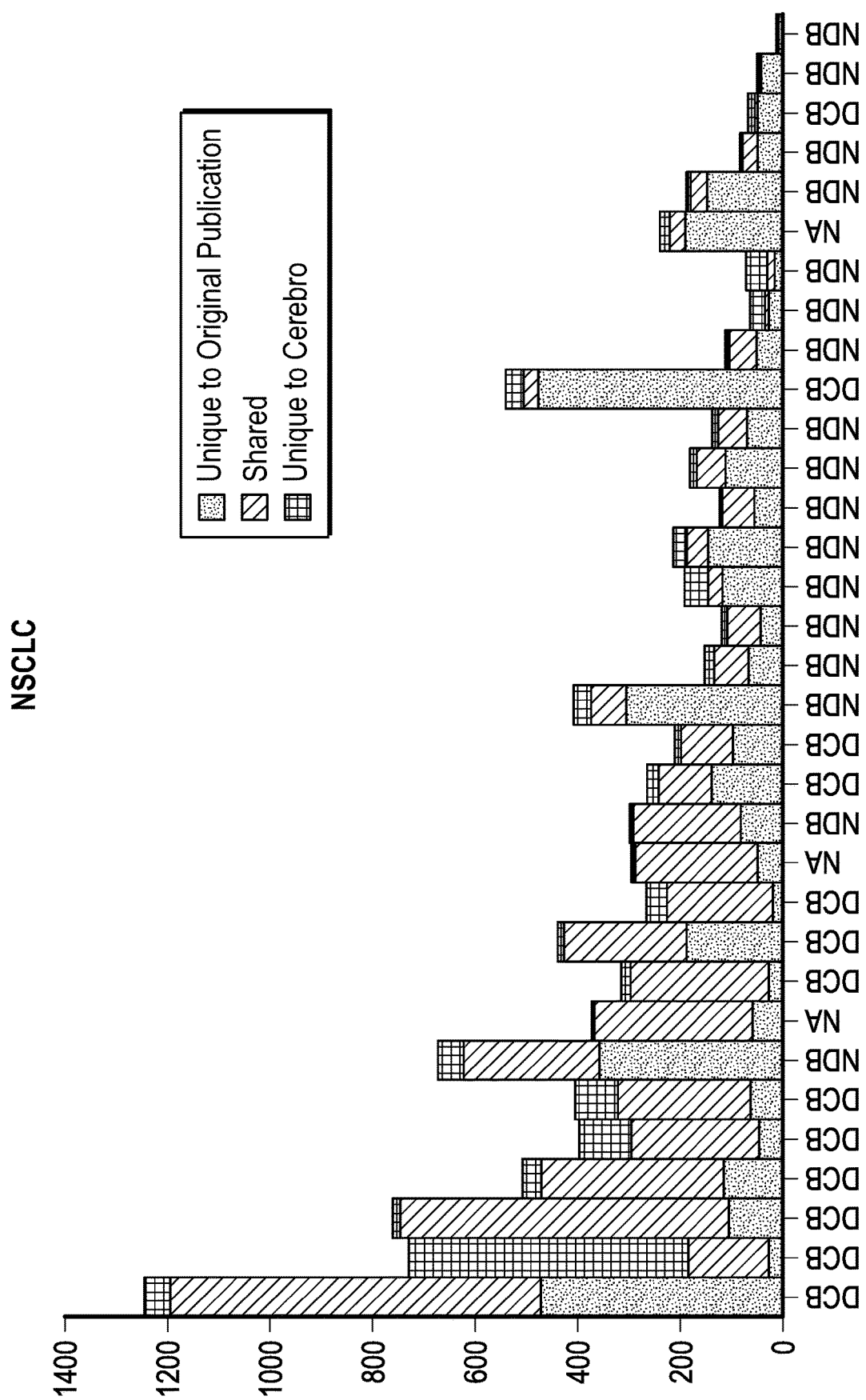
FIG. 19 shows the unique/shared mutation status for all patients.
Figure 19:
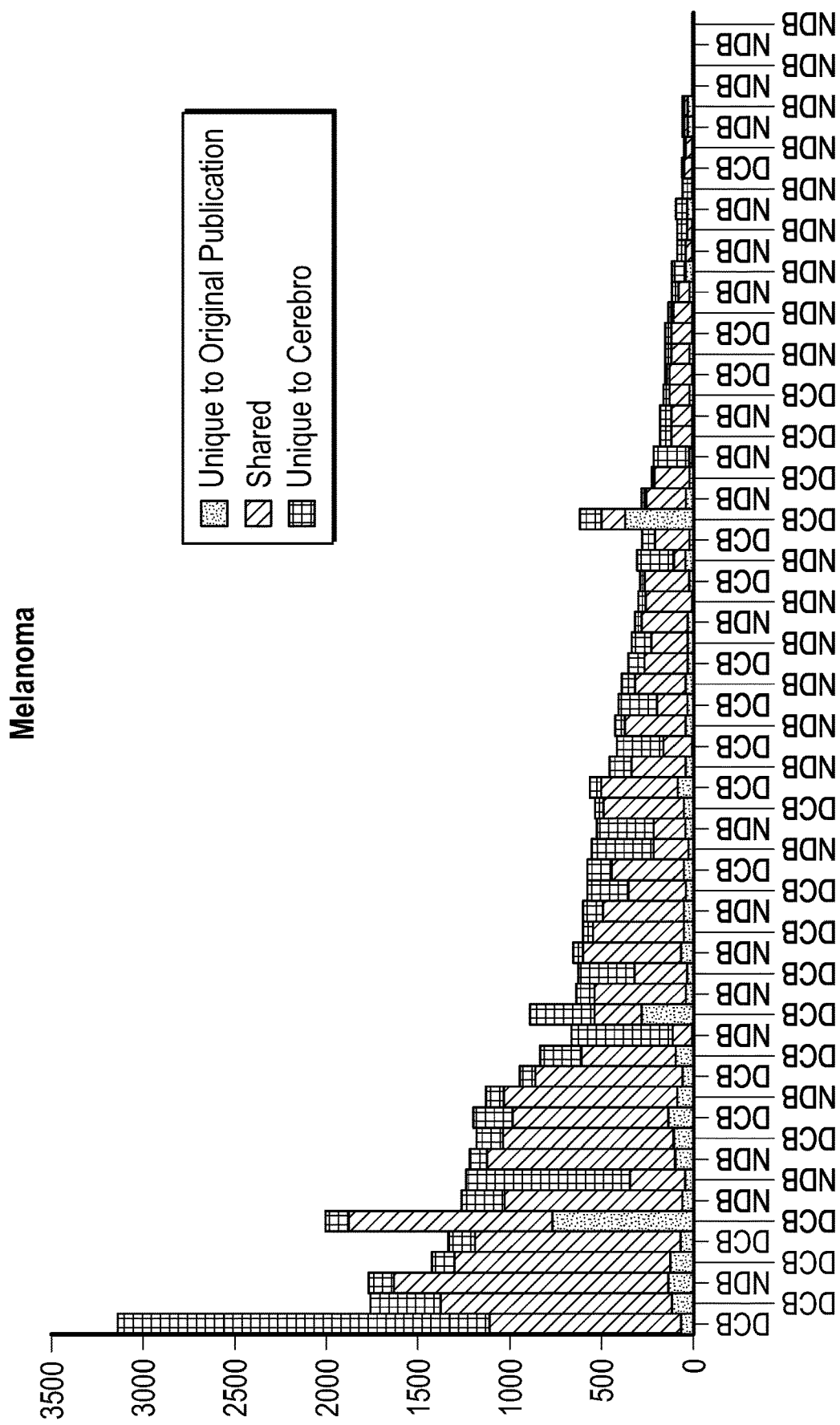
Figure 20:
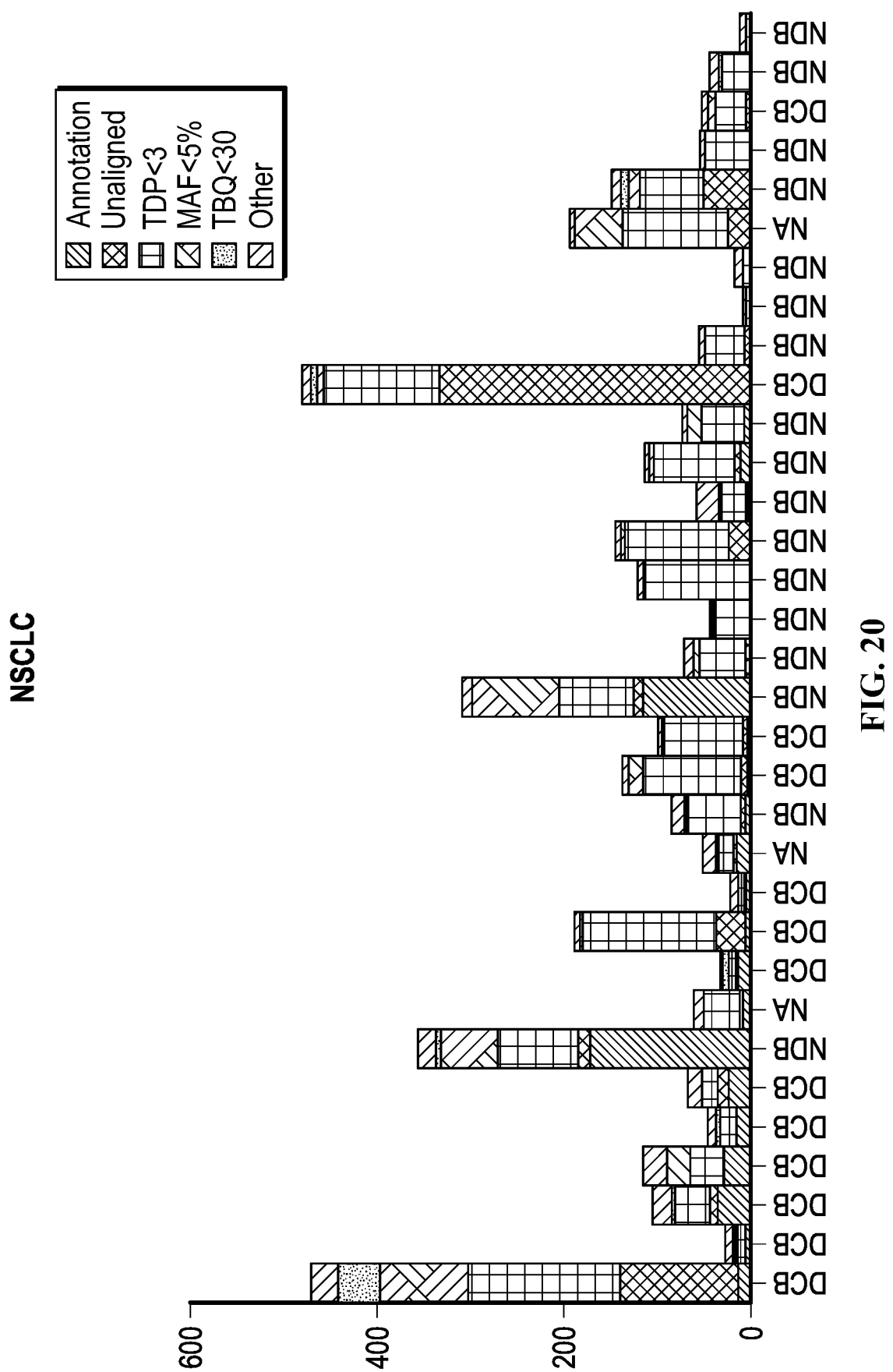
FIG. 20 reports problematic mutations annotated by characteristic issue.
Figure 20:
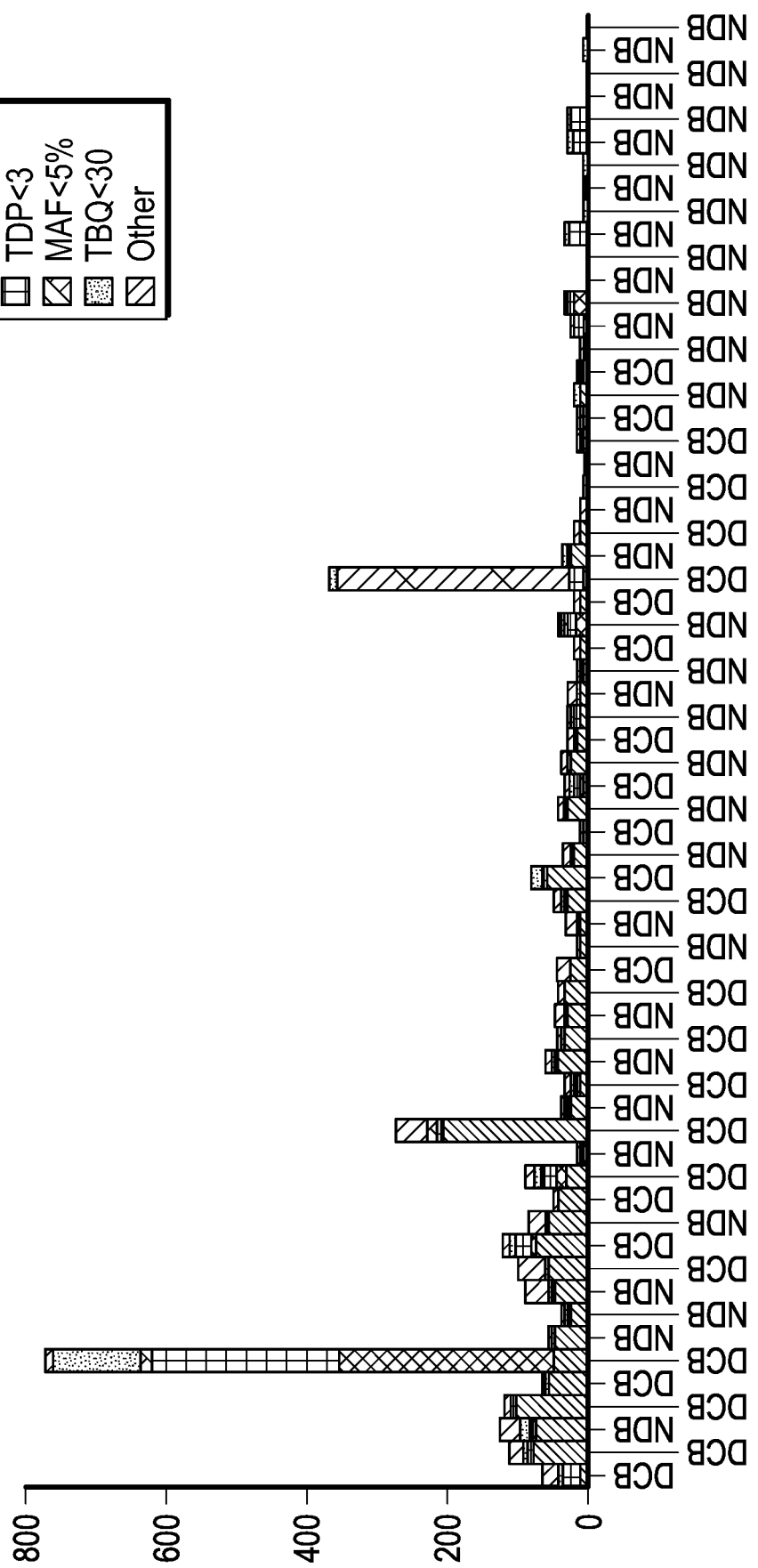
Figure 22:
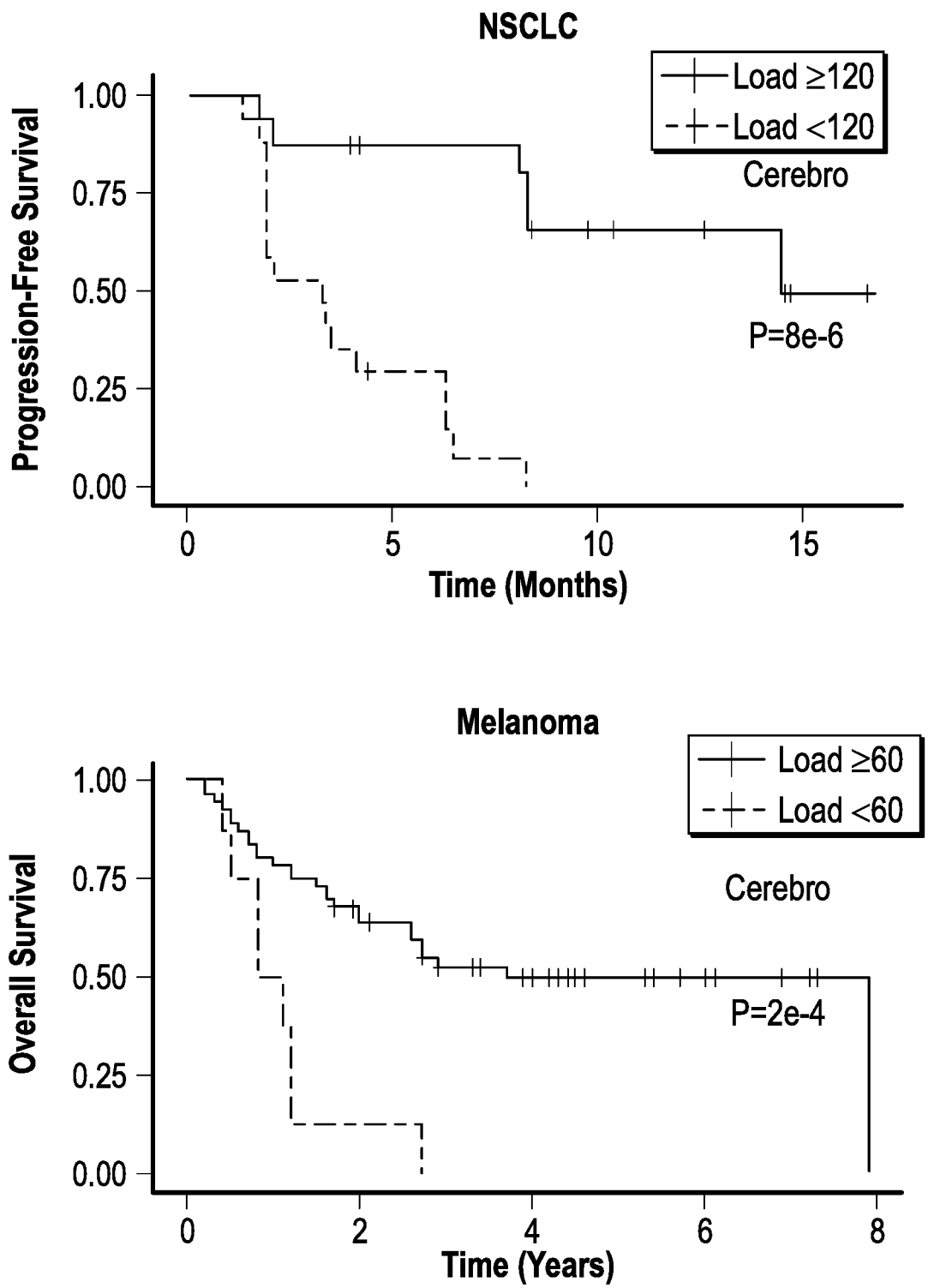
FIG. 22 is a Kaplan-Meier analysis of same samples using Cerebro mutational loads Log-rank P-value shown for each survival plot.
Figure 25A:
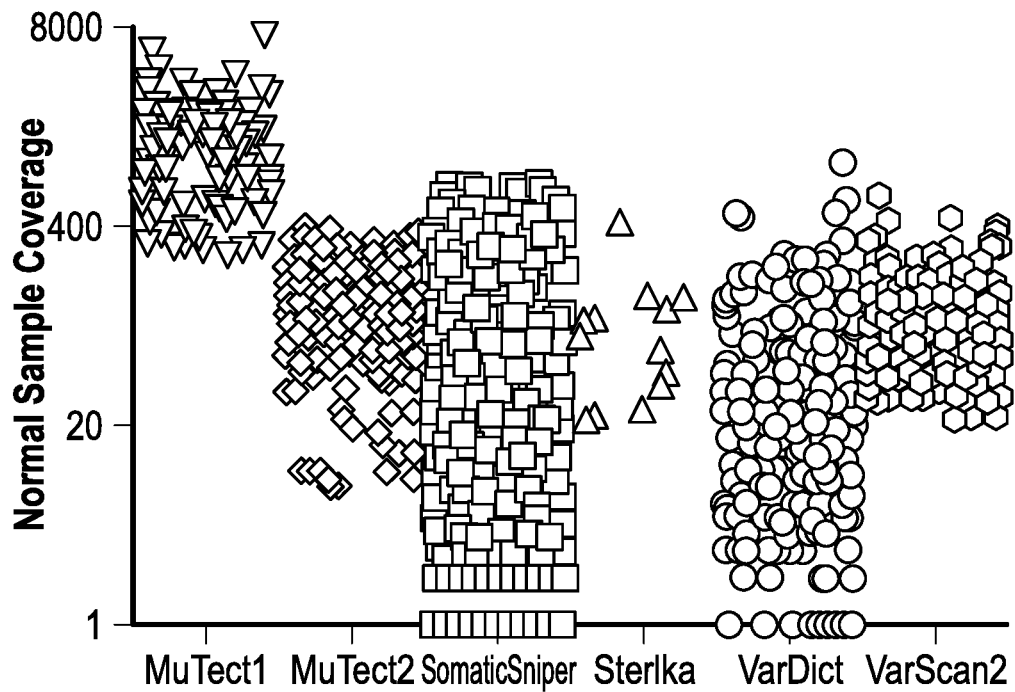
FIGS. 25A-25F show false position evaluation for somatic mutation callers.
Figure 25B:
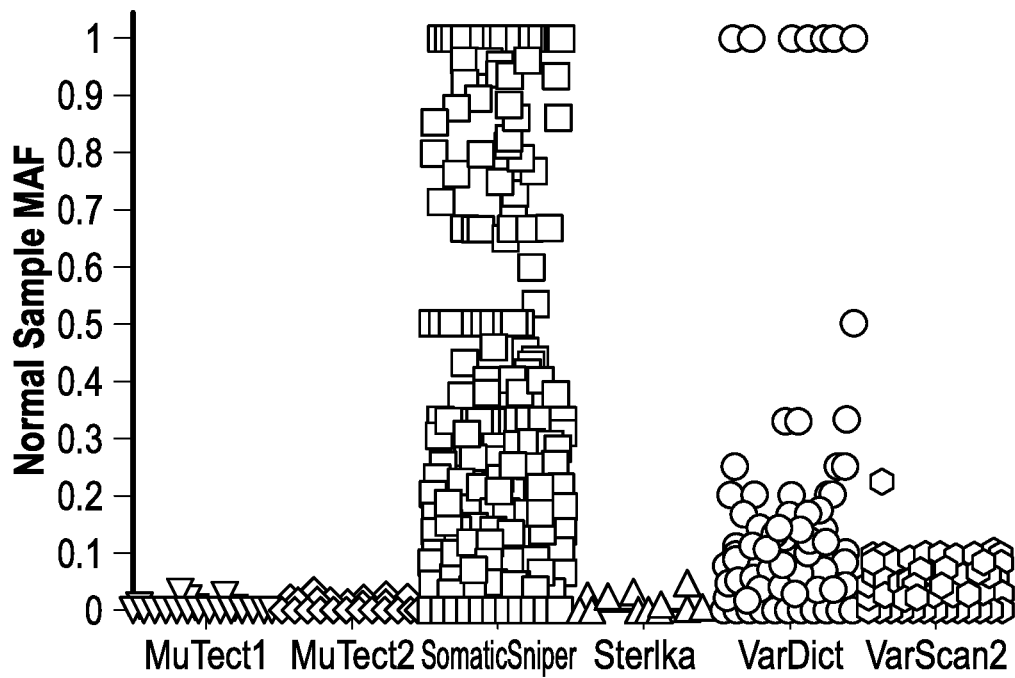
Figure 25C:
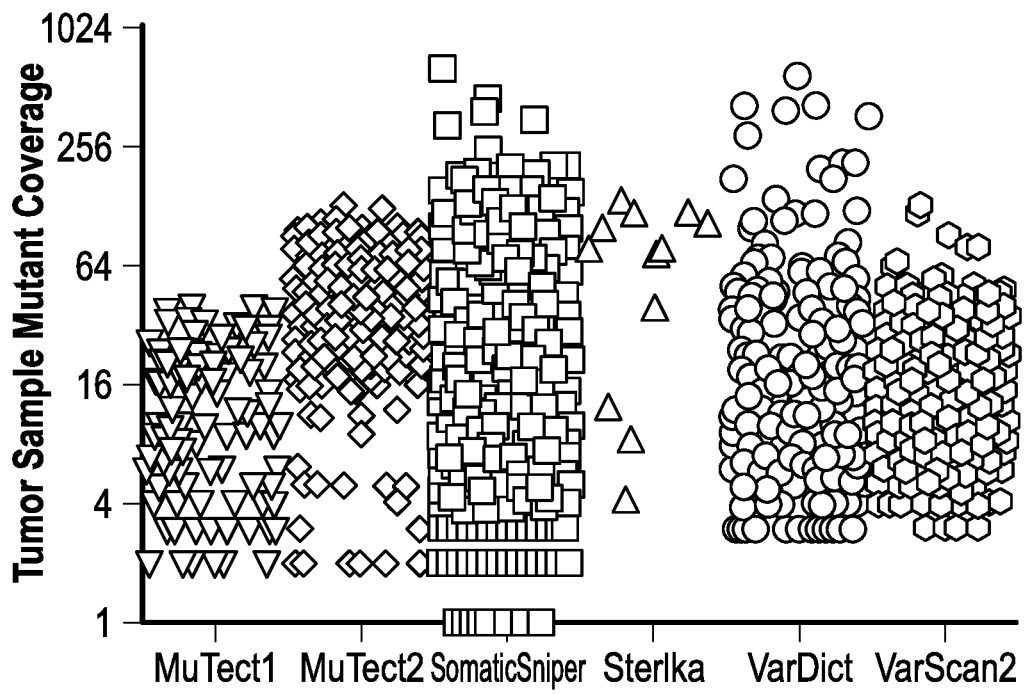
Figure 25D:
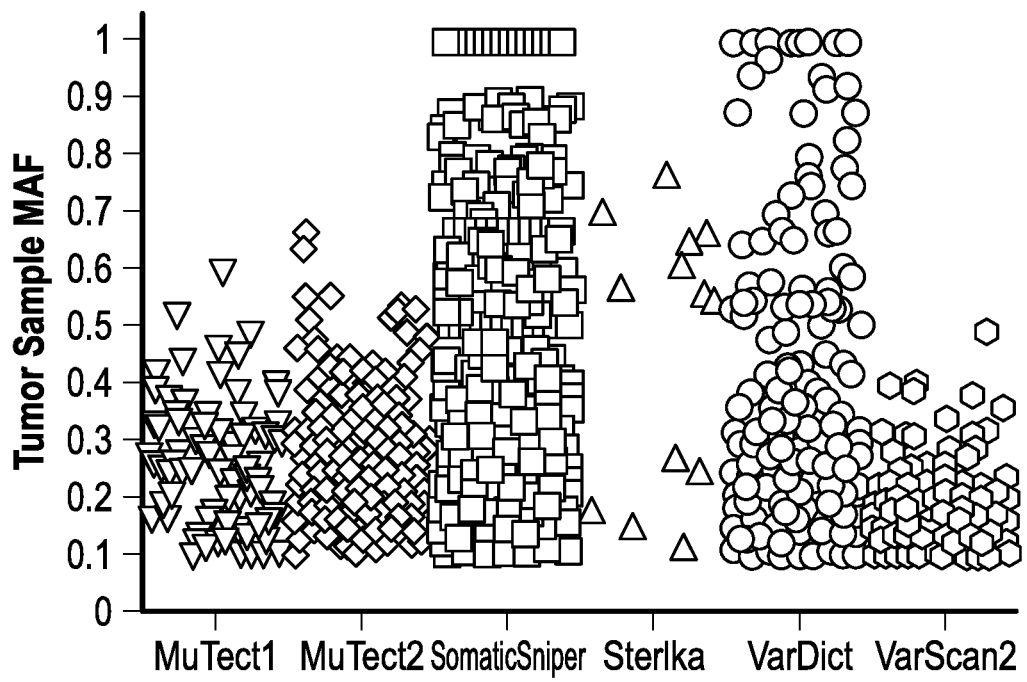
Figure 25E:
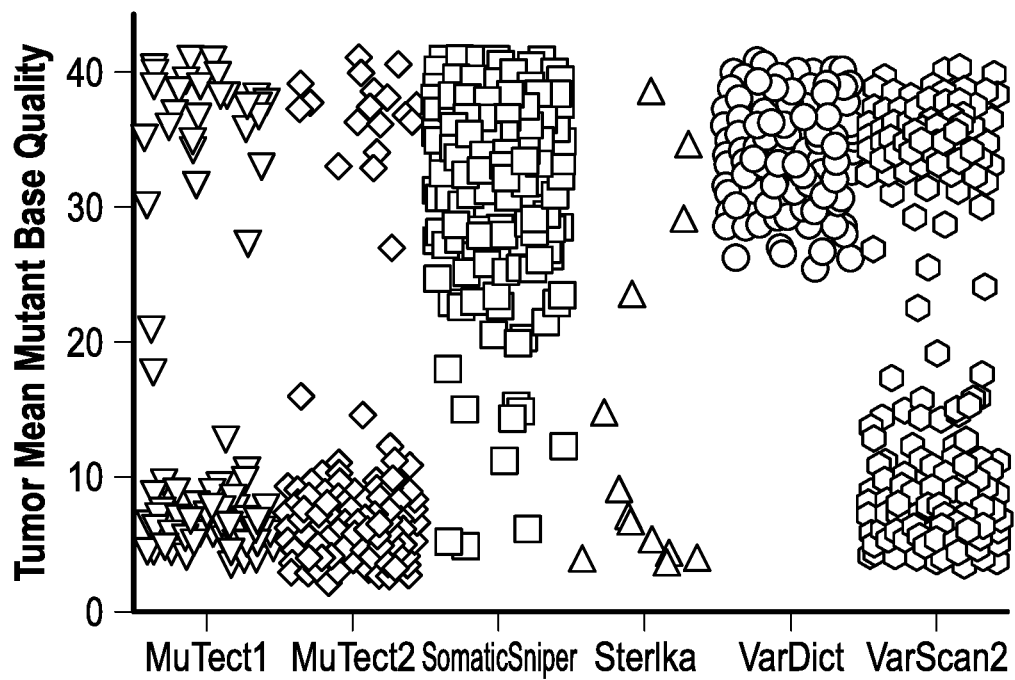
Figure 25F:
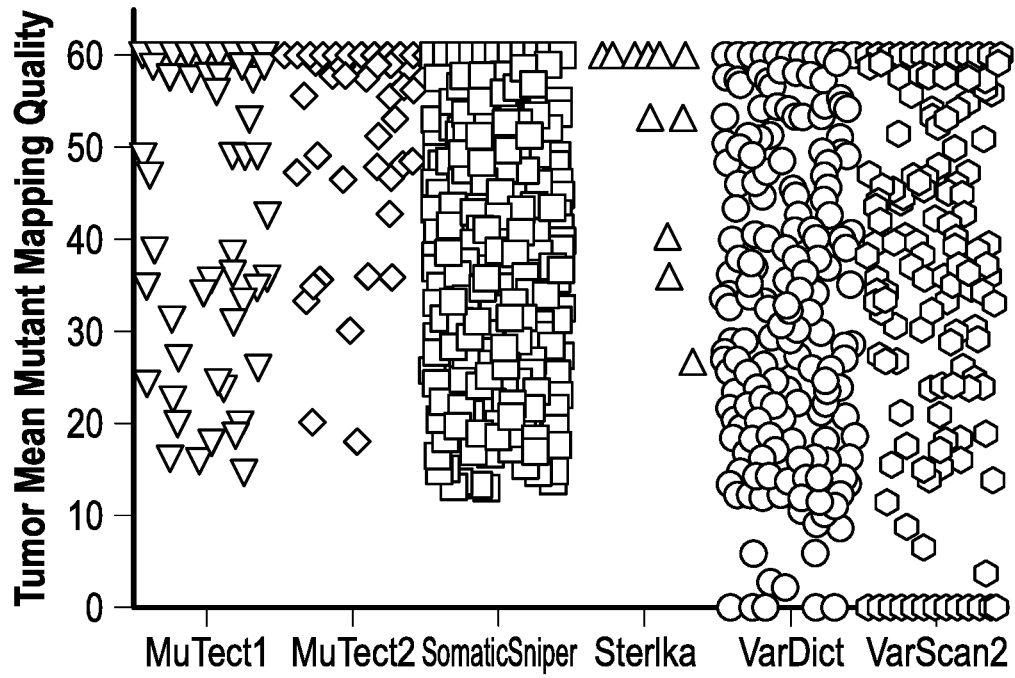

FIGS. 19-22 present an analysis of tumor mutational burden in patients treated with checkpoint blockade. Comparison of Cerebro mutation calls with published calls associated with NSCLC (left panels) or melanoma (right panels). FIG. 19 shows the unique/shared mutation status for all patients. FIG. 20 reports problematic mutations unique to original publications annotated by characteristic issue (Annotation=conflicting consequence; TDP<3=tumor distinct pairs less than 3; TBQ<30=tumor base quality less than 30; Unaligned=no alignment of mutated reads to the mutation position; MAF<5%=mutant allele frequency less than 5%). FIG. 21 is a Kaplan-Meier analysis of progression free survival (left) or overall survival (right) using tumor mutation loads from original publications. FIG. 22 is a Kaplan-Meier analysis of same samples using Cerebro mutational loads. Log-rank P-value shown for each survival plot. Among all mutations in the NSCLC set, 48.2% were concordant between Cerebro and the original report, while 61.9% of mutations in the melanoma cohort were concordant (FIG. 19). We performed an in-depth characterization of mutations that were identified in the original publications but that would be considered false positives using Cerebro and found that the large majority of such calls could be attributed to systematic issues such as limited observations of the mutation in distinct read pairs, poor base quality at the mutation position, and inaccurate alignment (FIG. 20).

Given the association of mutation load with clinical outcome in patients treated with immune checkpoint blockade, we wondered whether our analyses could be used to improve the classification of patients into mutator groups with different clinical outcomes. Cerebro analyses revealed that the average SBS mutational burdens for NSCLC and melanoma groups were 187 and 501, respectively, both substantially different than the original publications. Previously melanoma analyses were performed using SomaticSniper and led to a lower number of detected mutations, consistent with the lower sensitivity we observed with this method (FIG. 11 and FIG. 13). Utilizing the individual mutational loads from our analyses, we observed an improved prediction compared to previous mutation calls for progression free survival (P=8e-6 vs P=9e-5; NSCLC) and overall survival (P=2e-4 vs P=0.009; melanoma) (FIG. 21 and FIG. 22) for these patients. Overall, these analyses suggest that improved mutation determination may have even greater impact on clinical outcome to immune checkpoint blockade than previously anticipated.

Evaluation of Somatic Mutations in Clinical NGS Analyses

To evaluate the effect of somatic mutation detection methods on NGS clinical cancer sequencing tests, we performed replicate analyses of formalin fixed paraffin embedded (FFPE) or frozen tumor samples from 22 lung cancer patients using three separate approaches for mutational profiling: PGDx CancerSELECT 125 which utilized the Cerebro method, as well as the Thermo Fisher Oncomine Comprehensive Assay and the Illumina TruSeq Amplicon-Cancer Panel which use other mutation calling methods. For each sample, adjacent interspersed FFPE sections were evaluated at two CLIA-certified laboratories using these approaches. Samples from three patients could not be analyzed using the TruSeq Amplicon-Cancer Panel due to insufficient DNA, and were excluded from comparative analyses. Putative somatic mutations for the remaining 19 patients were used for concordance evaluation and were limited to genomic regions comprising 16.5 kbp common to all three approaches. Mutations were considered true positives if they were detected in two or more of the three assays, or if identified in only one of the assays and independently confirmed using ddPCR.

These analyses resulted in a set of true somatic mutations consisting of 30 single base substitutions (SBSs) and six insertions and deletions (indels) in commonly analyzed regions among the 19 patients (Table 2 in FIG. 24). The CancerSELECT 125 panel using Cerebro achieved 100% sensitivity for both SBSs and indels. The Oncomine assay resulted in a sensitivity of 97% for SBSs and 83% for indels. The TruSeq panel was unable to detect 15 SBSs and three indels resulting in a lower sensitivity of 50% for both types of alterations (Table 2 in FIG. 24). CancerSELECT 125, Oncomine and TruSeq approaches resulted in 0, 17, and 175 false positives, respectively. Seventeen false positive SBSs reported by the Oncomine or TruSeq panels were single nucleotide polymorphisms (SNPs) that could be identified in databases of known germline variants and had been removed by the Cerebro approach. However, the large number of false positive results identified by the TruSeq panel suggests additional underlying technical causes, including PCR artifacts and sequencing error. The high number of false positive SBSs from the TruSeq panel dramatically reduced its positive predictive value to 8% (Table 2 in FIG. 24). The CancerSELECT 125 mutation detection approach outperformed Oncomine by achieving higher sensitivity for both SBSs and indels and higher PPV for SBSs, while the TruSeq approach had poor overall performance, including limited sensitivity for both types of alterations and a high false positive rate. Due to the high number of TruSeq nongermline false positives, we performed a detailed evaluation of these candidate mutations in the NGS data obtained using the CancerSELECT 125 platform, and found no evidence of these mutations predicted by the TruSeq approach. Additionally, comparison of CancerSELECT 125 NGS data using the two mutation callers suitable for tumor-only analyses demonstrated superior sensitivity and positive predictive values for Cerebro. Overall, these analyses reveal the importance of high accuracy somatic mutation detection for identification of bona fide alterations in clinical NGS assays.

Discussion

Our studies describe the development of a machine learning approach for optimizing somatic mutation detection in human cancer. These analyses demonstrate that high accuracy mutation detection can improve identification of bona fide alterations to determine total mutational burden for the prediction of outcomes to immunotherapy, as well as to detect of alterations in potentially actionable driver genes. These data highlight the challenges of detecting somatic sequence alterations in human cancer, and provide a broadly applicable means for detecting such changes that is more accurate than existing approaches.

Our assessment of mutation calling approaches revealed that existing methods for somatic mutation detection may be significantly influenced by factors that can lead to excessive false positive and negative changes. The machine learning approach we describe here identified key features in NGS sequence data to minimize false positive calls and to improve sensitivity for bona fide alterations. We have focused on coding regions within exome or targeted analyses with >150× coverage. Although Cerebro could be used for improved analyses in these settings similar to other methods, the amount of whole genome sequencing needed to overcome issues of normal tissue contamination and subclonal alterations have resulted in whole exome or targeted analyses remaining one approach for cancer sequence analyses, particularly in the clinical setting.

Given the fundamental importance of somatic genomic alterations in human cancer, the improvements we have developed are likely to have significant implications for research and clinical analyses. Our re-analysis of TCGA and exome data from patients treated with cancer immunotherapy have identified that a substantial fraction of existing mutation calls are likely to be false positive changes associated with low quality evidence, and that many true alterations may have been missed in current databases. We estimated that 16% of alterations are likely inaccurate in current TCGA mutation databases and an additional 10% of true alterations may have been missed in these data sets. If these ratios are accurate across TCGA (with—2 million somatic mutations across 10,000 exomes), then the overall number of false positive and negative changes in TCGA is likely to be >500,000. Such discrepancies are likely to be important across a variety of additional efforts, as much of TCGA has been incorporated into mission critical databases such as COSMIC, gnomAD/ExAC, Genomic Data Commons and the International Cancer Genome Consortium.

Our analyses are likely to have significant implications for therapies utilizing genomic information, including targeted therapies and immune therapy approaches targeting mutation associated neo-antigens. Improved discrimination of bona fide alterations will facilitate development of mutation-load based predictive biomarkers for immune checkpoint blockade in as well as for understanding changes in cancer genomes during immune therapy. Development of mutation-specific vaccines and immune cell-based therapies will require high confidence identification of alterations that may be unique to individual patients.

These studies have implications beyond analyses of tumor tissues, including for example in deep sequencing of cell-free DNA (cfDNA) to identify somatic mutations in the circulation. Current approaches for cfDNA analyses utilize sequence data with over ~30,000× coverage to identify alterations with concentrations as low as 0.05%. Highly accurate analyses of such sequences will provide robust differentiation of true positive and true negative data, especially in cases without prior knowledge of sequence alterations from tumor tissue.

Our findings highlight the impact of several underappreciated dimensions of genomic data, and support the notion that clinical NGS tests will require rigorous standardization and critical evaluation from initial sample preparation through digital interpretation. If validated effectively, these approaches have the ability to expand options for the treatment and management of patients with cancer.

Materials and Methods

Processing of Exome Data with Cerebro

Reads from material sequenced were adapter masked and demultiplexed using bcl2fastq. All read data were aligned with BWA-MEM and Bowtie2 to a hg19 reference assembly of the human genome with unplaced and unlocalized contigs and haplotype chromosomes removed. Then, Cerebro identified candidate somatic mutations by examining alignments in the tumor and matched normal samples. Alignment data were filtered to remove non-primary alignment records, reads mapped into improper pairs, and reads with >6 edits. Individual bases were excluded from mutant coverage calculation if their Phred base quality was <30 in tumor samples and <20 in normal samples. Only candidate somatic variants found in both pairs of alignments (BWA-MEM and Bowtie2) were scored using our confidence scoring model. Candidate variants with somatic confidence scores <0.75, <3 distinct mutant fragments in the tumor, <10% MAF in the tumor, or <10 distinct coverage in the normal sample were removed. For our analysis of cancer immunotherapy response-associated data or, we included mutations between 5-10% MAF to compensate for the low tumor purity that appeared to be present in some samples.

For mutations found in at least 50 samples according to the COSMIC v72 database ("hotspots"), we applied relaxed cutoffs. For such hotspot mutations, we only excluded bases in the tumor sample if their Phred base quality was <20. We also only removed candidate hotspot mutations if they had somatic confidence scores <0.25, <2 distinct mutant fragments in the tumor, or <5% MAF in the tumor. Because sequence data obtained from TCGA were often less than 100 bp in length, which we found to reduce Bowtie2 alignment sensitivity for long indels, we also created a set of relaxed cutoffs for hotspots that were indels >8 bp in length. These relaxed indel hotspot filtering criteria focused only on the BWA-MEM alignments, and removed mutations with <5 distinct fragments in the tumor, a left-tailed FET p-value >0.01, <5% MAF in the tumor, or any mutant fragments in the normal sample.

Variants were further filtered for coding consequence using VEP and CCDS/Refseq removing intragenic and synonymous mutations. Finally, variants that were listed as Common in dbSNP version 138 were removed.

Processing of Exome Data with External Variant Callers

Read data were aligned with BWA-MEM to a hg19 reference assembly of the human genome with unplaced and unlocalized contigs and haplotype chromosomes removed. The Picard MarkDuplicatesWithMateCigar program was used on the resulting BAM files to find optical and PCR duplicates. Each external variant caller was run with default parameters. In the case of Strelka, we used the reported "tier 2" set of variants. Similarly to the processing with Cerebro, for all variant callers we removed variants with MAF <10%, as well as intragenic and synonymous mutations, and variants listed as Common in dbSNP138. Variants failing a caller's default set of filters were also removed. For VarDict, we also removed variants that hit either of two filters suggested by one of VarDict's authors.

Confidence Scoring Model and Training

A normal cell line (CRL-2339, ATCC) derived from peripheral blood that had undergone sample preparation and exome capture was sequenced twice. One of these sequencing runs was designated the "training tumor" and had novel variants spiked into it using BAMSurgeon. Novel coding variants were randomly generated across the exome, at MAFs ranging from 1.5625% to 100%, and were a mixture of substitutions, insertions, and deletions. The range of MAFs used for training was intended to begin well below the expected limit of detection (5% or 10% MAF) to ensure that calls near the limit would be accurate. Novel indels ranged from 1 to 18 bp in length. Additional novel indels were spiked in by locating polynucleotide tracts within the exome and inserting 1 or 2 repeat unit contractions or extensions of the tracts. After spiking the training tumor with BAMSurgeon, the read data from the training tumor were realigned with both BWA-MEM and Bowtie2, and then all candidate somatic variants supported by at least one tumor read were reported using Cerebro. Candidate somatic variants found in both pairs of alignments formed the training set for the scoring model.

For each candidate somatic variant, Cerebro reports several alignment and sequence quality statistics. Each of these are calculated for the two sets of alignments, and are concatenated together to form a feature vector for a candidate somatic variant. The training set for the scoring model consists of the feature vectors for each candidate variant, and a labelling indicating whether or not the variant was spiked into the training tumor (i.e., if the candidate is a somatic variant or not). The scoring model itself is an extremely randomized trees model with 1000 decision trees, implemented using the scikit-learn library (see Pedregosa et al., Scikit-learn: Machine learning in Python. Journal of Machine Learning Research 12, 2825-2830 (2011), incorporated by reference), with the reported confidence score being the percentage of the model's trees that would classify the variant as somatic.

Validation of Somatic Variants

We analyzed 5 matched tumor/normal breast cancer cell line pairs in which several hundred somatic variants had previously been identified and validated through Sanger sequencing analyses. To add to this set, we performed exome sequencing of the cell lines using the Illumina HiSeq 2500. We then analyzed the Illumina data through 3 variant calling program (VarDict, MuTect 1, and our Cerebro pipeline). Somatic variants called by all three programs were considered to be validated. Somatic variants called by 1 or 2 of those programs with a reported MAF of at least 20% (by at least one program) were visually inspected for alignment artifacts. Those variants passing visual inspection and having at least 10 reads covering the locus in the normal sample were then tested using digital droplet PCR, and variants validated by ddPCR formed the remainder of our validated variant set.

Evaluation of Variant Caller Accuracy

For simulated datasets, true positives (TP) were those spiked-in somatic variants found by a program, false positives (FP) were variants called by a program that were not spiked-in, and false negatives (FN) were spiked-in variants not called by a program. For these simulated datasets, sensitivity is defined as TP/(TP+FN), positive predictive value (PPV) as TP/(TP+FP), and false positive rate is the number of false positives reported per megabase of the exome (51.5 Mbp). For the cell line datasets, we created a validated variant set as described above, and selected those variants called by at least one caller as having a MAF of at least 20%; these selected variants created the validated comparison set. When evaluating the variant callers on cell line data: TP were comparison variants found by a program; FP were variants not in the comparison set that were called by a program with a MAF of at least 20%; and FN were comparison variants not found by a program. Because we only validated variants reported to have a MAF of at least 20%, we define PPV for the cell line data as X/(X+FP), where X is the number of TP variants that a program claimed had a MAF of at least 20%. This approach allows us to compensate for the variation in reported allele frequency between variant calling programs by restricting PPV calculation to only those variants that a program reported as being over the validation MAF threshold of 20%.

Simulation Experiments

We performed three simulation experiments, designed to evaluate the accuracy of the various variant calling programs. In each experiment, we used a set of simulated tumor/normal pairs created by sequencing 6 exome-captured normal cell lines twice to create 6 sample pairs; one of the samples in each pair was designated the "tumor", and both samples were aligned to the human genome using Bowtie2. Depending on the experiment, a set of artificial coding somatic variants were inserted into the tumors using BAM-Surgeon. After BAMSurgeon was run, the read sequence data was extracted from the modified BAM file, and the resultant FASTQ data were aligned again using the methods described in our "Processing of exome data with Cerebro" and "Processing of exome data with external variant callers" sections above.

Our first simulation experiment was designed to simulate low purity tumors, with 120 single base substitutions and 12 indels inserted into each tumor at MAFs ranging from 10-25%. In this final simulation, we evaluated several accuracy metrics, including sensitivity, PPV, FPR, and F-score. The second experiment was solely a test of specificity, where we did not insert any somatic variants into our simulated tumor; this examination of somatic variant calling specificity with technical replicates is similar to that discussed by Saunders et al. in their presentation of Strelka (see Saunders et al., Strelka: accurate somatic small-variant calling from sequenced tumor-normal sample pairs. Bioinformatics 28, 1811-1817 (2012), incorporated by reference).

In our final simulation experiment, in which we focused on sensitivity, we inserted 7,000 coding variants, consisting of 1,000 single base substitutions and 6,000 indels (1,000 each of 1, 2, & 3 bp insertions, and 1, 2, & 3 bp deletions). The second experiment's variants were inserted at MAFs ranging from 10-100%.

ddPCR Methods

Droplet digital PCR forward and reverse primers as well as wild type and mutant probes were created using the Bio-Rad ddPCR Custom Design Portal. Genomic DNA corresponding to 10,000 genome equivalents was added to 10 ul 2× ddPCR Supermix (Bio-Rad), 1 ul 20× target primers and probe (FAM), 1 ul 20× reference primers and probe (HEX), and brought to a 22 ul volume with nuclease free water to create a reaction mix. A DG8 cartridge in a DG8 cartridge holder (Bio-Rad) was loaded with 20 ul of reaction mix and 70 ul Droplet Generation Oil (Bio-Rad). The cartridge was placed in a QX200 Droplet Generator to generate approximately 20,000 nanoliter sized droplets. Droplets were loaded into a twin-tec 96 well, semi skirted plate (Eppendorf) and sealed with a foil heat seal using a PX1 PCR Plate Sealer (Bio-Rad).

Subsequent PCR cycling was performed on a C1000 Touch Thermal Cycler (Bio-Rad) with the following conditions: 95° C. for 10 minutes, followed by 40 cycles of 94° C. for 30 seconds and 55° C. for 1 minute, and ending with 98° C. for 10 minutes. The plate was then loaded on a QX200 Droplet Reader (Bio-Rad) and PCR positive and negative droplets were quantified. Raw droplet data was analyzed with QuantaSoft software (Bio-Rad). Thresholds were manually assigned using 2D amplitude clustering plots and the crosshair tool for each tumor and normal pair. Tumor samples were run in duplicate and the average mutant allele fraction was taken. For the comparative evaluation of clinical targeted sequencing panels, there were some modifications to the ddPCR protocol. 5,500 genome equivalents were used, and 1 ul of a 20× mixture of target primers and probes and reference primers and probes (FAM and HEX respectively) were used (Bio-Rad). As there were no matched normal samples, wild type and mutant oligomers were designed as controls for each target investigated (Operon Biotechnologies).

WES Data Extraction and Annotation

The results shown here are in part based upon data generated by the TCGA Research Network as outlined in the TCGA publications guidelines. TCGA WES datasets (bam alignment files) represented untreated primary tumors and paired normal tissue samples obtained from the Cancer Genomics Hub. WES-derived somatic mutation calls were obtained from the MC3 Project TCGA somatic mutation calls (v0.2.8) were also obtained from the Synapse repository.

Variant supporting coverage and total coverage were extracted and manually reviewed for consistency. To normalize across cancer types, mutations with fewer than three variant-associated reads or less than 10% mutant allele frequency were filtered prior to downstream comparative analysis. For mutations found in at least 50 samples according to the COSMIC v72 database ("hotspots"), we allowed for 5% minimum mutant allele frequency. Additional somatic mutation call sets generated by MuTect2 were downloaded from the Genomic Data Commons and also Broad GDAC Firehose using the firehose get download client prioritizing the BIFIREHOSE Oncotated Calls somatic mutation call sets compiled from various TCGA Genome Sequencing Centers' bioinformatics pipelines. For comparisons of Cerebro to other call sets, included mutations were required to fall within a common ROI set. The source of the primary mutation calling tools used for each cancer type may be found in the corresponding TCGA marker publications. Concordance analysis of somatic mutations from 66 oncogenes and tumor suppressor genes included manual review to determine shared status of mutations within the same or adjacent codons. Whole-exome melanoma or NSCLC immunotherapy datasets are available via NCBI dbGaP (accessions phs000980 and phs001041).

Clinical Study Design and Analysis

Twenty-two total samples, seventeen formalin fixed paraffin embedded (FFPE) and five frozen tumor tissue specimens obtained from lung cancer patients were procured from ILSBio/Bioreclamation and analyzed for the presence of sequence mutations using three targeted cancer gene panels from independent vendors. All samples were obtained under Institutional Review Board—approved protocols with informed consent for research use at participating institutions. One set of patient samples was processed and analyzed for sequence mutations by Personal Genome Diagnostics (Baltimore, MD) using the CancerSELECT 125 panel. In brief, samples were reviewed by a pathologist to determine the percent tumor purity followed by macrodissection and DNA extraction. DNA was fragmented and used for CancerSELECT 125 library preparation and capture. Libraries were sequenced using HiSeq2500 instruments (Illumina) Sequencing output was analyzed and mutations identified using Cerebro. An identical set of FFPE and frozen tumor tissue specimens were sent to MolecularMD (Portland, OR) along with a hemotoxylin and eosin stained image for processing and next-generation sequencing analysis using two cancer specific panels supplied by two independent vendors: Oncomine Comprehensive Assay (ThermoFisher) and TruSeq Amplicon-Cancer Panel (Illumina). To limit the effects of tumor heterogeneity on analysis, slides were distributed in non-sequential order for testing. For orthogonal analysis, comparisons were limited to regions of interest (ROI) that were included in all three panels. Samples that failed quality check in one or more panels were excluded. A sequence mutation was considered a True Positive (TP) if there was positivity in at least two panels and a False Positive (FP) if only detected in one panel. Sequence mutations were considered True Negatives (TN) if there was negativity in at least two panels. A position with no mutation detected was considered a False Negative (FN) in a panel if that position was concordantly positive in the other two panels. Genomic positions that were masked based on known single nucleotide polymorphisms (SNPs) in the CancerSELECT 125 panel were considered FP in Oncomine and TruSeq analyses. As there were >150 FPs detected with the TruSeq panel, discordant resolution was limited to FPs or FNs obtained by CancerSELECT 125 and Oncomine (not considered SNPs) and were resolved using ddPCR.

Statistical Methods

The Mann-Whitney U test was employed to compare quantitative measures (e.g., nonsynonymous mutational load) between groups of interest. Comparisons of relative frequencies utilized Fisher's exact test. The log-rank test was used to evaluate significant differences between Kaplan-Meier curves for overall survival or progression free survival in the Melanoma (see Snyder et al., Genetic basis for clinical response to CTLA-4 blockade in melanoma, N Engl J Med 371, 2189-2199 (2014), incorporated by reference) or NSCLC (see Rizvi et al., Cancer immunology: Mutational landscape determines sensitivity to PD-1 blockade in non-small cell lung cancer, Science 348, 124-128 (2015), incorporated by reference) immunotherapy datasets, respectively. Confidence intervals (95% CIs) for proportions in clinical NGS comparisons were calculated using the method described by Wilson and Newcombe with no continuity correction (see Newcombe, Two-sided confidence intervals for the single proportion: comparison of seven methods, Stat Med 17, 857-872 (1998) and Wilson, Calculating a confidence interval of a proportion, J Am Stat Assoc 22, 209-212 (1927), both incorporated by reference).

FIGS. 25A-F show false position evaluation for somatic mutation callers. In particular, using results from simulated mutations in exomes, we display factors frequently associated with false positive mutation calls including tumor/normal coverage, tumor/normal mutant allele frequency (MAF), mean mutant base quality and mean mutant mapping quality. Each point shown in the figures represents a false positive mutation called by a specific program.

Figure 26A:
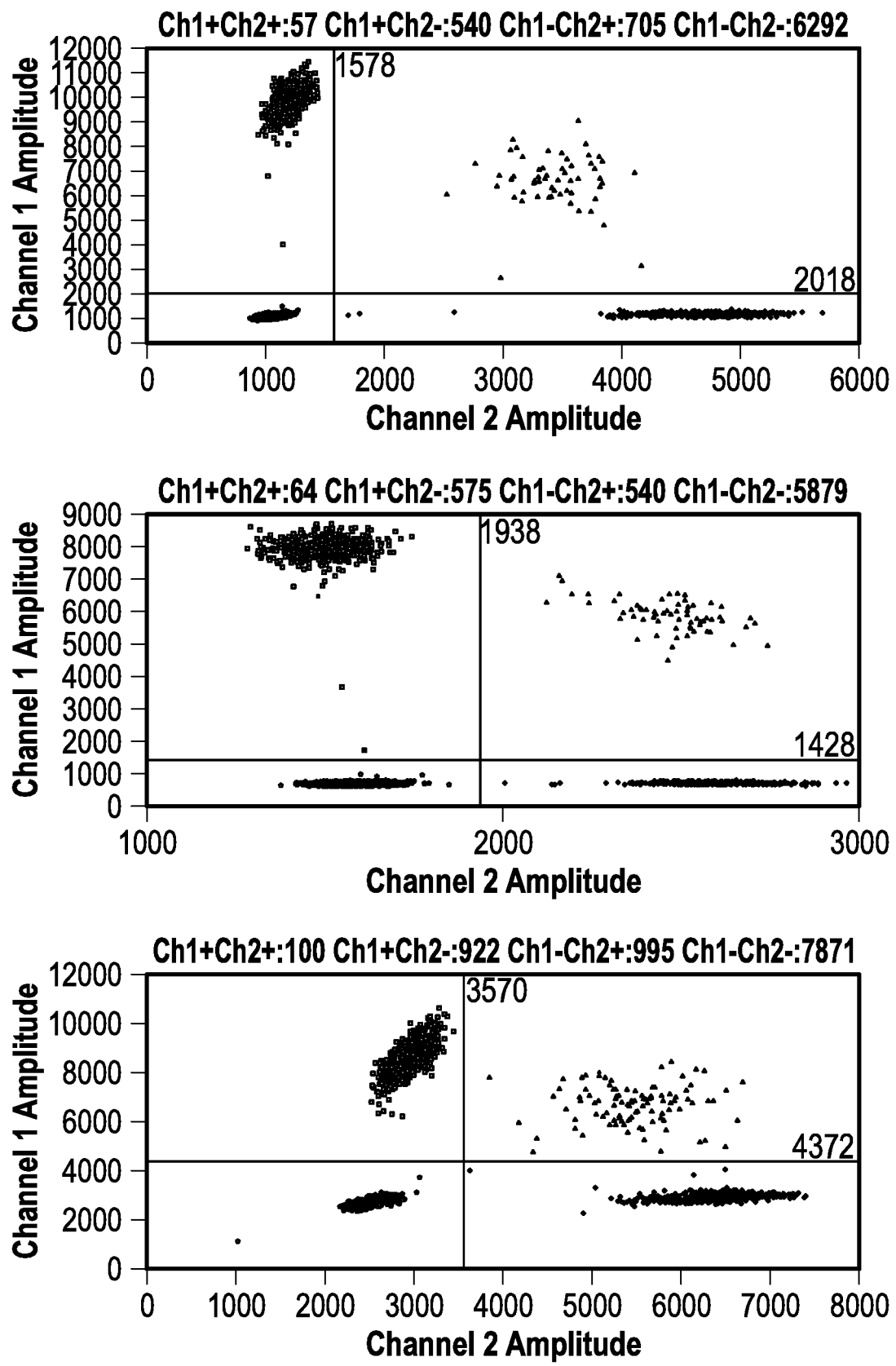
FIG. 26A-26B illustrates the results of droplet digital PCR mutation validity analyses.
Figure 26B:
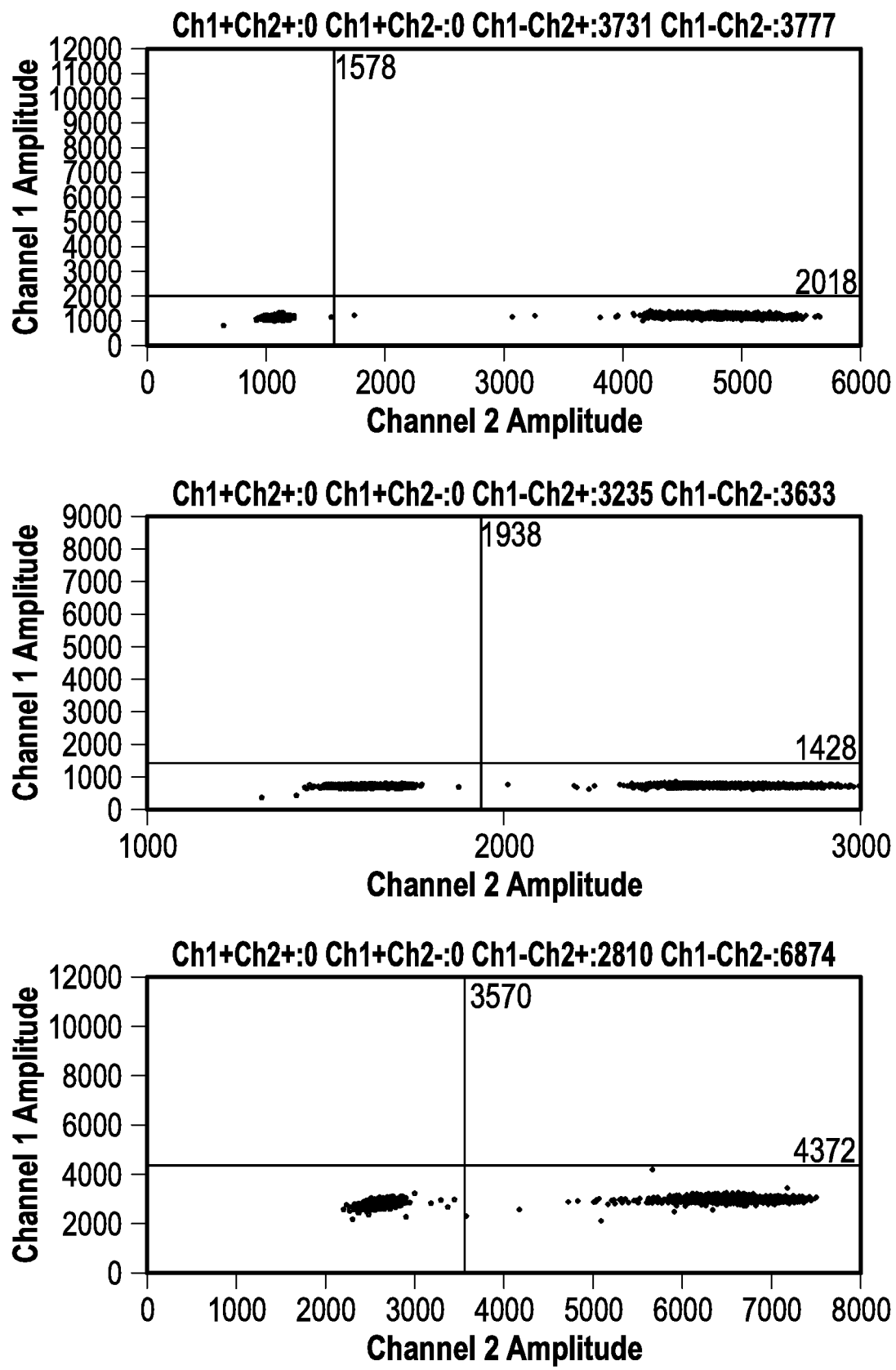
Figure 26B:
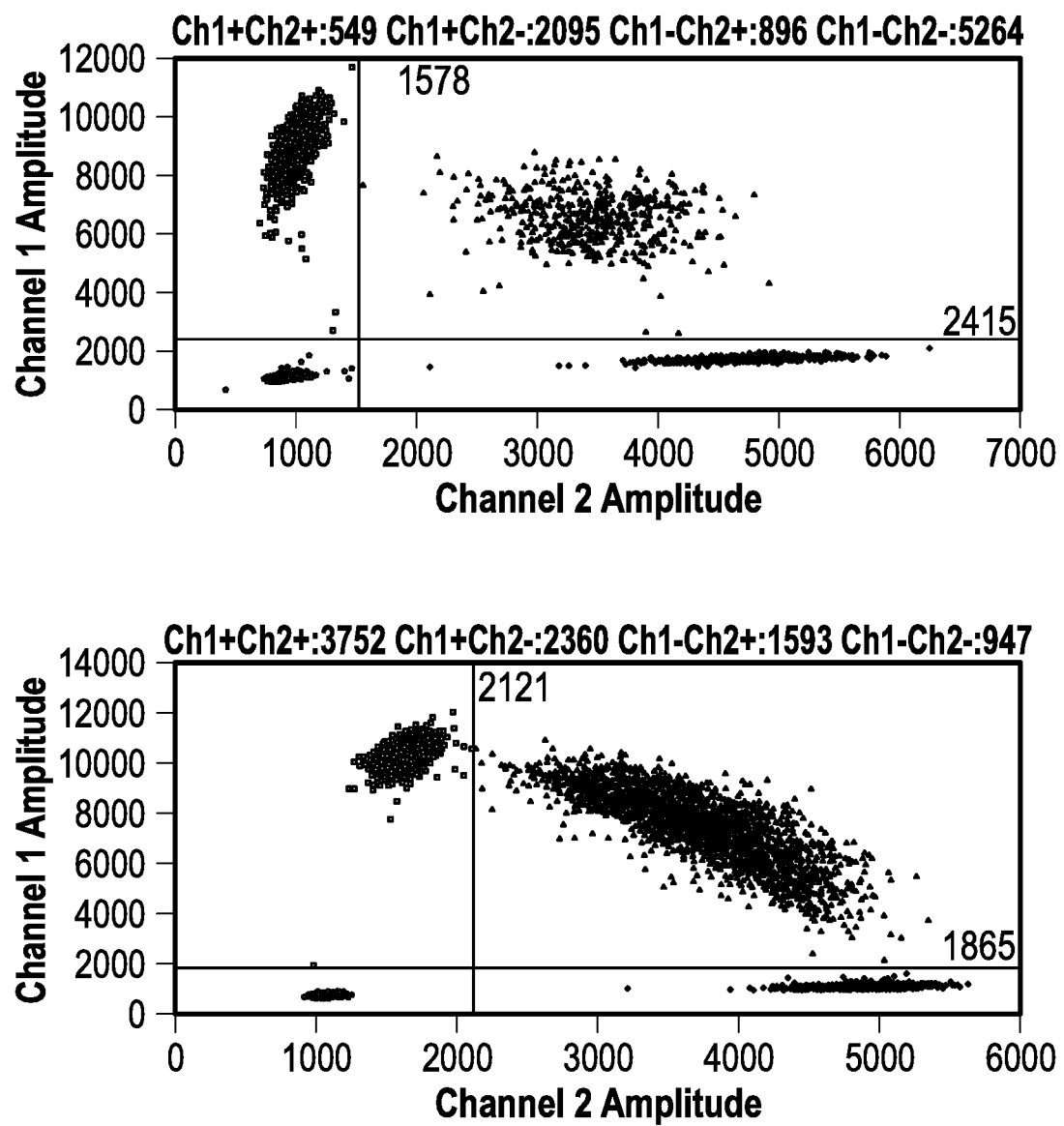

FIG. 26 illustrates the results of droplet digital PCR mutation validity analyses. Each panel in FIG. 26 is a unique sample and each point on the graphs represents the fluorescent signal from PCR amplified fragments in a droplet. Green droplets have been fluorescently tagged with reference a reference probe (HEX), blue droplets have been tagged with a mutant probe (FAM), and orange droplets have been tagged with both mutant and reference probes. Rows correspond to a variant where both the tumor and matched normal sample were tested. (A) Somatic mutations validated by ddPCR. In each case, the tumor shows amplified mutant copies (blue) while the normal only shows amplified reference copies (green). (B) Germline and false positive variants. For the top three rows, mutant copies (blue) amplified in both the tumor and matched normal sample, meaning these variants are germline. The bottom two variants have only reference amplification (green) in both the tumor and normal, meaning these variants were false positive calls by NGS.

Figure 27A:
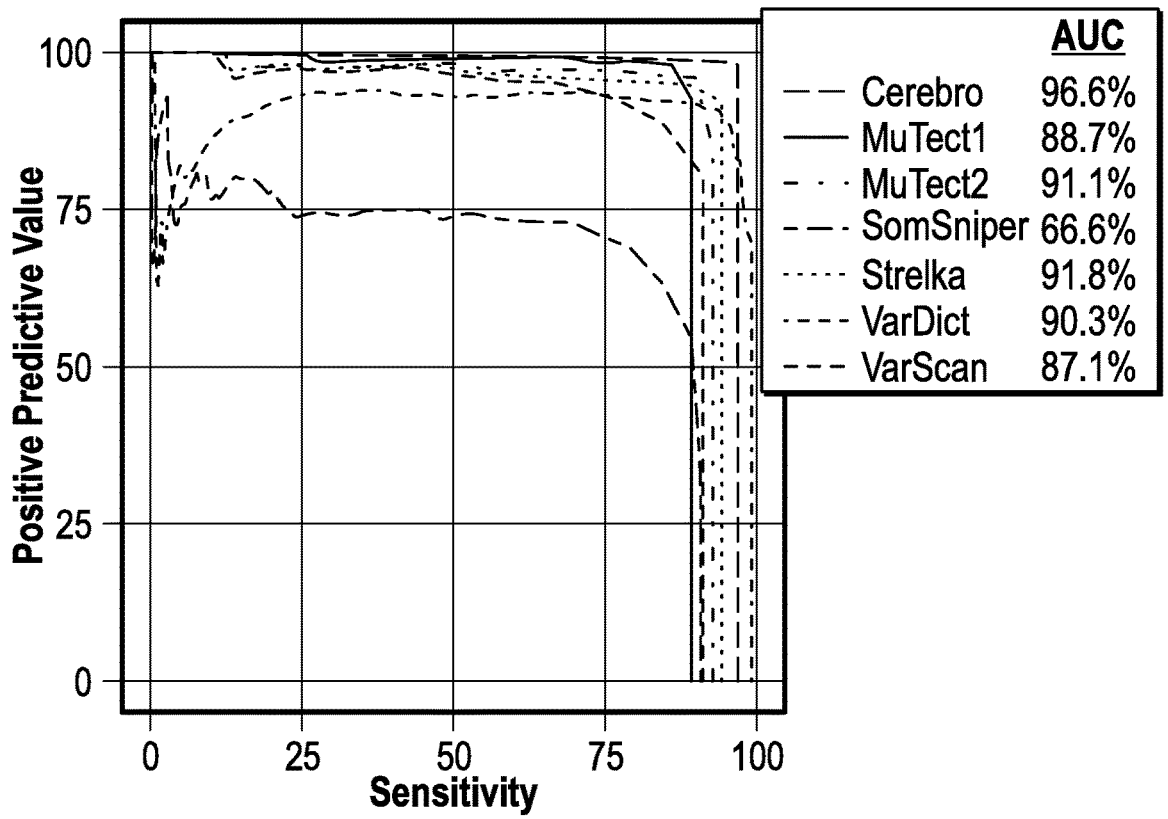
FIGS. 27A and 27B illustrate curve analyses for Cerebro and other mutation callers using experimentally validated alterations.
Figure 27B:
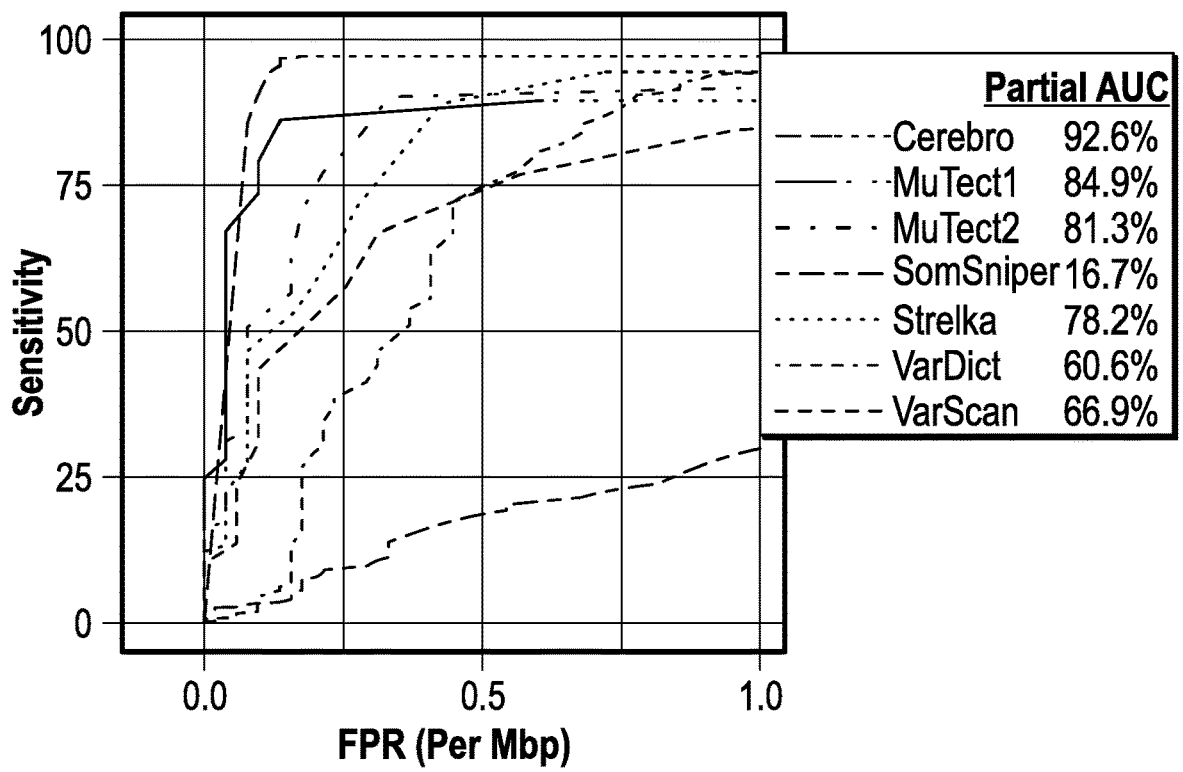

FIGS. 27A and 27B illustrate curve analyses for Cerebro and other mutation callers using experimentally validated alterations. In particular, precision-recall and ROC curve analyses of Cerebro and other mutation callers using experimentally validated alterations are shown. We observe that Cerebro outperforms other methods using both precision-recall (A, sensitivity vs. positive predictive value) and ROC analyses (B, false positive rate (per Mbp) vs. sensitivity).

Figure 28:
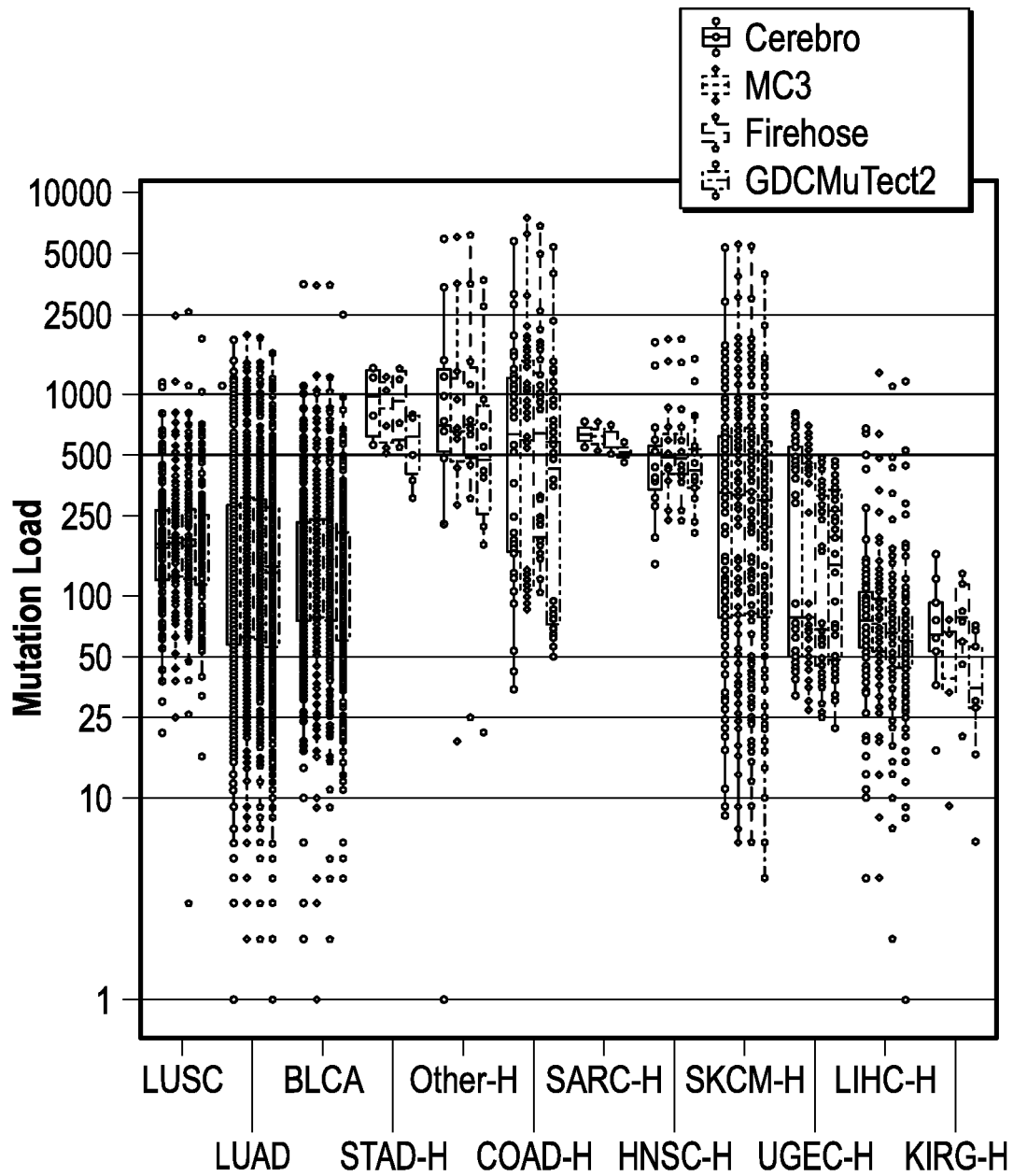
FIG. 28 illustrates mutation loads for TCGA exomes using different mutation calling methods.

FIG. 28 illustrates mutation loads for TCGA exomes using different mutation calling methods. The call sets include Cerebro, MC3 (PanCanAtlas), Broad Firehose, and MuTect2 (Genomic Data Commons). The acronyms along the bottom of the chart are LUSC=lung squamous cell carcinoma; LUAD=lung adenocarcinoma; BLCA=bladder; STAD=stomach; COAD=colorectal; SARC=sarcoma; HNSC=head and neck squamous cell; SKCM=melanoma; UCEC=uterine; LIHC=liver; KIRC=kidney; *–H=set enriched for high mutation load samples.

Figure 29:
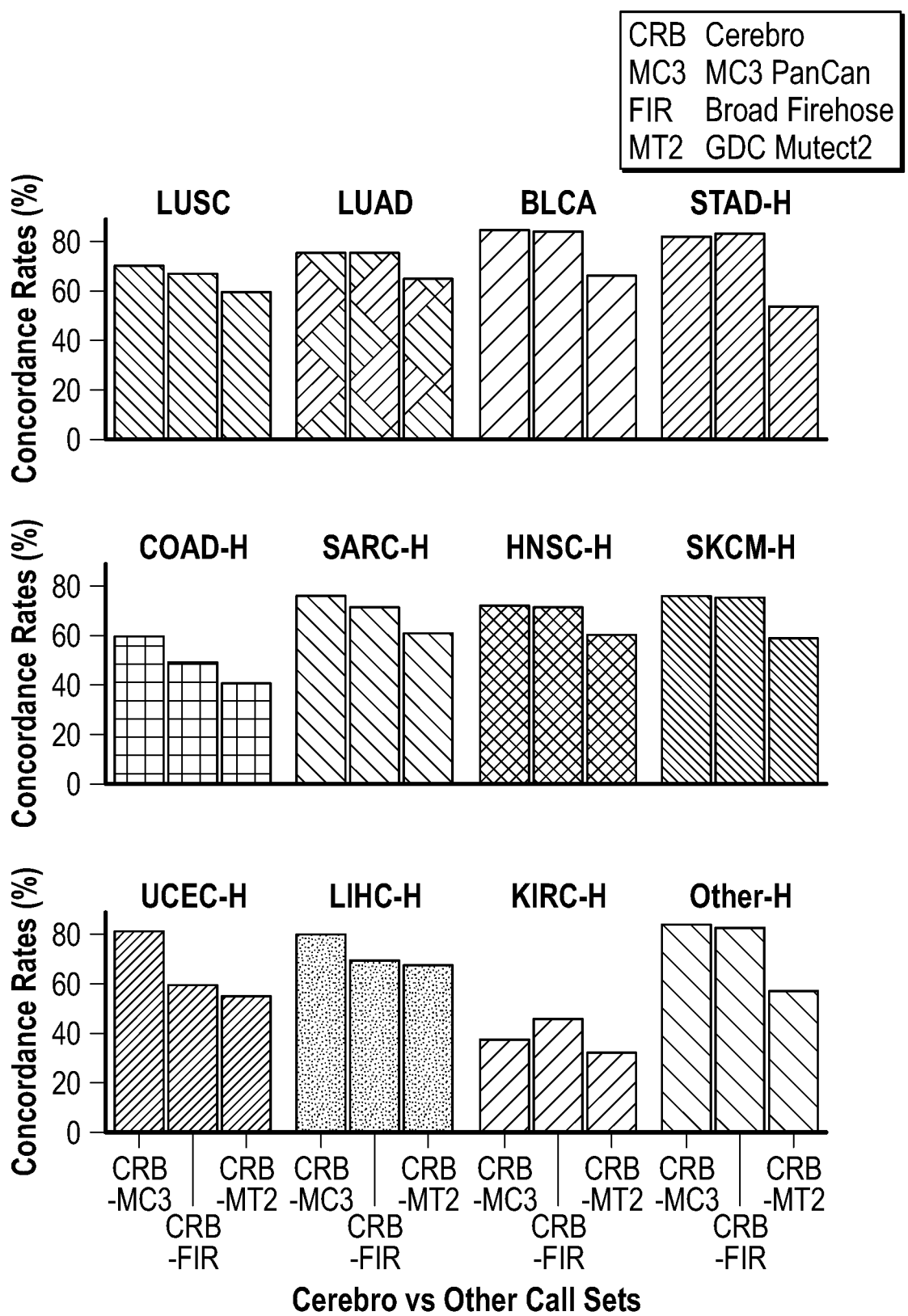
FIG. 29 illustrates concordance rates of Cerebro compared to other mutation call sets for TCGA exomes.
Figure 30B:
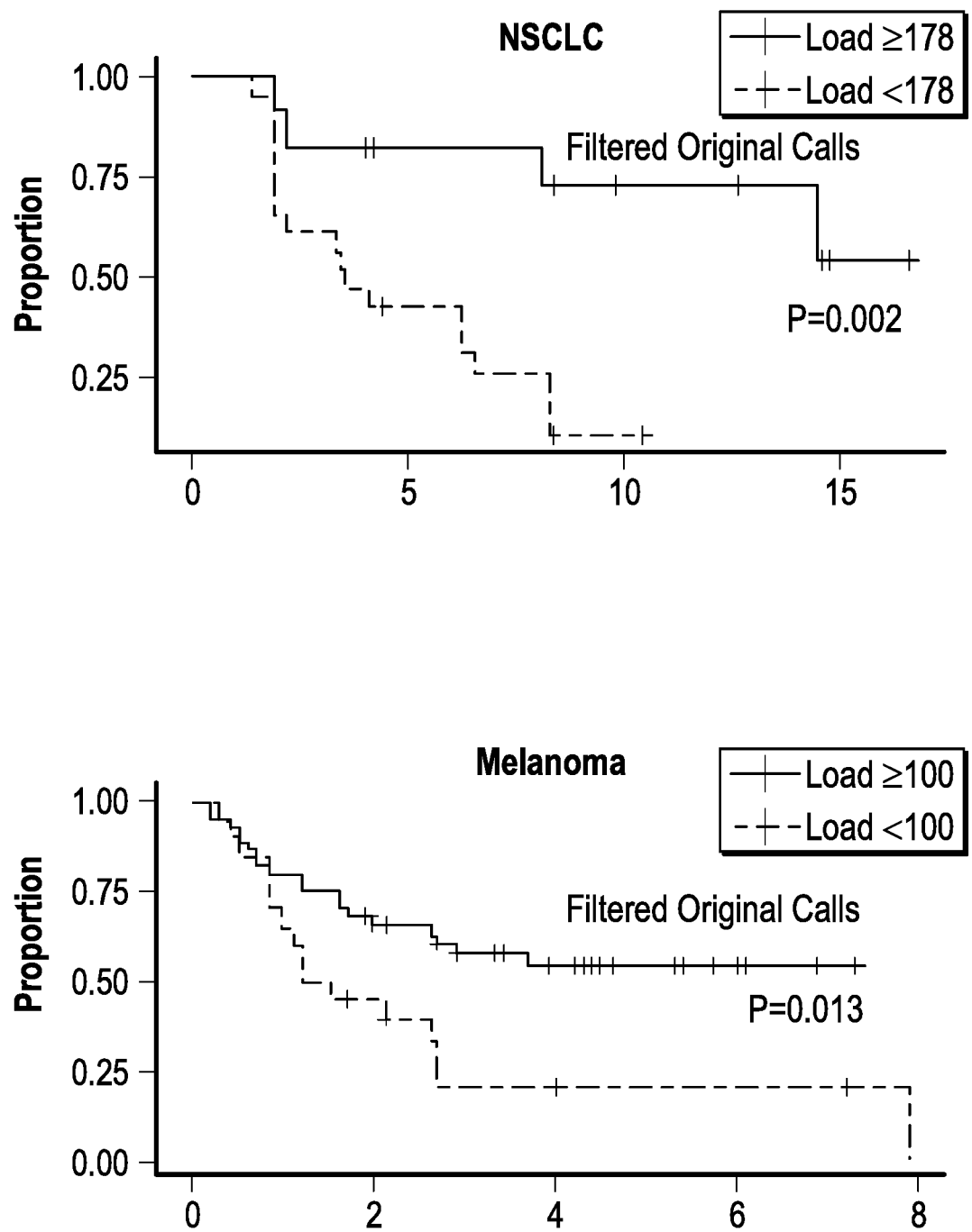
Figure 30D:
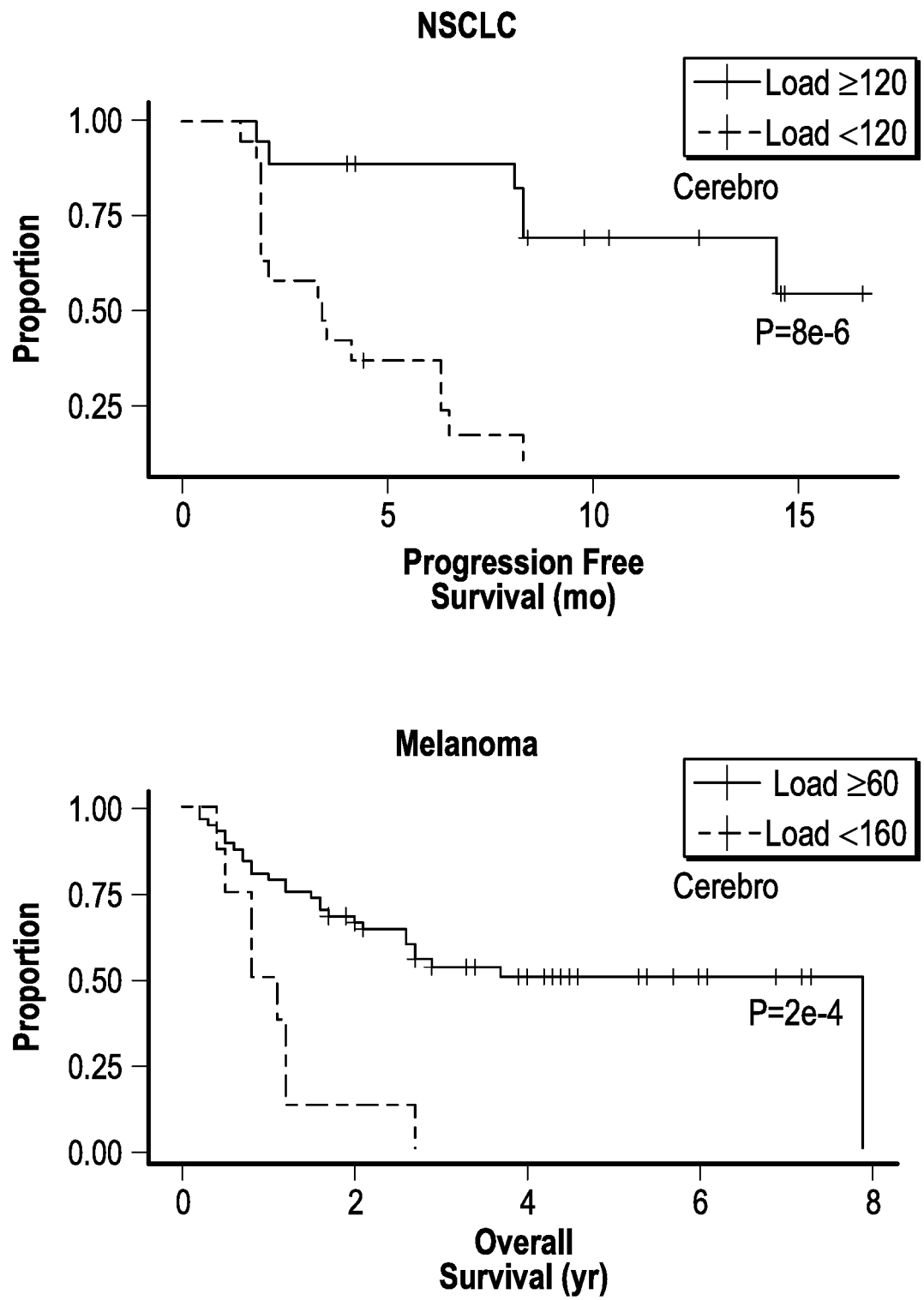

FIG. 29 illustrates concordance rates (percentage of total mutations) of Cerebro compared to other mutation call sets for TCGA exomes. The acronyms along the bottom of the chart are LUSC=lung squamous cell carcinoma; LUAD=lung adenocarcinoma; BLCA=bladder; STAD=stomach; COAD=colorectal; SARC=sarcoma; HNSC=head and neck squamous cell; SKCM=melanoma;

UCEC=uterine; LIHC=liver; KIRC=kidney; *-H=set enriched for high mutation load samples.

FIGS. 30A-30D illustrate comparison of Cerebro mutation calls with published calls and a response to checkpoint inhibitors associated with mutational load. The figures show a comparison of Cerebro mutation calls with published calls associated with NSCLC (left panels) or melanoma (right panels). (A) Kaplan-Meier analysis of progression free survival (left) or overall survival (right) using tumor mutation loads from original publications; (B) original publication results filtered for problematic mutations; (C) Cerebro calls using same threshold as original publications; (D) Cerebro calls using optimal thresholds for survival prediction. Log-rank P-value shown for each survival plot.

Figure 31:
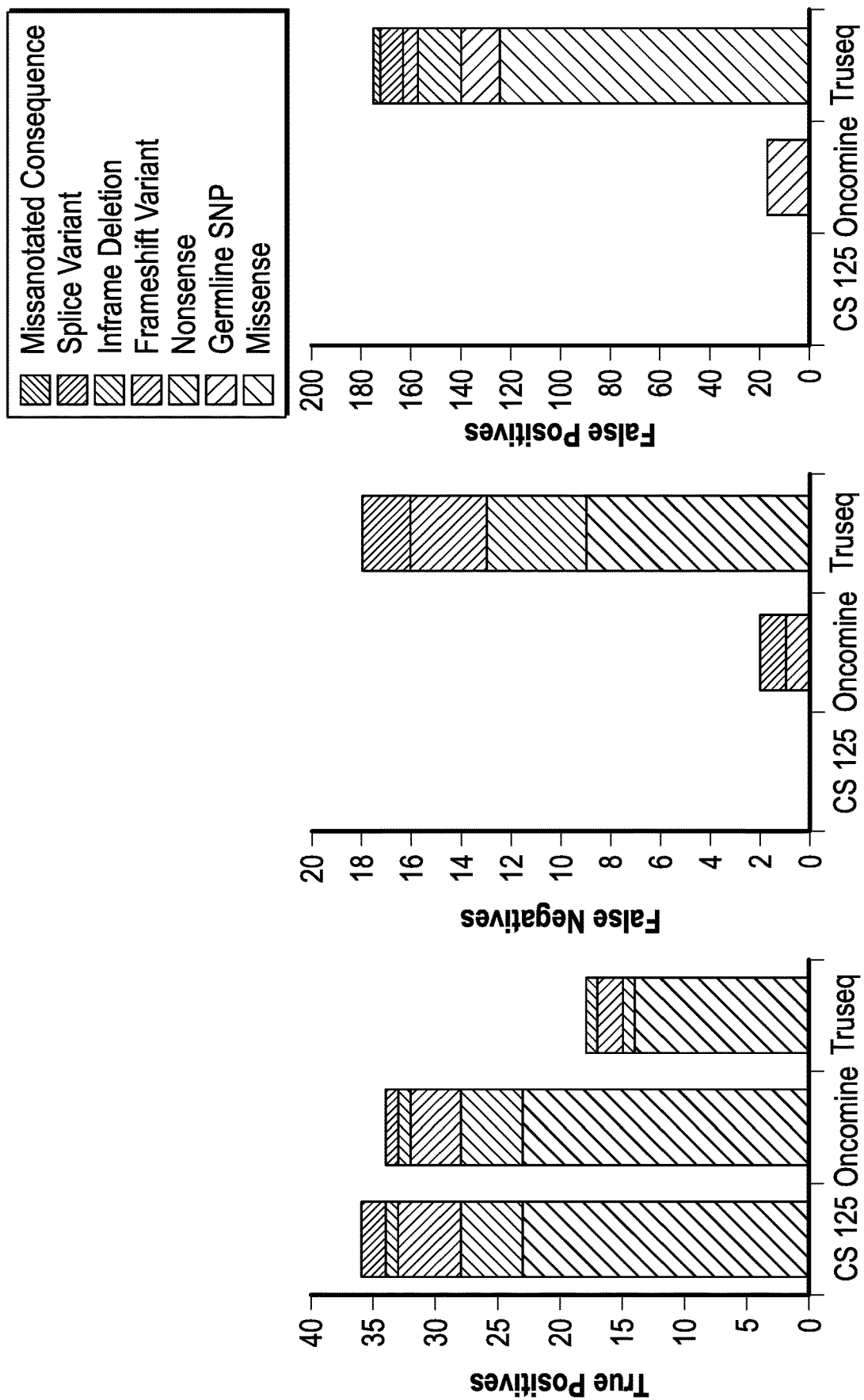
FIG. 31 illustrates comparative results of three clinical sequencing panels.

FIG. 31 illustrates comparative results of three clinical sequencing panels. The reported results include true positives, false negatives and false positives.

Figure 32A:
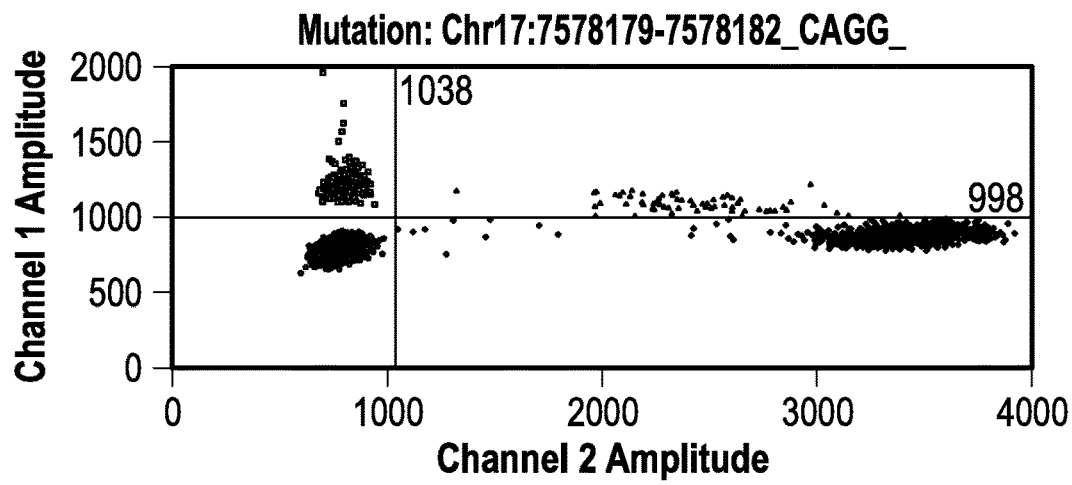
FIGS. 32A-32C illustrate alterations confirmed by ddPCR in a clinical panel comparison.
Figure 32B:
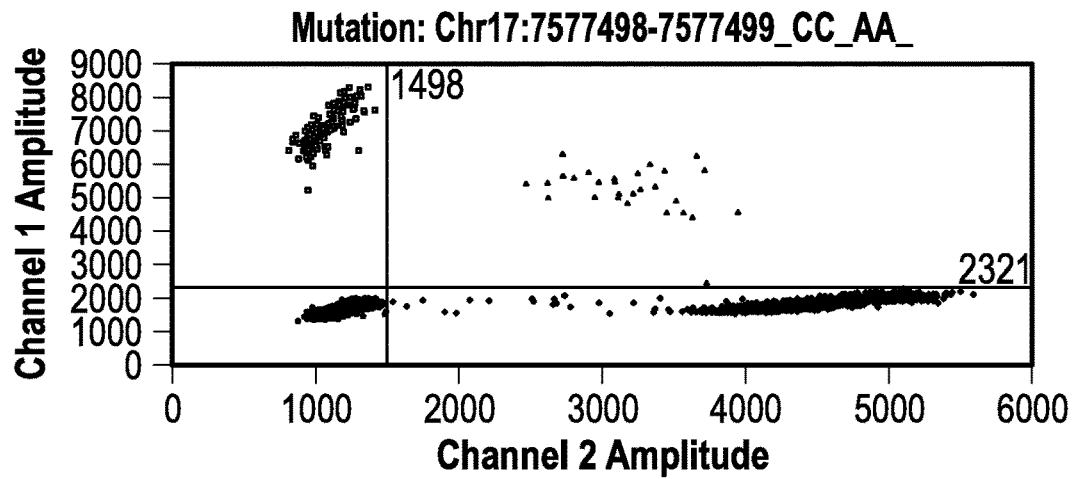
Figure 32C:
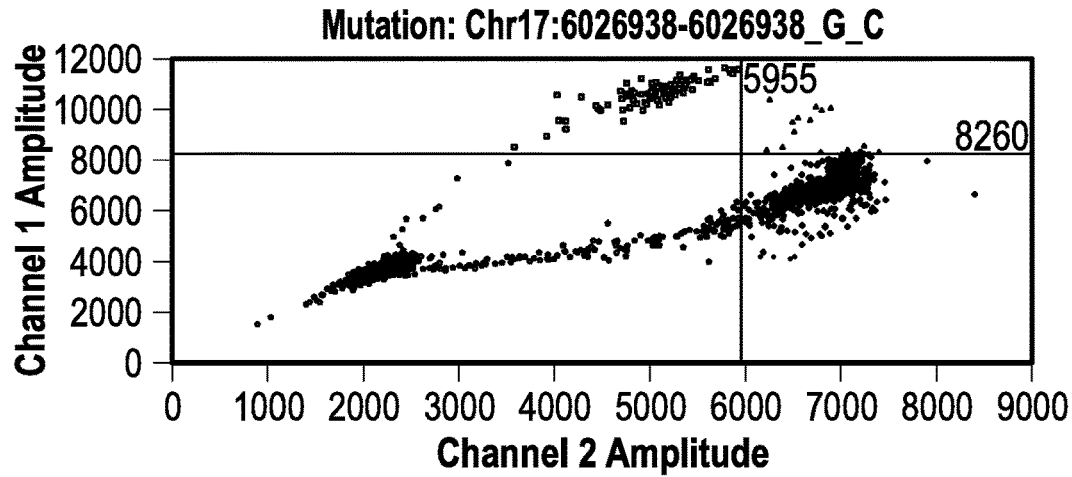

FIGS. 32A-32C illustrate alterations confirmed by ddPCR in a clinical panel comparison. Each panel is a unique sample and each point on the graphs represents the fluorescent signal from PCR amplified fragments in a droplet. Green droplets have been fluorescently tagged with reference a reference probe (HEX), blue droplets have been tagged with a mutant probe (FAM), and orange droplets have been tagged with both mutant and reference probes.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A method for identifying somatic mutations from cell free DNA (cfDNA) isolated from a patient sample, the method comprising:
analyzing the patient sample by amplifying cfDNA from the sample to generate multiple copies of nucleic acid sequences and performing whole exome sequencing analysis and variant calling on the multiple copies of nucleic acid sequences to identify a candidate variant, wherein the identifying the candidate variant further provides features associated with the exome sequencing analysis and the variant calling;
evaluating, using a computer having a machine learning classifier, the candidate variant and the features against a random forest classifier comprising at least one thousand decision trees trained to detect somatic mutations in the candidate variant, wherein each decision tree evaluates a unique combination of selected information supporting the candidate variant and classifies the candidate variant as somatic or not somatic, and wherein the machine learning classifier generates a confidence score that represents a proportion of the decision trees that would classify the candidate variant as somatic and a final classification of the candidate variant as somatic or not somatic based on the confidence score; and
generating, using the computer, a report that describes the candidate variant as somatic or not somatic based on the evaluating.

2. The method of claim 1, wherein the at least one thousand decision trees comprise a plurality of decision trees for each mutation.

3. The method of claim 1 further comprising training the machine learning classifier using a training data set of sequences that include known mutations or structural alterations.

4. The method of claim 3, wherein training the machine learning classifier comprises optimizing parameters of the machine learning classifier until the machine learning classifier produces output describing the known mutations and/or structural alterations.

5. The method of claim 4, wherein optimizing parameters of the machine learning classifier comprises selecting a plurality of feature categories.

6. The method of claim 3, wherein the training data set comprises a plurality of known single-nucleotide variants (SNVs), the method comprising:
detecting at least one SNV in the cfDNA;
validating the detected SNV as present in the cfDNA using a classification model; and
providing a report that describes the cfDNA as including the SNV.

7. The method of claim 1, further comprising providing a report that describes the candidate variant as including the mutation or structural alteration.

8. The method of claim 7, wherein describing the structural alteration comprises:
comparing the sequence reads to a reference to detect an indicia of the structural alteration; and validating the structural alteration as present in the cfDNA using a classification model.

9. The method of claim 1, wherein one or more of the decision trees receive parameters selected from the group consisting of: sample type; FASTQ quality score; alignment score; read coverage; and an estimated probability of error.

10. The method of claim 1, wherein classifying the candidate variant comprises detecting at least one boundary of a structural alteration by a set of steps selected from (a) and (b):
   (a) sequencing a fragment of the cfDNA by paired-end sequencing to obtain a pair of paired-end reads, and mapping the pair of paired end reads to a reference, wherein when the pair of paired-end reads exhibit a discordant mapping to the reference, the fragment includes the boundary; and
   (b) sequencing the cfDNA to determine a plurality of sequence tags, mapping the tags to the reference, and determining tag densities of mapped tags along portions of the reference, wherein when a portion of the reference exhibits an anomalous tag density a large indel is detected in a corresponding portion of the cfDNA from the sample, wherein an end of the indel corresponds to the boundary of the structural alteration.

11. The method of claim 1, wherein a decision tree classifies the candidate variant as germline.

12. The method of claim 1, wherein each decision tree evaluates a unique combination of information supporting the candidate variant.

13. The method of claim 12, wherein the supporting information is selected from the group consisting of a plurality of alignment characteristics, sequence quality information, information related to alterations and any combination thereof.

14. The method of claim 13, wherein the plurality of alignment characteristics comprises mapping quality and mismatches, the sequence quality information comprises coverage and base quality, and the information related to alterations comprise allele frequency, nearby sequence complexity, and presence of an alteration in a matching normal specimen.

15. The method of claim 1, further comprising, displaying on a user interface connected to an output device, a report that describes the candidate variant as including the mutation or structural alteration.

16. A system for identifying somatic mutations from cell free DNA (cfDNA) isolated from a patient sample, comprising:
   a computer system having a processor, memory and a plurality of lines of instructions; and
   a machine learning classifier executed by the processor of the computer system, the machine learning classifier being configured to:
      analyzing the patient sample by amplifying cfDNA from the sample to generate multiple copies of nucleic acid sequences and performing whole exome sequencing analysis and variant calling on the multiple copies of nucleic acid sequences to identify a candidate variant, wherein the identifying the candidate variant further provides features associated with the exome sequencing analysis and the variant calling;
      evaluating the candidate variant and the features against a random forest classifier comprising at least one thousand decision trees trained to detect somatic mutations in the candidate variant, wherein each decision tree evaluates a unique combination of selected information supporting the candidate variant and classifies the candidate variant as somatic or not somatic, and wherein the machine learning classifier generates a confidence score that represents a proportion of the decision trees that would classify the candidate variant as somatic and a final classification of the candidate variant as somatic or not somatic based on the confidence score; and
      generating, using the computer, a report that describes the candidate variant as somatic or not somatic based on the evaluating.

17. The system of claim 16, wherein the at least one thousand decision trees comprise a plurality of decision trees for each mutation.

18. The system of claim 16, wherein the processor is further configured to train the machine learning classifier using a training data set of sequences that include known mutations or structural alterations.

19. The system of claim 18, wherein the processor is further configured to optimize parameters of the machine learning classifier until the machine learning classifier produces output describing the known mutations and/or structural alterations.

20. The system of claim 19, wherein the processor is further configured to select a plurality of feature categories.

21. The system of claim 16, wherein a decision tree classifies the candidate variant as germline.

22. The system of claim 16, further comprising an output device, wherein the machine learning classifier is further configured to display a report that describes the candidate variant as including the mutation or structural alteration on the output device.

23. The method of claim 1 or the system of claim 16, wherein the sample is a biological sample.

24. The method or system of claim 23, wherein the sample is selected from the group consisting of plasma, blood, and circulating tumor DNA.

25. The method or system of claim 23, wherein the sample is from a subject having or at risk of having cancer.

26. The method or system of claim 25, wherein the cancer is selected from lung, bladder, colon, gastric, head and neck, breast, prostate, non-small cell lung adenocarcinoma, non-small cell lung squamous cell carcinoma, bladder urothelial carcinoma, colorectal, brain or pancreatic cancer.

27. The method of claim 1 or the system of claim 16, wherein a candidate variant having a confidence score ≥0.75 is classified as a somatic mutation.

* * * * *